(12) United States Patent
Riina et al.

(10) Patent No.: US 8,663,301 B2
(45) Date of Patent: Mar. 4, 2014

(54) METHOD AND APPARATUS FOR RESTRICTING FLOW THROUGH AN OPENING IN THE SIDE WALL OF A BODY LUMEN, AND/OR FOR REINFORCING A WEAKNESS IN THE SIDE WALL OF A BODY LUMEN, WHILE STILL MAINTAINING SUBSTANTIALLY NORMAL FLOW THROUGH THE BODY LUMEN

(75) Inventors: Howard Riina, Scarsdale, NY (US); Robert Andrews, Norfolk, MA (US); Clair Strohl, Norfolk, MA (US); Jeffrey Milsom, New York, NY (US); J. Frederick Cornhill, New York, NY (US); Kevin Thomas Smith, Stamford, CT (US); David G. Lamphere, Framingham, MA (US); Tuan Anh Nguyen, Woburn, MA (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 12/657,598

(22) Filed: Jan. 22, 2010

(65) Prior Publication Data

US 2010/0268260 A1 Oct. 21, 2010

Related U.S. Application Data

(63) Continuation-in-part of application No. 12/332,727, filed on Dec. 11, 2008.

(60) Provisional application No. 61/205,683, filed on Jan. 22, 2009, provisional application No. 61/277,415, filed on Sep. 24, 2009, provisional application No. 61/007,189, filed on Dec. 11, 2007.

(51) Int. Cl.
*A61F 2/06* (2013.01)
*A61F 2/02* (2006.01)
*A61M 29/00* (2006.01)

(52) U.S. Cl.
USPC .............. 623/1.11; 623/23.72; 606/200

(58) Field of Classification Search
USPC ........ 606/200, 191, 127–128; 623/1.11–1.22, 623/23.72
See application file for complete search history.

(56) References Cited

U.S. PATENT DOCUMENTS

| | | | |
|---|---|---|---|
| 4,619,246 A | | 10/1986 | Molgaard-Nielsen et al. |
| 4,994,069 A | * | 2/1991 | Ritchart et al. ............... 606/191 |

(Continued)

FOREIGN PATENT DOCUMENTS

| | | |
|---|---|---|
| CN | 1216929 | 5/1999 |
| JP | 2001-212152 | 8/2001 |

(Continued)

*Primary Examiner* — Darwin Erezo
*Assistant Examiner* — Amy Shipley
(74) *Attorney, Agent, or Firm* — Pandiscio & Pandiscio

(57) ABSTRACT

An expandable substantially spherical structure for deployment in a blood vessel or other body lumen, comprising:
an open frame formed out of a closed loop of filament and configured to assume (i) a collapsed configuration in the form of a substantially two-dimensional elongated loop structure so as to facilitate insertion into the blood vessel or other body lumen, and (ii) an expanded configuration in the form of a three-dimensional substantially spherical structure so as to facilitate retention at a site in the blood vessel or other body lumen; and
a flow-restricting face carried by the open frame;
wherein the open frame is configured so as to permit substantially normal flow therethrough when the open frame is in its expanded configuration, and further wherein the flow-restricting face is configured so as to restrict flow therethrough.

46 Claims, 61 Drawing Sheets

(56) References Cited

U.S. PATENT DOCUMENTS

| | | | |
|---|---|---|---|
| 4,994,096 A * | 2/1991 | Klein et al. ................. 95/15 |
| 5,350,398 A * | 9/1994 | Pavcnik et al. ............. 606/200 |
| 5,607,445 A * | 3/1997 | Summers .................. 623/1.22 |
| 5,645,558 A * | 7/1997 | Horton ..................... 606/191 |
| 5,669,933 A | 9/1997 | Simon et al. |
| 5,766,219 A | 6/1998 | Horton |
| 5,772,668 A | 6/1998 | Summers et al. |
| 5,810,874 A | 9/1998 | Lefebvre |
| 5,830,222 A | 11/1998 | Makower |
| 5,836,968 A | 11/1998 | Simon et al. |
| 5,851,537 A | 12/1998 | Alberts et al. |
| 5,911,731 A * | 6/1999 | Pham et al. ............... 606/191 |
| 5,925,060 A | 7/1999 | Forber |
| 5,951,599 A | 9/1999 | McCrory |
| 6,013,854 A | 1/2000 | Moriuchi |
| 6,068,638 A | 5/2000 | Makower |
| 6,090,125 A | 7/2000 | Horton |
| 6,093,199 A | 7/2000 | Brown et al. |
| 6,136,015 A * | 10/2000 | Kurz et al. ................. 606/191 |
| 6,159,165 A * | 12/2000 | Ferrera et al. ............. 600/585 |
| 6,159,225 A | 12/2000 | Makower |
| 6,165,194 A * | 12/2000 | Denardo ..................... 606/191 |
| 6,165,198 A * | 12/2000 | McGurk et al. ............. 606/200 |
| 6,171,326 B1 | 1/2001 | Ferrera et al. |
| 6,190,353 B1 | 2/2001 | Makower et al. |
| 6,221,086 B1 | 4/2001 | Forber |
| 6,231,587 B1 | 5/2001 | Makower |
| 6,283,951 B1 | 9/2001 | Flaherty et al. |
| 6,283,983 B1 | 9/2001 | Makower et al. |
| 6,302,875 B1 | 10/2001 | Makower et al. |
| 6,309,415 B1 * | 10/2001 | Pulnev et al. ............. 623/1.22 |
| 6,322,576 B1 * | 11/2001 | Wallace et al. ............. 606/191 |
| 6,325,820 B1 | 12/2001 | Khosravi et al. |
| 6,330,884 B1 | 12/2001 | Kim |
| 6,364,895 B1 | 4/2002 | Greenhalgh |
| 6,368,338 B1 * | 4/2002 | Konya et al. ............. 606/200 |
| 6,375,615 B1 | 4/2002 | Flaherty et al. |
| 6,379,319 B1 | 4/2002 | Garibotto et al. |
| 6,428,558 B1 * | 8/2002 | Jones et al. ............... 606/200 |
| 6,432,127 B1 | 8/2002 | Kim et al. |
| 6,482,222 B1 * | 11/2002 | Bruckheimer et al. ........ 606/200 |
| 6,540,657 B2 * | 4/2003 | Cross et al. ............... 600/12 |
| 6,544,230 B1 | 4/2003 | Flaherty et al. |
| 6,551,303 B1 | 4/2003 | Van Tassel et al. |
| 6,569,179 B2 * | 5/2003 | Teoh et al. ............... 606/191 |
| 6,579,311 B1 | 6/2003 | Makower |
| 6,585,748 B1 * | 7/2003 | Jeffree ..................... 606/200 |
| 6,585,756 B1 | 7/2003 | Strecker |
| 6,589,265 B1 * | 7/2003 | Palmer et al. ............. 606/200 |
| 6,592,605 B2 * | 7/2003 | Lenker et al. ............. 606/200 |
| 6,605,111 B2 * | 8/2003 | Bose et al. ............... 623/1.18 |
| 6,613,074 B1 * | 9/2003 | Mitelberg et al. .......... 623/1.11 |
| 6,613,081 B2 | 9/2003 | Kim et al. |
| 6,616,617 B1 * | 9/2003 | Ferrera et al. ............. 600/585 |
| 6,616,675 B1 | 9/2003 | Evard et al. |
| 6,632,241 B1 * | 10/2003 | Hancock et al. ............ 623/1.15 |
| 6,635,069 B1 * | 10/2003 | Teoh et al. ............... 606/200 |
| 6,638,291 B1 * | 10/2003 | Ferrera et al. ............. 606/191 |
| 6,638,293 B1 | 10/2003 | Makower et al. |
| 6,652,555 B1 | 11/2003 | Van Tassel et al. |
| 6,652,556 B1 | 11/2003 | Van Tassel et al. |
| 6,655,386 B1 | 12/2003 | Makower et al. |
| 6,656,218 B1 * | 12/2003 | Denardo et al. ............. 623/1.15 |
| 6,660,024 B1 | 12/2003 | Flaherty et al. |
| 6,685,648 B2 | 2/2004 | Flaherty et al. |
| 6,689,150 B1 | 2/2004 | Van Tassel et al. |
| 6,695,876 B1 | 2/2004 | Marotta et al. |
| 6,709,444 B1 | 3/2004 | Makower |
| 6,726,677 B1 | 4/2004 | Flaherty et al. |
| 6,730,108 B2 | 5/2004 | Van Tassel et al. |
| 6,746,464 B1 | 6/2004 | Makower |
| 6,746,468 B1 | 6/2004 | Sepetka et al. |
| 6,790,218 B2 * | 9/2004 | Jayaraman ................ 606/191 |
| 6,811,560 B2 | 11/2004 | Jones et al. |
| 6,855,155 B2 * | 2/2005 | Denardo et al. ............. 606/200 |
| 6,860,893 B2 * | 3/2005 | Wallace et al. ............. 606/200 |
| 6,863,684 B2 | 3/2005 | Kim et al. |
| 6,872,218 B2 * | 3/2005 | Ferrera et al. .............. 606/200 |
| 6,878,163 B2 * | 4/2005 | Denardo et al. ............. 623/1.15 |
| 6,894,092 B2 | 5/2005 | Sylvester |
| 6,913,618 B2 * | 7/2005 | Denardo et al. ............. 623/1.15 |
| 6,929,009 B2 | 8/2005 | Makower et al. |
| 6,929,654 B2 * | 8/2005 | Teoh et al. ............... 606/200 |
| 6,949,113 B2 | 9/2005 | Van Tassel et al. |
| 6,953,472 B2 * | 10/2005 | Palmer et al. ............. 606/200 |
| 6,984,240 B1 * | 1/2006 | Ken et al. ................. 606/200 |
| 7,059,330 B1 | 6/2006 | Makower et al. |
| 7,094,230 B2 | 8/2006 | Flaherty et al. |
| 7,134,438 B2 | 11/2006 | Makower et al. |
| 7,159,592 B1 | 1/2007 | Makower et al. |
| 7,179,270 B2 | 2/2007 | Makower |
| 7,211,107 B2 * | 5/2007 | Bruckheime et al. ........ 623/1.36 |
| 7,229,472 B2 * | 6/2007 | DePalma et al. ............ 623/1.16 |
| 7,241,310 B2 | 7/2007 | Taylor et al. |
| 7,279,000 B2 | 10/2007 | Cartier et al. |
| 7,288,112 B2 * | 10/2007 | Denardo et al. ............. 623/1.15 |
| 7,303,571 B2 | 12/2007 | Makower et al. |
| 7,306,622 B2 | 12/2007 | Jones et al. |
| 7,306,624 B2 | 12/2007 | Yodfat et al. |
| 7,316,655 B2 | 1/2008 | Garibotto et al. |
| 7,316,701 B2 * | 1/2008 | Ferrera et al. ............. 606/191 |
| 7,326,225 B2 * | 2/2008 | Ferrera et al. ............. 606/200 |
| 7,407,506 B2 | 8/2008 | Makower |
| 7,572,288 B2 * | 8/2009 | Cox ....................... 623/1.17 |
| 7,879,064 B2 * | 2/2011 | Monstadt et al. ............ 606/200 |
| 8,088,171 B2 * | 1/2012 | Brenneman ................ 623/23.72 |
| 8,092,515 B2 * | 1/2012 | Johnson et al. ............ 623/1.15 |
| 8,372,110 B2 * | 2/2013 | Monstadt et al. ............ 606/200 |
| 2001/0012961 A1 * | 8/2001 | Deem et al. ................ 623/1.15 |
| 2002/0169473 A1 * | 11/2002 | Sepetka et al. ............. 606/200 |
| 2002/0193812 A1 * | 12/2002 | Patel et al. ................ 606/151 |
| 2002/0193813 A1 * | 12/2002 | Helkowski et al. .......... 606/151 |
| 2003/0040771 A1 * | 2/2003 | Hyodoh et al. ............. 606/200 |
| 2003/0055451 A1 | 3/2003 | Jones et al. |
| 2003/0109917 A1 | 6/2003 | Rudin et al. |
| 2003/0139802 A1 | 7/2003 | Wulfman et al. |
| 2003/0216804 A1 * | 11/2003 | DeBeer et al. ............. 623/1.15 |
| 2004/0006383 A1 * | 1/2004 | Zilla et al. ............... 623/1.39 |
| 2004/0034386 A1 * | 2/2004 | Fulton et al. ............. 606/200 |
| 2004/0087998 A1 * | 5/2004 | Lee et al. ................ 606/200 |
| 2004/0098030 A1 | 5/2004 | Makower et al. |
| 2004/0153142 A1 | 8/2004 | Klumb et al. |
| 2004/0172056 A1 * | 9/2004 | Guterman et al. ........... 606/200 |
| 2004/0181253 A1 | 9/2004 | Sepetka et al. |
| 2004/0210298 A1 | 10/2004 | Rabkin et al. |
| 2004/0260384 A1 * | 12/2004 | Allen ..................... 623/1.12 |
| 2005/0107823 A1 * | 5/2005 | Leone et al. ............. 606/200 |
| 2005/0187564 A1 * | 8/2005 | Jayaraman ................ 606/141 |
| 2005/0192618 A1 * | 9/2005 | Porter .................... 606/200 |
| 2005/0192619 A1 * | 9/2005 | Teoh et al. .............. 606/200 |
| 2006/0047299 A1 * | 3/2006 | Ferguson ................. 606/200 |
| 2006/0052816 A1 | 3/2006 | Bates et al. |
| 2006/0116625 A1 | 6/2006 | Renati et al. |
| 2006/0116709 A1 * | 6/2006 | Sepetka et al. ........... 606/200 |
| 2006/0116712 A1 | 6/2006 | Sepetka et al. |
| 2006/0135947 A1 | 6/2006 | Soltesz et al. |
| 2006/0142845 A1 | 6/2006 | Molaei et al. |
| 2006/0200234 A1 | 9/2006 | Hines |
| 2006/0224183 A1 * | 10/2006 | Freudenthal .............. 606/213 |
| 2006/0241686 A1 * | 10/2006 | Ferrera et al. ............ 606/200 |
| 2007/0060994 A1 | 3/2007 | Gobran et al. |
| 2007/0083257 A1 * | 4/2007 | Pal et al. ............... 623/1.22 |
| 2007/0198075 A1 * | 8/2007 | Levy ..................... 623/1.11 |
| 2007/0219619 A1 | 9/2007 | Dieck et al. |
| 2007/0239261 A1 | 10/2007 | Bose et al. |
| 2007/0270902 A1 | 11/2007 | Slazas et al. |
| 2008/0039933 A1 | 2/2008 | Yodfat et al. |
| 2008/0045995 A1 | 2/2008 | Guterman et al. |
| 2008/0114391 A1 | 5/2008 | Dieck et al. |
| 2008/0114436 A1 | 5/2008 | Dieck et al. |

(56) References Cited

U.S. PATENT DOCUMENTS

| | | |
|---|---|---|
| 2008/0221600 A1 | 9/2008 | Dieck et al. |
| 2008/0281350 A1* | 11/2008 | Sepetka et al. ............... 606/200 |
| 2009/0062834 A1* | 3/2009 | Moftakhar et al. ........... 606/191 |
| 2009/0069836 A1* | 3/2009 | Labdag et al. ................ 606/191 |
| 2009/0125053 A1* | 5/2009 | Ferrera et al. ................ 606/200 |
| 2009/0297582 A1* | 12/2009 | Meyer et al. ................. 424/423 |

FOREIGN PATENT DOCUMENTS

| | | | |
|---|---|---|---|
| JP | 2007-536943 | | 12/2007 |
| WO | WO 97/27893 | | 8/1997 |
| WO | WO 2005/072196 | | 8/2005 |
| WO | WO2006032289 | * | 3/2006 |
| WO | WO 2006/091195 | * | 8/2006 |
| WO | WO 2008/022327 | | 2/2008 |

\* cited by examiner

Fusiform Aneurysm

Lateral Aneurysm

Bifurcation Aneurysm

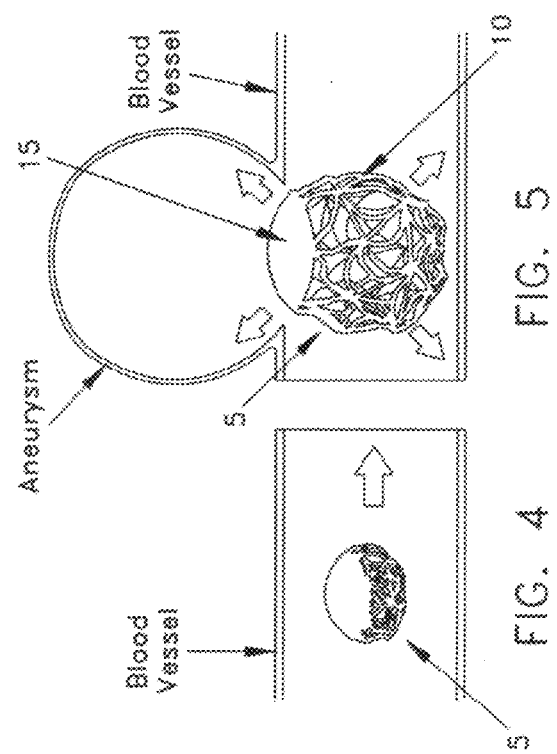
FIG. 4
FIG. 5
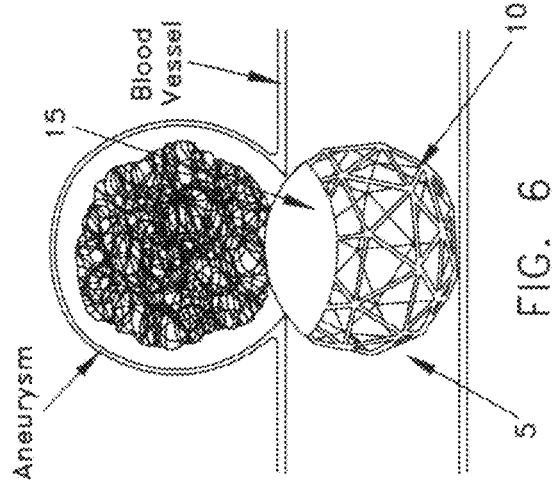
FIG. 6
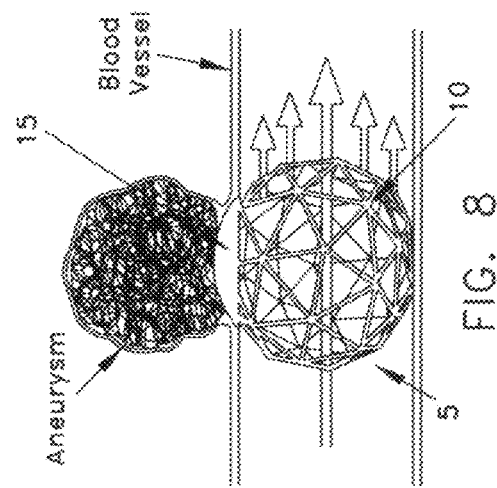
FIG. 8
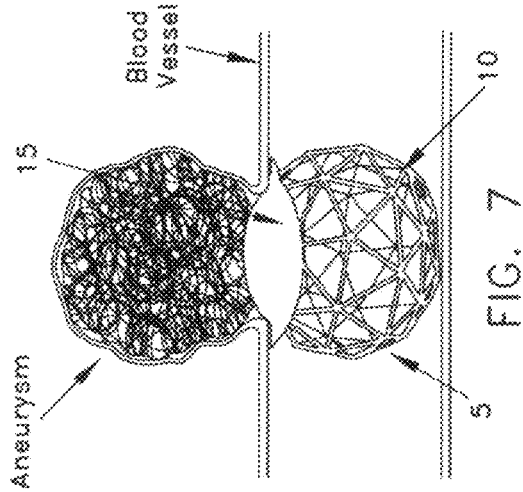
FIG. 7

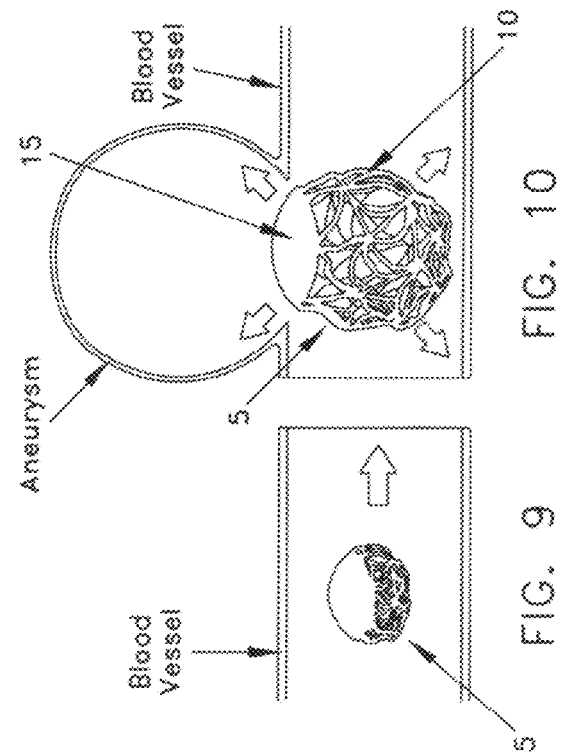
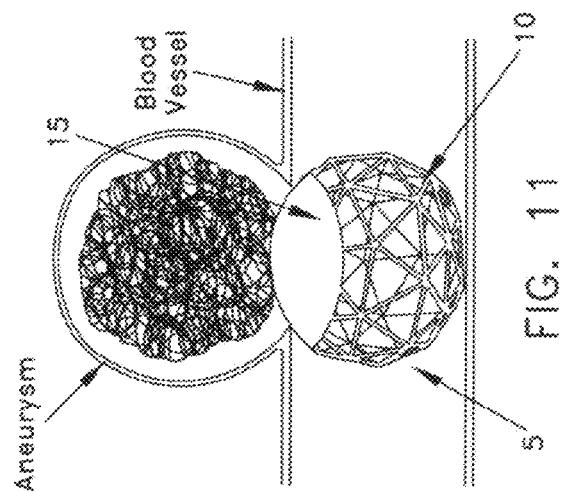
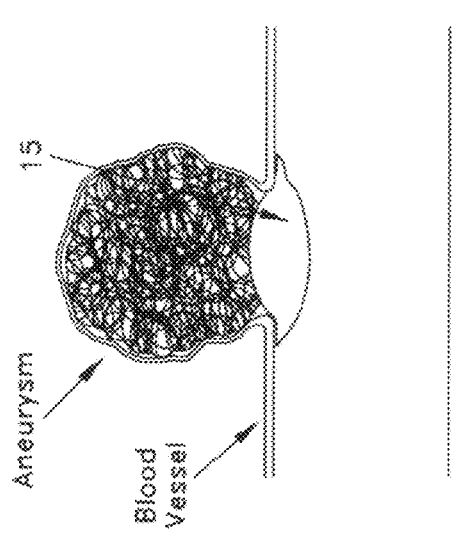
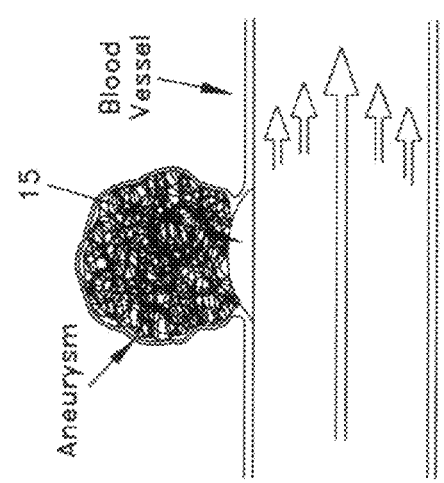

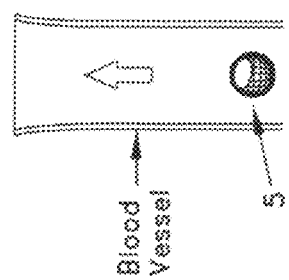
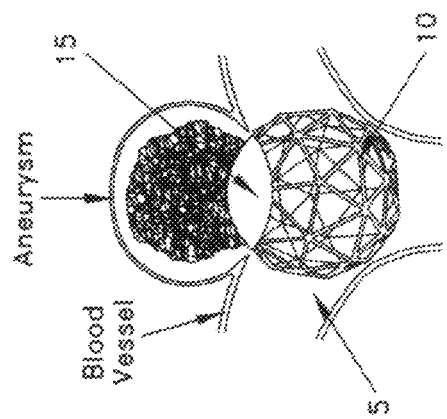
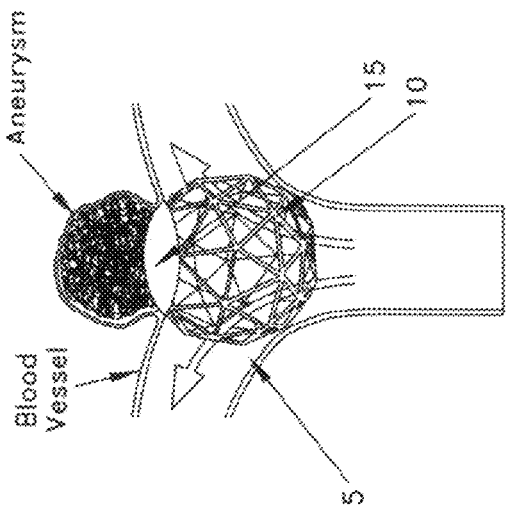
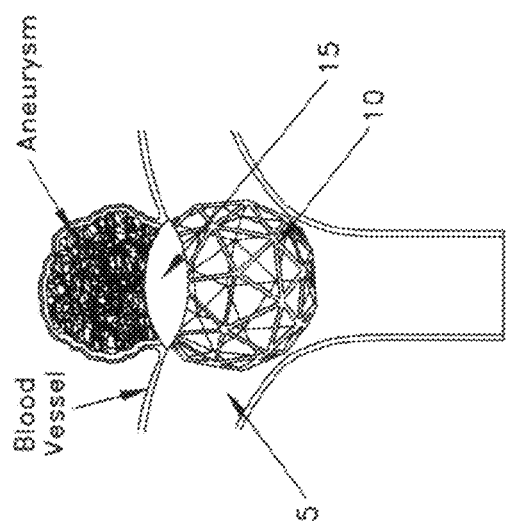
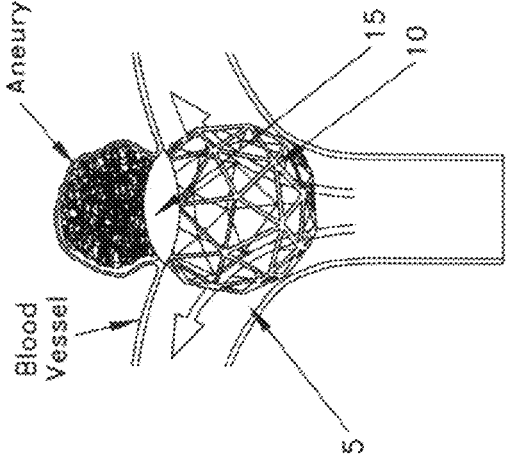

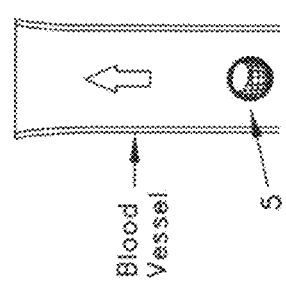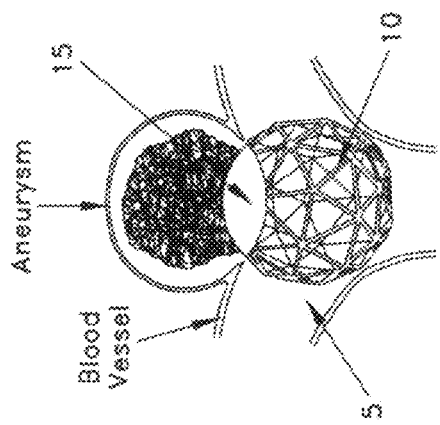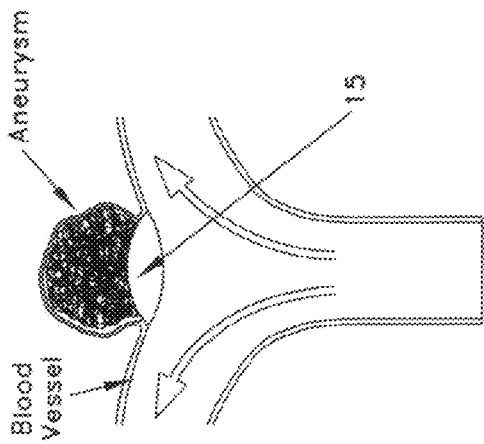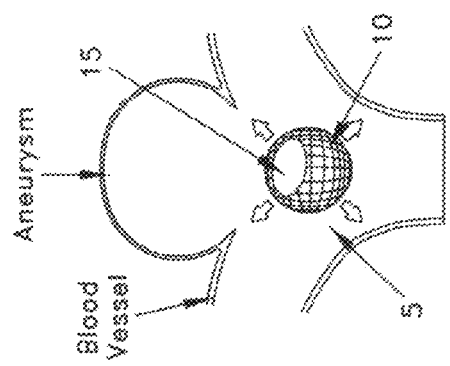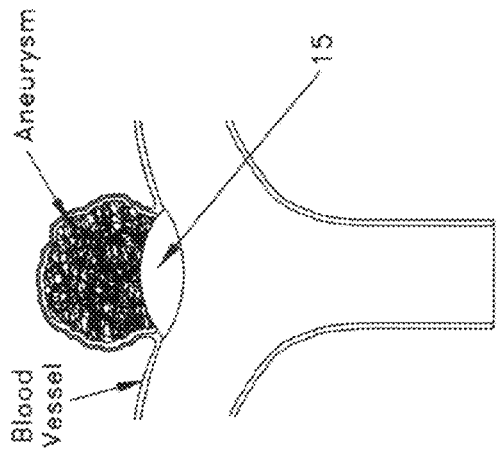

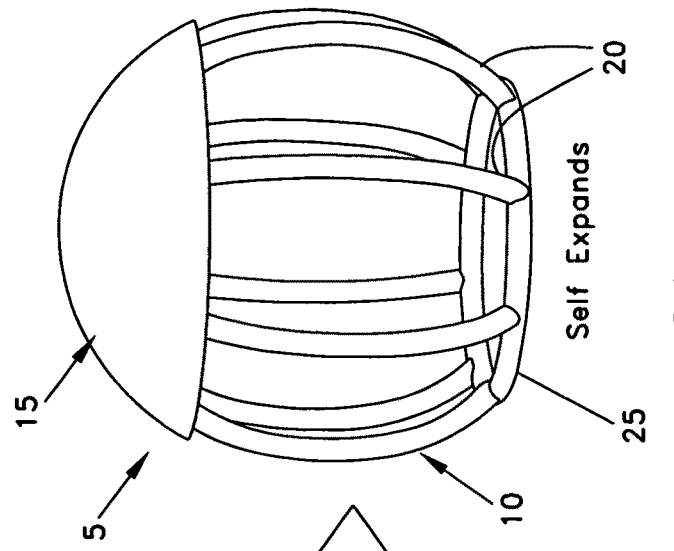
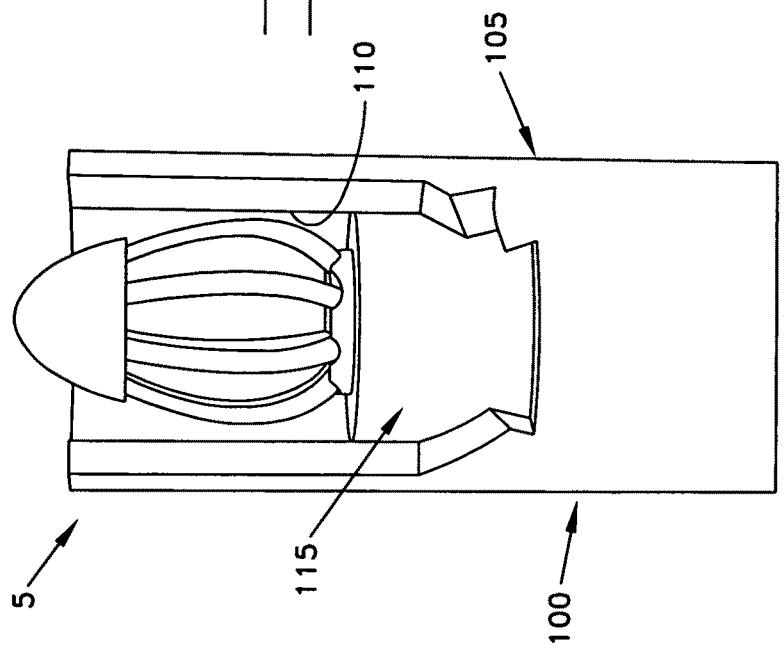

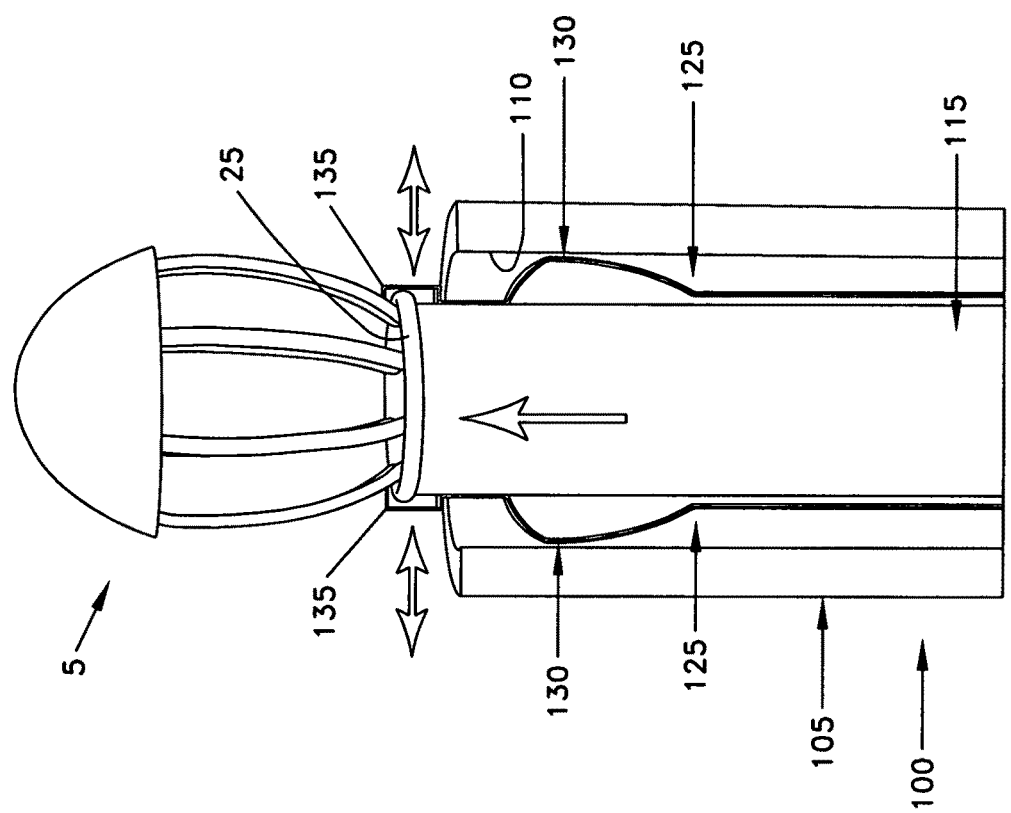

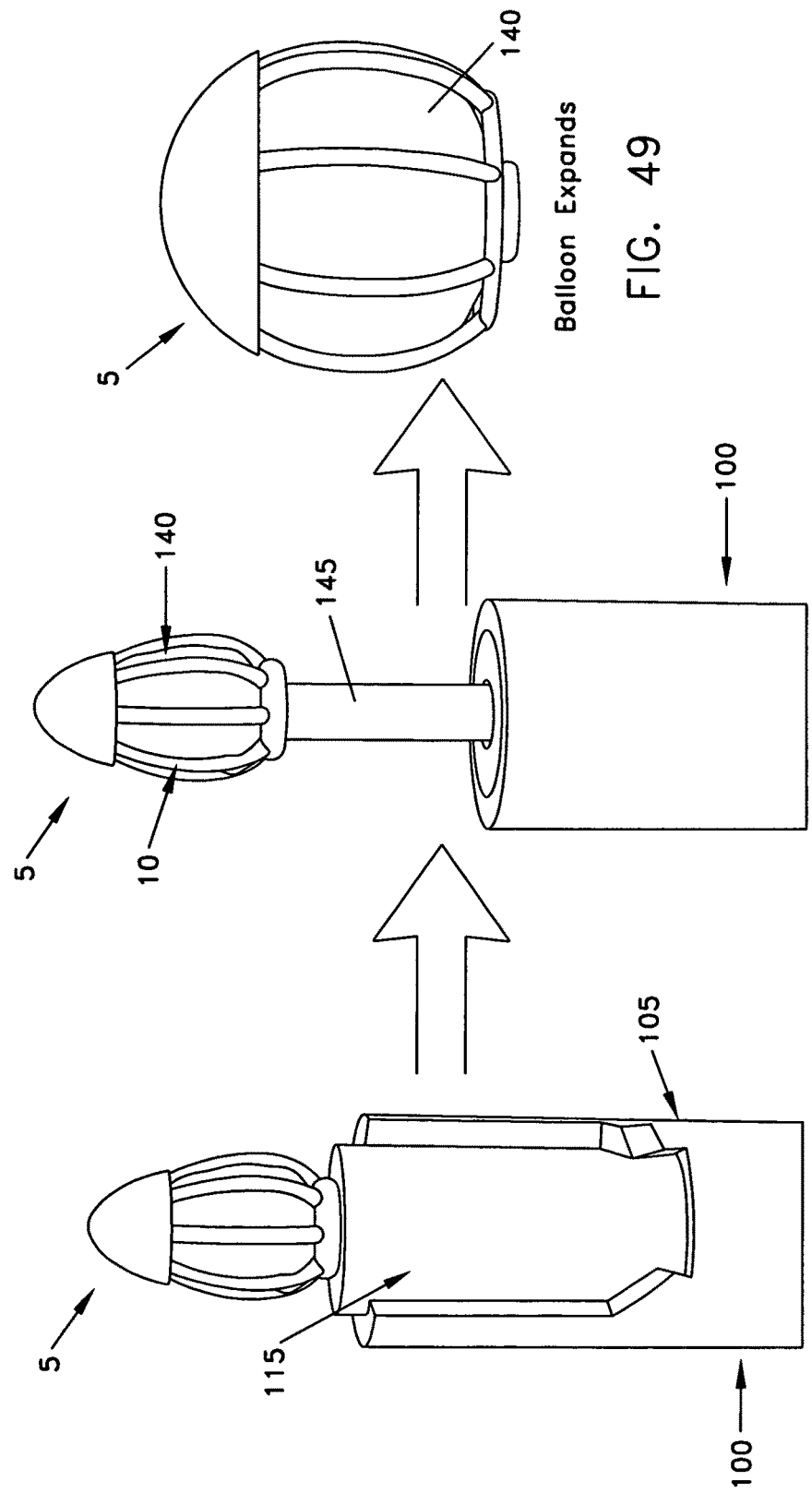

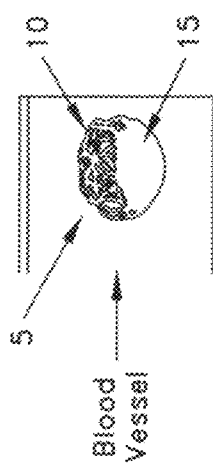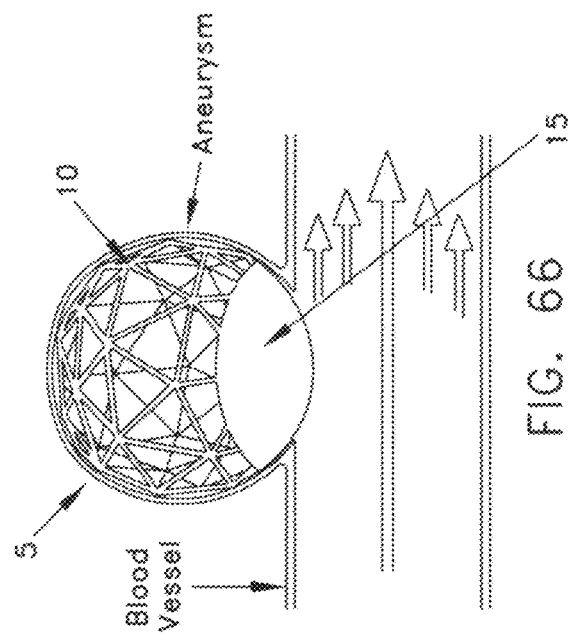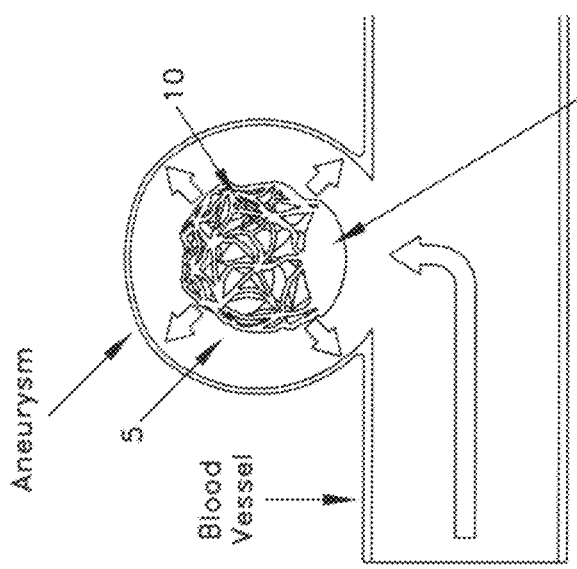

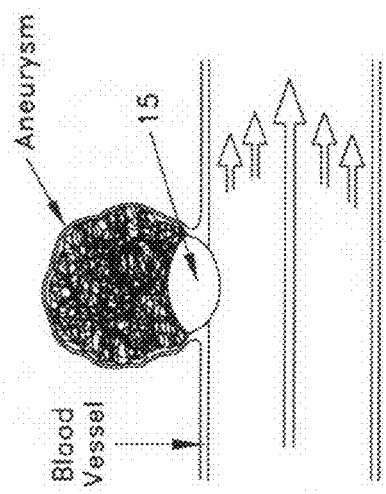
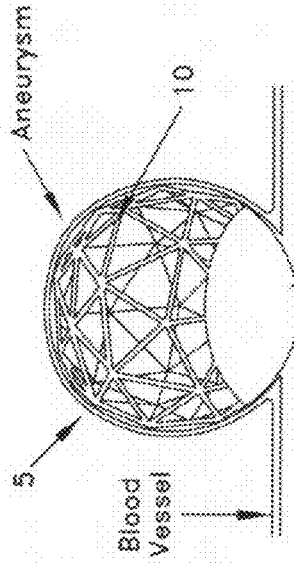
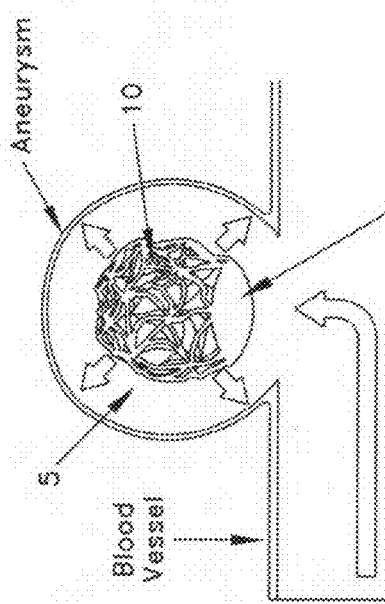
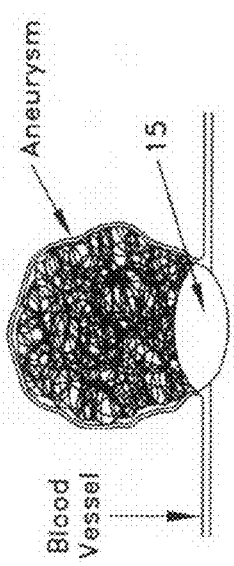
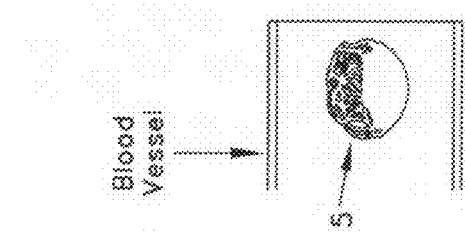

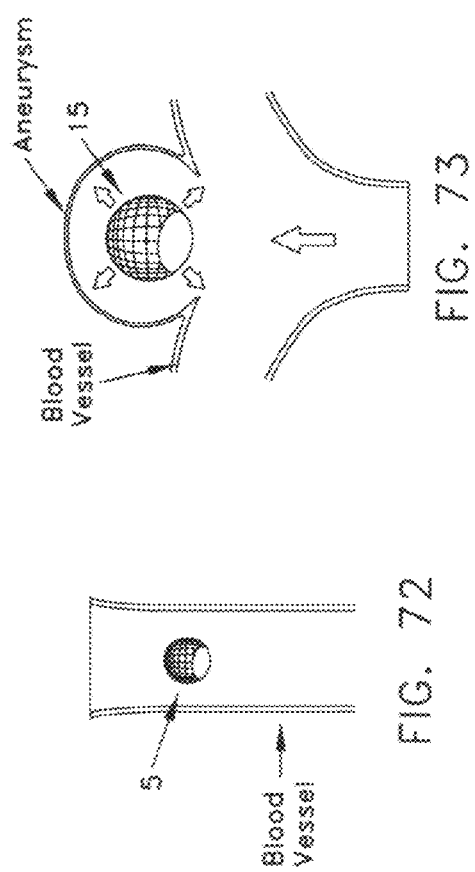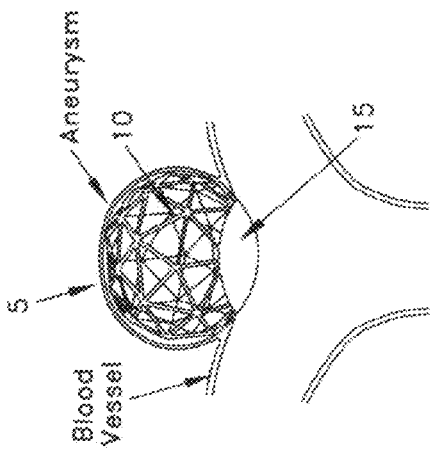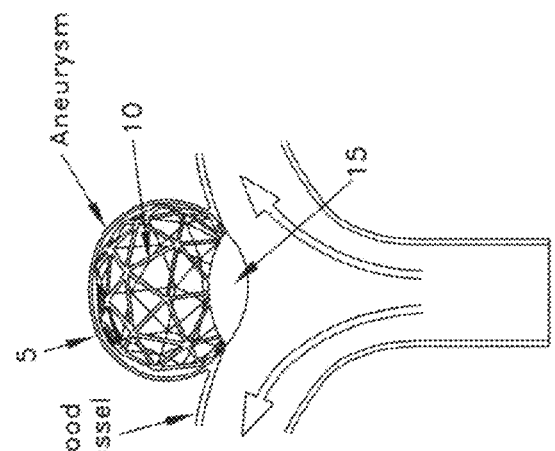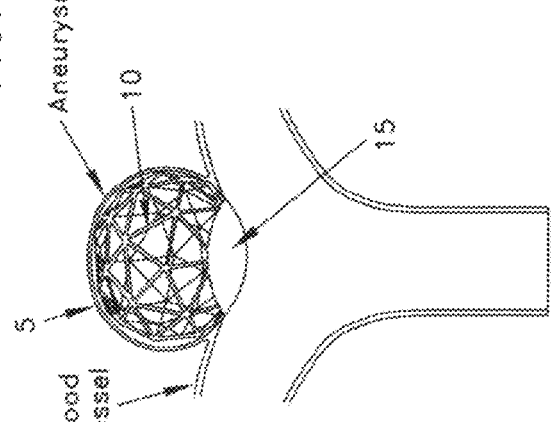

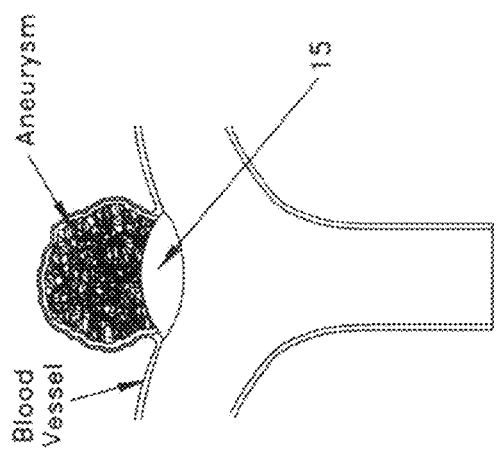
FIG. 79
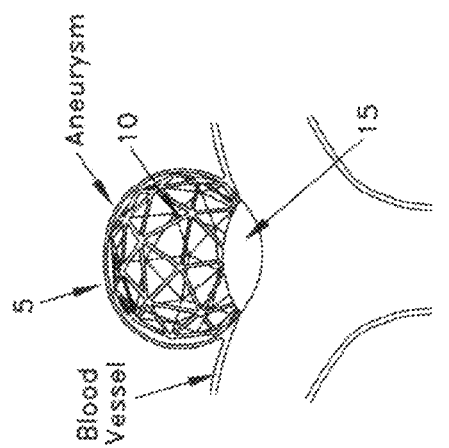
FIG. 78
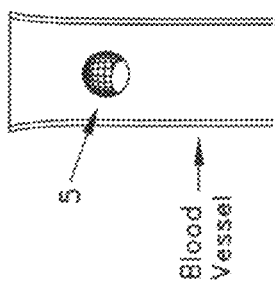
FIG. 77
FIG. 81
FIG. 80
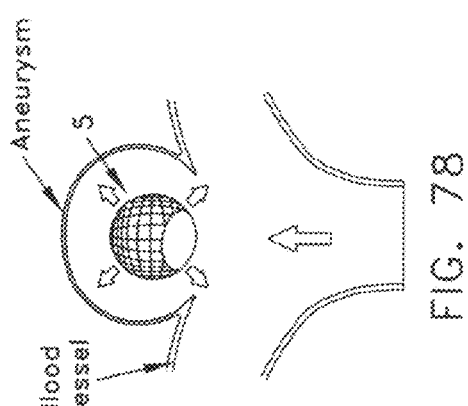

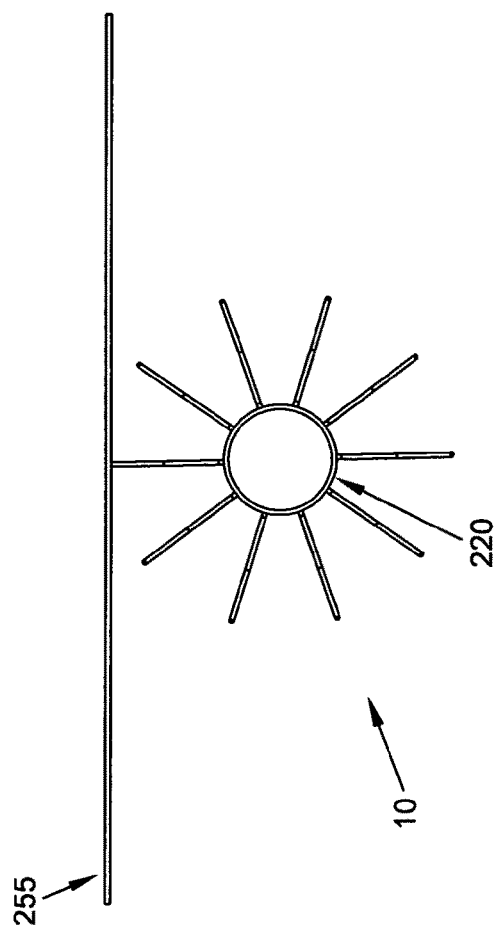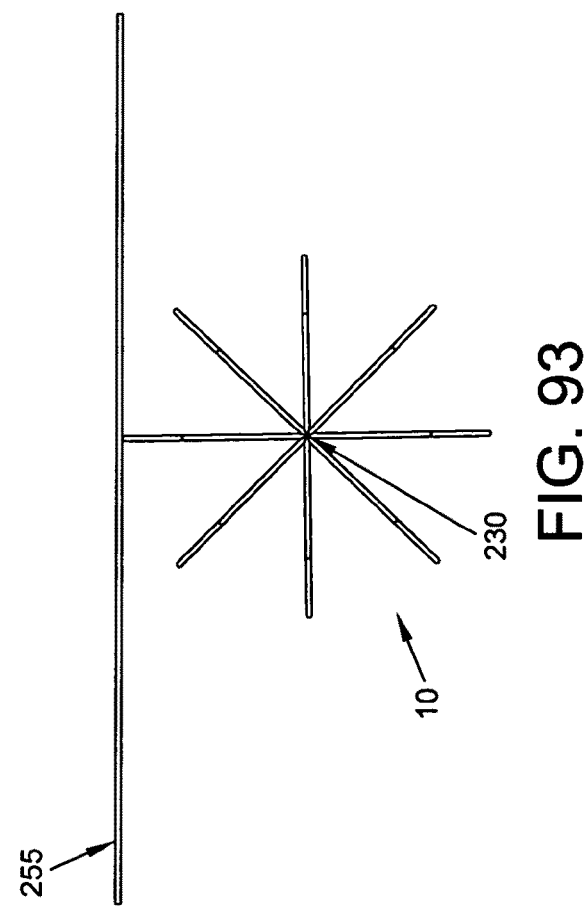

Spherical structure expanded

METHOD AND APPARATUS FOR RESTRICTING FLOW THROUGH AN OPENING IN THE SIDE WALL OF A BODY LUMEN, AND/OR FOR REINFORCING A WEAKNESS IN THE SIDE WALL OF A BODY LUMEN, WHILE STILL MAINTAINING SUBSTANTIALLY NORMAL FLOW THROUGH THE BODY LUMEN

REFERENCE TO PENDING PRIOR PATENT APPLICATIONS

This patent application:

(i) is a continuation-in-part of pending prior U.S. patent application Ser. No. 12/332,727, filed Dec. 11, 2008 by Howard Riina et al. for METHOD AND APPARATUS FOR SEALING AN OPENING IN THE SIDE WALL OF A BODY LUMEN, AND/OR FOR REINFORCING A WEAKNESS IN THE SIDE WALL OF A BODY LUMEN, WHILE MAINTAINING SUBSTANTIALLY NORMAL FLOW THROUGH THE BODY LUMEN, which in turn claims benefit of prior U.S. Provisional Patent Application Ser. No. 61/007,189, filed Dec. 11, 2007 by Howard Riina et al. for DEPLOYABLE BLOCKING SPHERE;

(ii) claims benefit of pending prior U.S. Provisional Patent Application Ser. No. 61/205,683, filed Jan. 22, 2009 by Jeffrey Milsom et al. for METHOD AND APPARATUS FOR SEALING AN OPENING IN THE SIDE WALL OF A BODY LUMEN, AND/OR FOR REINFORCING A WEAKNESS IN THE SIDE WALL OF A BODY LUMEN, WHILE MAINTAINING SUBSTANTIALLY NORMAL FLOW THROUGH THE BODY LUMEN; and (iii) claims benefit of pending prior U.S. Provisional Patent Application Ser. No. 61/277,415, filed Sep. 24, 2009 by Howard Riina et al. for METHOD AND APPARATUS FOR RESTRICTING AN OPENING IN THE SIDE WALL OF A BODY LUMEN, AND/OR FOR REINFORCING A WEAKNESS IN THE SIDE WALL OF A BODY LUMEN, WHILE MAINTAINING SUBSTANTIALLY NORMAL FLOW THROUGH THE BODY LUMEN.

The four (4) above-identified patent applications are hereby incorporated herein by reference.

FIELD OF THE INVENTION

This invention relates to medical procedures and apparatus in general, and more particularly to medical procedures and apparatus for restricting flow through an opening in the side wall of a body lumen, and/or for reinforcing a weakness in the side wall of a body lumen, while still maintaining substantially normal flow through the body lumen.

BACKGROUND OF THE INVENTION

The human body consists of many different anatomical structures. Among these anatomical structures are the blood vessels which circulate blood throughout the body, i.e., the arteries which deliver oxygenated blood to the end tissues and the veins which return oxygen-depleted blood from the end tissues.

In some cases, a blood vessel can become weakened, thereby causing the side wall of the blood vessel to balloon outwardly so as to create an aneurysm. See, for example, FIGS. 1-3, which show various types of aneurysms, e.g., a fusiform aneurysm (FIG. 1), where the aneurysm extends around a substantial portion of the circumference of a blood vessel; a lateral aneurysm (FIG. 2), where the aneurysm extends out of a limited portion of the side wall of a blood vessel, with a well-defined neck; and a bifurcation aneurysm (FIG. 3), where the aneurysm extends out of the apex of a bifurcation of a blood vessel. For purposes of the present invention, all of these aneurysms (e.g., fusiform aneurysms, lateral aneurysms and/or bifurcations aneurysms) are considered to extend out of the side wall of a blood vessel.

Aneurysms can present a serious threat to the patient, since they may enlarge to the point of rupture, thereby resulting in a rapid and uncontrolled loss of blood. Depending upon the size and location of the aneurysm, the aneurysm can be life-threatening.

By way of example but not limitation, an intracranial aneurysm can be fatal if rupture occurs. Given the life-threatening nature of such intracranial aneurysms, these aneurysms have traditionally been treated with an open craniotomy and microsurgical clipping. This procedure generally involves placing a small titanium clip across the neck of the aneurysm, thus isolating the aneurysm from blood flow and inhibiting subsequent rupture (or re-rupture). This clipping procedure is typically done under direct visualization, using an operating microscope.

More recently, minimally-invasive techniques have also been used to treat both ruptured and un-ruptured brain aneurysms. These minimally-invasive techniques generally employ interventional neuroradiological procedures utilizing digital fluoroscopy. More particularly, these interventional neuroradiological procedures generally use X-ray visualization to allow the surgeon to place a microcatheter within the dome of the aneurysm. With the microcatheter in place, detachable coils are then deployed within the dome of the aneurysm, thereby reducing blood velocity within the dome of the aneurysm and causing thrombosis of the aneurysm so as to prevent subsequent rupture (or re-rupture). However, this coil-depositing procedure has a number of drawbacks, including the risk of coil herniation into the lumen of the blood vessel; the risk of coil migration out of the aneurysm and into the blood vessel, with subsequent downstream migration; the risk of aneurysm rupture; etc.

As a result, a primary object of the present invention is to provide a new and improved device, adapted for minimally-invasive, endoluminal delivery, which may be used to restrict blood flow to an aneurysm while still maintaining substantially normal blood flow through the blood vessel.

Another object of the present invention is to provide an expandable spherical structure, comprising an open frame with a flow-restricting face (i.e., a closed face or a face having a high strut density), which may be used to restrict flow through an opening in a side wall of a blood vessel while still maintaining substantially normal blood flow through the blood vessel.

Another object of the present invention is to provide an expandable spherical structure, comprising an open frame with a flow-restricting face (i.e., a closed face or a face having a high strut density), which may be used to reinforce a weakness in a side wall of a blood vessel while still maintaining substantially normal blood flow through the blood vessel.

Another object of the present invention is to provide an expandable spherical structure, comprising an open frame with a flow-restricting face (i.e., a closed face or a face having a high strut density), which may be used to restrict flow through an opening in the side wall of a lumen other than a blood vessel, and/or so as to reinforce a weakness in a side wall of a lumen other than a blood vessel, while still maintaining substantially normal flow through the lumen.

Another object of the present invention is to provide an expandable spherical structure which may be used to facilitate the deployment of detachable coils and/or other embolic material into the interior of an aneurysm while still maintaining substantially normal flow through the blood vessel.

SUMMARY OF THE INVENTION

These and other objects of the present invention are addressed through the provision and use of a novel expandable spherical structure.

In one form of the invention, there is provided an expandable substantially spherical structure for deployment in a blood vessel or other body lumen, comprising:

an open frame formed out of a closed loop of filament and configured to assume (i) a collapsed configuration in the form of a substantially two-dimensional elongated loop structure so as to facilitate insertion into the blood vessel or other body lumen, and (ii) an expanded configuration in the form of a three-dimensional substantially spherical structure so as to facilitate retention at a site in the blood vessel or other body lumen; and a flow-restricting face carried by the open frame;

wherein the open frame is configured so as to permit substantially normal flow therethrough when the open frame is in its expanded configuration, and further wherein the flow-restricting face is configured so as to restrict flow therethrough.

In another form of the invention, there is provided a system for restricting flow to an opening in the side wall of a blood vessel or other body lumen and/or reinforcing a weakness in the side wall or apex of a bifurcation of the blood vessel or other body lumen, while maintaining substantially normal flow through the blood vessel or other body lumen, comprising:

an expandable substantially spherical structure for deployment in the blood vessel or other body lumen, comprising:

an open frame formed out of a closed loop of filament and configured to assume (i) a collapsed configuration in the form of a substantially two-dimensional elongated loop structure so as to facilitate insertion into the blood vessel or other body lumen, and (ii) an expanded configuration in the form of a three-dimensional substantially spherical structure so as to facilitate retention at a site in the blood vessel or other body lumen; and a flow-restricting face carried by the open frame;

wherein the open frame is configured so as to permit substantially normal flow therethrough when the expandable open frame is in its expanded configuration, and further wherein the flow-restricting face is configured so as to restrict flow therethrough; and an installation tool for carrying the expandable substantially spherical structure to a deployment site, wherein the installation tool comprises:

an elongated structure having a first mount for seating a first portion of the closed loop and a second mount for seating a second portion of the closed loop, the first mount and the second mount being movable relative to one another between a first position and a second position so that (i) when the first portion of the closed loop is seated in the first mount and the second portion of the closed loop is seated in the second mount and the first mount and second mount are in their first position, the open frame is in its expanded substantially spherical configuration, and (ii) when the first portion of the closed loop is seated in the first mount and the second portion of the closed loop is seated in the second mount and the first mount and second mount are in their second position, the open frame is in its collapsed and elongated configuration.

In another form of the invention, there is provided a method for restricting flow to an opening in the side wall of a body lumen while maintaining substantially normal flow through the body lumen, comprising:

providing an expandable substantially spherical structure for deployment in the body lumen, comprising:

an open frame formed out of a closed loop of filament and configured to assume (i) a collapsed configuration in the form of a substantially two-dimensional elongated loop structure so as to facilitate insertion into the blood vessel or other body lumen, and (ii) an expanded configuration in the form of a three-dimensional substantially spherical structure so as to facilitate retention at a site in the blood vessel or other body lumen; and a flow-restricting face carried by the open frame;

wherein the open frame is configured so as to permit flow therethrough when the open frame is in its expanded configuration, and further wherein the flow-restricting face is configured so as to restrict flow therethrough;

delivering the expandable substantially spherical structure to a therapy site within the body lumen while the open frame is in its collapsed configuration; and transforming the expandable substantially spherical structure from its collapsed configuration to its expanded configuration so that the expandable substantially spherical structure is securely lodged in the body lumen, with the flow-restricting face of the expandable substantially spherical structure positioned so as to restrict flow to the opening in the side wall of the body lumen and with the open frame permitting flow through the body lumen.

In another form of the invention there is provided an expandable substantially spherical structure for deployment in a blood vessel or other body lumen, comprising:

an open frame configured to assume a collapsed configuration and an expanded configuration;

a flow-restricting face carried by the open frame; and a plurality of stabilizing legs attached to, and extending away from, the open frame;

wherein the open frame and the plurality of stabilizing legs are configured so as to permit substantially normal flow therethrough when the open frame is in its expanded configuration, and further wherein the flow-restricting face is configured so as to restrict flow therethrough.

In another form of the invention, there is provided a method for restricting flow through an opening in the side wall of a body lumen while maintaining substantially normal flow through the body lumen, comprising:

providing an expandable substantially spherical structure for deployment in the body lumen, comprising:

an open frame configured to assume a collapsed configuration and an expanded configuration;

a flow-restricting face carried by the open frame; and a plurality of stabilizing legs attached to, and extending away from, the open frame;

wherein the open frame and the plurality of stabilizing legs are configured so as to permit flow therethrough when the open frame is in its expanded configuration, and further wherein the flow-restricting face is configured so as to restrict flow therethrough;

delivering the expandable substantially spherical structure to a therapy site within the body lumen while the open frame is in its collapsed configuration and the plurality of stabilizing legs are in a collapsed configuration; and transforming the expandable substantially spherical structure from its collapsed configuration to its expanded configuration, and transforming the plurality of stabilizing legs from their collapsed configuration to an expanded configuration, so that the expandable substantially spherical structure is securely lodged in the body lumen, with the flow-restricting face of the expandable substantially spherical structure positioned so as to restrict flow to the opening in the side wall of the body lumen and with the open frame and the plurality of stabilizing legs permitting flow through the body lumen.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 4-8 are schematic views showing a novel expandable spherical structure formed in accordance with the present invention, wherein the expandable spherical structure comprises an open frame with a flow-restricting face (i.e., a closed face in this particular embodiment), and wherein the expandable spherical structure is shown being used to close off a lateral aneurysm in a blood vessel;

FIGS. 9-13 are schematic views showing another novel expandable spherical structure formed in accordance with the present invention, wherein the expandable spherical structure comprises an open frame with a flow-restricting face (i.e., a closed face in this particular embodiment), wherein the open frame is formed out of an absorbable material and the closed face is formed out of a non-absorbable material, and wherein the expandable spherical structure is shown being used to close off a lateral aneurysm in a blood vessel;

FIGS. 14-18 are schematic views showing the expandable spherical structure of FIGS. 4-8 being used to close off a bifurcation aneurysm;

FIGS. 19-23 are schematic views showing the expandable spherical structure of FIGS. 9-13 being used to close off a bifurcation aneurysm;

FIGS. 44 and 45 are schematic views showing the expandable spherical structure of FIG. 27 being deployed with a syringe-type (e.g., an outer sleeve with an internal pusher) installation tool;

FIG. 46 is a schematic view showing the expandable spherical structure of FIG. 27 being deployed with a syringe-type installation tool equipped with a gripper mechanism;

FIGS. 47-49 are schematic views showing the expandable spherical structure of FIG. 27 being deployed with a syringe-type installation tool equipped with an expansion balloon;

FIGS. 64-66 are schematic views showing the expandable spherical structure of FIGS. 4-8 being deployed within the interior of a lateral aneurysm so as to close off the aneurysm;

FIGS. 67-71 are schematic views showing the expandable spherical structure of FIGS. 9-13 being deployed within the interior of a lateral aneurysm so as to close off the aneurysm;

FIGS. 72-76 are schematic views showing the expandable spherical structure of FIGS. 4-8 being deployed within the interior of a bifurcation aneurysm so as to close off the aneurysm;

FIGS. 77-81 are schematic views showing the expandable spherical structure of FIGS. 9-13 being deployed within the interior of a bifurcation aneurysm so as to close off the aneurysm;

FIGS. 84-97 are schematic views showing various constructions for the "comet-shaped" structure of FIGS. 82 and 83, but with the flow-restricting face of the expandable spherical structure being omitted in FIGS. 84-91 for clarity of viewing;

DETAILED DESCRIPTION OF THE PREFERRED EMBODIMENTS

Figure 1:
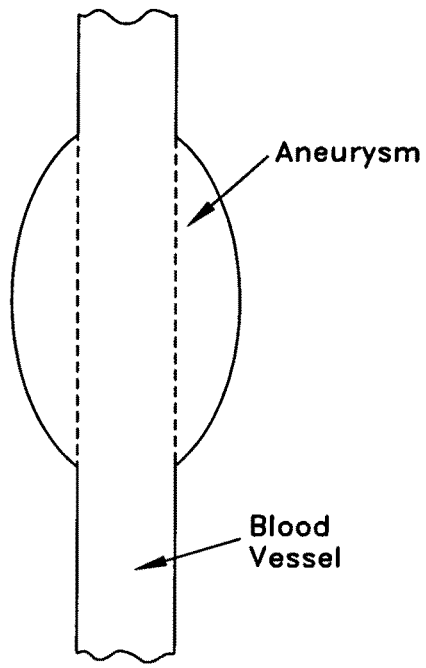
FIGS. 1-3 are schematic views showing various types of aneurysms.
Figure 2:
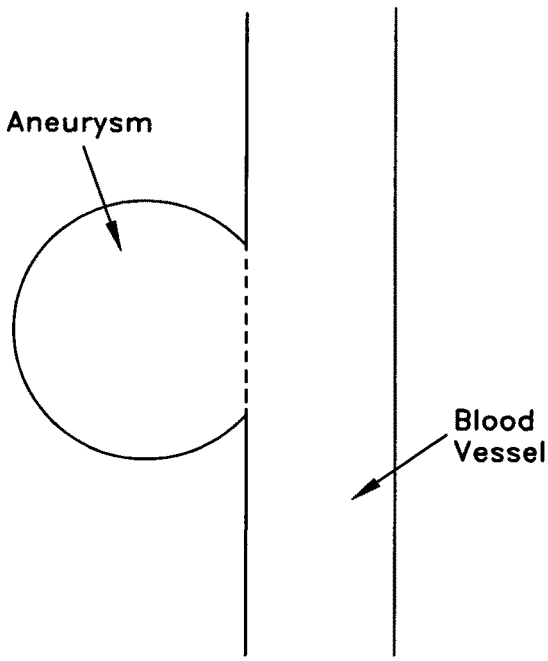
Figure 3:
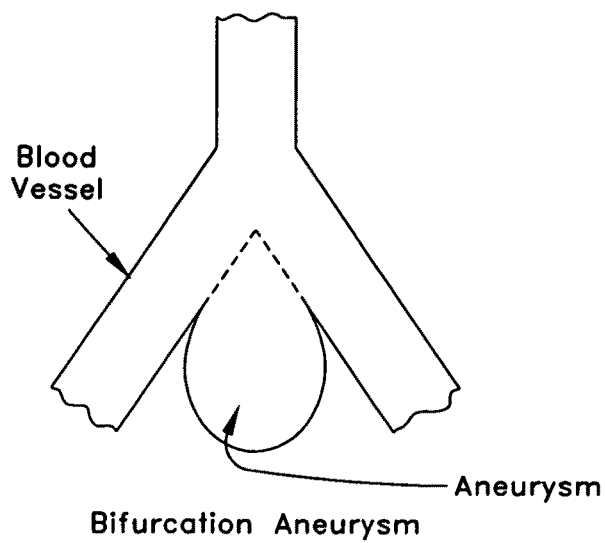

The Novel Expandable Spherical Structure in General

Looking now at FIGS. 4-8, there is shown a novel expandable spherical structure 5 formed in accordance with the present invention. Expandable spherical structure 5 is adapted for minimally-invasive, endoluminal delivery into a blood vessel or other body lumen, for restricting flow through an opening in the side wall of the blood vessel or other body lumen, and/or for reinforcing a weakness in the side wall of the blood vessel or other body lumen, while still maintaining substantially normal flow through the blood vessel or other body lumen.

Expandable spherical structure 5 generally comprises a spherical body comprising an open frame 10 with a flow-restricting face 15 (i.e., a closed face or a face having a high strut density). Preferably open frame 10 and flow-restricting face 15 together define the entire exterior shape of the spherical body, with open frame 10 making up the majority of the exterior shape of the spherical body.

In one preferred form of the invention, open frame 10 defines approximately 90% of the exterior shape of the spherical body and flow-restricting face 15 defines approximately 10% of the exterior shape of the spherical body. In another preferred form of the invention, open frame 10 defines approximately 80% of the exterior shape of the spherical body and flow-restricting face 15 defines approximately 20% of the exterior shape of the spherical body. In yet another preferred form of the invention, open frame 10 comprises approximately 70% of the exterior shape of the spherical body and flow-restricting face 15 defines approximately 30% of the exterior shape of the spherical body. And in yet another preferred form of the invention, open frame 10 comprises approximately 60% of the exterior shape of the spherical body and flow-restricting face 15 comprises approximately 40% of the exterior shape of the spherical body.

Expandable spherical structure 5 is constructed so that it may be deployed in a blood vessel or other body lumen, by (i) collapsing the expandable spherical structure into a configuration of reduced dimension, (ii) moving the collapsed structure through the blood vessel or other body lumen to a therapy site, and (iii) expanding the collapsed structure to an enlarged dimension at the therapy site, whereby to secure the expandable spherical structure in the blood vessel or body lumen so that its flow-restricting face 15 is presented to a side wall of the blood vessel or other body lumen, whereby to restrict flow to an aneurysm or other opening in the side wall of the blood vessel or other body lumen, or to otherwise reinforce a weakness in the side wall of the blood vessel or other body lumen, without significantly impeding normal flow through the blood vessel or other body lumen.

Significantly, by forming expandable spherical structure 5 in the shape of a spherical body, the endoluminal device is readily centered on the neck of an aneurysm or other opening in a body lumen, with flow-restricting face 15 projecting into the neck of the aneurysm or other opening in a body lumen and reliably restricting flow into the aneurysm or other opening in a body lumen.

Furthermore, by forming expandable spherical structure 5 so that it can expand at the therapy site and lodge itself in the blood vessel or other body lumen with its flow-restricting face 15 presented to a side wall of the blood vessel or other body lumen, expandable spherical structure 5 is effectively self-sizing, since it can be expanded to the degree necessary to span the blood vessel or other body lumen.

More particularly, expandable spherical structure 5 generally comprises an open frame 10 which has a flow restricting face 15 (i.e., a closed face or a face having a high strut density) carried thereon. Open frame 10 is formed so that it can assume a first, collapsed configuration of reduced dimension (FIG. 4) so as to facilitate moving expandable spherical structure 5 endoluminally through the blood vessel or other body lumen to the therapy site. Open frame 10 is also formed so that it can thereafter be re-configured to a second, expanded configuration of enlarged dimension (FIGS. 5 and 6), whereby expandable spherical structure 5 can be lodged in the blood vessel or other body lumen at the therapy site, with its flow-restricting face 15 pressed securely against a side wall of the blood vessel or other body lumen. In this position, flow-restricting face 15 of expandable spherical structure 5 can restrict flow to an aneurysm in the blood vessel (such as the lateral aneurysm shown in FIGS. 4-8, or a bifurcation aneurysm as will hereinafter be discussed below), or restrict flow to an opening in the side wall of the blood vessel or other body lumen, or reinforce a weakness in the side wall of the blood vessel or other body lumen, etc.

Significantly, by forming the endoluminal device as an expandable spherical structure, the device can be collapsed to a reduced dimension for minimally-invasive, endoluminal delivery into a blood vessel or other body lumen, yet can thereafter be expanded to the required dimension for secure lodgment at the therapy site, whereby to restrict flow to an opening in a body lumen and/or to reinforce a weakness in the side wall of the body lumen. Furthermore, by forming expandable spherical structure 5 in the shape of a spherical body, the endoluminal device is readily centered on the neck of an aneurysm or other opening in a body lumen, with flow-restricting face 15 projecting into the neck of the aneurysm or other opening in a body lumen and reliably restricting flow into the aneurysm or other opening in a body lumen. And by forming expandable spherical structure 5 so that it can expand at the therapy site and lodge itself in the blood vessel or other body lumen with its flow-restricting face 15 presented to a side wall of the blood vessel or other body lumen, expandable spherical structure 5 is effectively self-sizing, since it expands to the degree necessary to span the blood vessel or other body lumen. Additionally, by forming open frame 10 as an open structure, expandable spherical structure 5 can be disposed in the blood vessel or body lumen without significantly impeding normal flow through the blood vessel or other body lumen (FIGS. 6-8).

Expandable Open Frame 10

As noted above, (i) expandable spherical structure 5 generally comprises a spherical body comprising an open frame 10 with a flow-restricting face 15 (i.e., a closed face or a face having a high strut density); (ii) open frame 10 and flow-restricting face 15 together preferably define the entire exterior shape of the spherical body, with open frame 10 making up the majority of the exterior shape of the spherical body; (iii) open frame 10 is capable of being collapsed in dimension for easy delivery of expandable spherical structure 5 to the therapy site and thereafter expanded in dimension at the therapy site so as to hold flow-restricting face 15 against a side wall of a blood vessel or other body lumen; and (iv) open frame 10 is configured so that it does not significantly impede normal flow through the blood vessel or lumen within which it is deployed.

To this end, open frame 10 is preferably formed with an expandable strut construction, so that it can (i) first assume a configuration of reduced dimension, so that expandable spherical body 5 can move easily through the body to the therapy site, and (ii) thereafter assume a configuration of expanded dimension, so that it can be securely retained at the desired location in the blood vessel or other body lumen and press flow-restricting face 15 securely against the side wall of the blood vessel or body lumen, whereby to restrict flow to an aneurysm or other opening in the blood vessel or other body lumen, or to otherwise reinforce the side wall of the blood vessel or other body lumen. And by forming open frame 10 with an expandable strut construction, open frame 10 is effectively self-sizing, since it expands to the degree necessary to span the blood vessel or other body lumen.

Significantly, by forming open frame 10 with an expandable strut construction, open frame 10 does not significantly impede normal flow through the blood vessel or other body lumen when open frame 10 is in its expanded configuration within the blood vessel or other body lumen.

Thus, for example, in the configuration shown in FIGS. 4-8, open frame 10 comprises a plurality of struts arranged in a polygonal configuration, with the struts being sized so that the struts present minimal obstruction to normal flow through the lumen.

In one preferred construction, open frame 10 may be formed out of a shape memory alloy (SMA) such as Nitinol, and a temperature transition may be used to change the configuration of open frame 10. By way of example but not limitation, open frame 10 can be formed so that when it is cooled to a temperature below body temperature, the open frame assumes a collapsed configuration (FIG. 4), and when it is thereafter warmed to body temperature, the open frame assumes an expanded configuration (FIG. 6). If desired, open frame 10 can be warmed to body temperature simply by deploying expandable spherical structure 5 in the body. Alternatively, an electrical current may be applied to open frame 10 so as to heat open frame 10 to its expansion temperature, e.g., via resistance heating. Or, a warm or cold saline solution can be flushed through open frame 10 so as to appropriately modulate the temperature of the open frame, whereby to cause the open frame to assume a desired configuration.

Alternatively, open frame 10 can be formed out of a resilient material which can be forcibly compressed into a collapsed configuration, restrained in this collapsed configuration, and thereafter released so that it elastically returns to its expanded configuration. By way of example but not limitation, in this form of the invention, expandable spherical structure 5 might be compressed into a configuration of a reduced dimension, restrained within a sleeve, delivered to the therapy site within the sleeve, and then released from the sleeve so that it elastically returns to an expanded configuration at the therapy site, whereby to lodge itself in the blood vessel or other body lumen, with its flow-restricting face pressed against the side wall of the blood vessel or other body lumen. By way of further example but not limitation, open frame 10 can be formed out of a shape memory alloy (SMA) engineered to form stress-induced martensite (SIM) and thereby exhibit superelastic properties, whereby to permit large shape deformations with elastic return. By way of still further example but not limitation, open frame 10 can be formed out of a suitable polymer which exhibits the desired elastic properties.

In another preferred form of the present invention, open frame 10 is formed with a structure which can be collapsed for delivery to the deployment site and thereafter enlarged to an expanded configuration through the use of an expansion device, e.g., an internal balloon, where the balloon is inflated at the therapy site so as to reconfigure open frame 10 to an expanded condition. This arrangement can be advantageous, since it does not require the open frame to rely on temperature transition or elasticity to expand to its fully expanded configuration (or to any desired expanded configuration less than its fully expanded configuration). Thus, a wide range of well known biocompatible materials (e.g., medical grade stainless steel) may be used to form open frame 10.

Flow-Restricting Face 15

Flow-restricting face 15 is carried by (e.g., mounted on, formed integral with, or otherwise connected to) open frame 10 so that flow-restricting face 15 can be pressed securely against the side wall of the blood vessel or other body lumen within which expandable spherical structure 5 is deployed.

Flow-restricting face 15 may comprise a closed face, in the sense that it comprises a substantially complete surface or barrier which is capable of closing off an aneurysm or other opening in side wall of a blood vessel or other body lumen, and/or for reinforcing a weakness in the side wall of the blood vessel or other body lumen. See FIGS. 4-8, where flow-restricting face 15 is depicted as a closed face.

Alternatively, and as will be discussed in detail below, flow-restricting face 15 may comprise a face having a high strut density which is capable of restricting flow to an aneurysm or other opening in a side wall of a blood vessel or other body lumen, and/or for reinforcing a weakness in the sidewall of the blood vessel or other body lumen. In this case, flow-restricting face 15 may not constitute a substantially complete surface, or flow-restricting face 15 may not constitute a substantially fluid-impervious surface, but flow-restricting face 15 will have a strut density sufficiently high to restrict flow through that face, e.g., so as to cause an aneurysm to thrombose.

Flow-restricting face 15 may be formed so as to be substantially rigid or it may be formed so as to be flexible.

Flow-restricting face 15 preferably has the convex configuration shown in FIGS. 4-8, so that it can form a regular portion of the spherical body of expandable structure 5. However it should be appreciated that flow-restricting face 15 may also be formed with a planar configuration, or some other configuration, if desired.

Use of Absorbable Materials

If desired, expandable spherical structure 5 can have some or all of its elements formed out of an absorbable material, so that some or all of the elements are removed from the therapy site after some period of time has elapsed.

By way of example but not limitation, open frame 10 can be formed out of an absorbable material, and flow-restricting face 15 can be formed out of a non-absorbable material, so that only flow-restricting face 15 is retained at the therapy site after some period of time has passed. See FIGS. 9-13. This type of construction can be advantageous where flow-restricting face 15 integrates into the side wall of the blood vessel or other body lumen after some period of time has elapsed, so that a supporting frame is no longer necessary to hold flow-restricting face 15 in position against the side wall of the blood vessel or other body lumen.

It is also possible for the entire expandable spherical structure 5 to be formed out of absorbable material(s), i.e., with both open frame 10 and flow-restricting face 15 being formed out of absorbable materials. This type of construction can be advantageous where flow-restricting face 15 only needs to be held against the side wall of the blood vessel or other body lumen for a limited period of time, e.g., until aneurysm thrombosis/scarring is complete, or to reinforce the side wall of the blood vessel or other body lumen while healing occurs, etc.

It should also be appreciated that, where both open frame 10 and flow-restricting face 15 are absorbable, they may be engineered so as to have different absorption rates, so that they are removed from the therapy site at different times. This may be done by making the various elements out of different materials, or by making the various elements out of different blends of the same materials, etc.

Application to Different Types of Aneurysms

As noted above, expandable spherical structure 5 can be used to restrict flow to various types of aneurysms.

Thus, for example, FIGS. 4-8 and 9-13 show expandable spherical structure 5 being used to restrict flow to a lateral aneurysm (i.e., in these particular embodiments, to close off the lateral aneurysm).

However, it should also be appreciated that expandable spherical structure 5 may be used to restrict flow to a bifurcation aneurysm as well. Thus, for example, FIGS. 14-18 show the expandable spherical structure 5 of FIGS. 4-8 being used restrict flow to a bifurcation aneurysm, and FIGS. 19-23 show the expandable spherical structure 5 of FIGS. 9-13 being used to restrict flow to a bifurcation aneurysm (i.e., in these particular embodiments, to close off the bifurcation aneurysm). In this respect it should be appreciated that the spherical shape of expandable spherical structure 5 is particularly well suited for use in treating bifurcation aneurysms, since it may be seated securely at the bifurcation, pressing flow-restricting face 15 securely against the bifurcation aneurysm, while still allowing blood to flow substantially unobstructed through the blood vessels.

It is also anticipated that expandable spherical structure 5 may be used to restrict flow to other types of aneurysms as well, e.g., certain forms of fusiform aneurysms. Where expandable spherical structure 5 is to be used to restrict flow to a fusiform aneurysm, flow-restricting face 15 may comprise a significantly enlarged surface area, or flow-restricting face 15 may comprise two or more separated segments disposed about the lateral portions of open frame 10, etc.

Structure of Open Frame 10

It should be appreciated that open frame 10 can be formed with a variety of different configurations without departing from the scope of the present invention.

Figure 24:
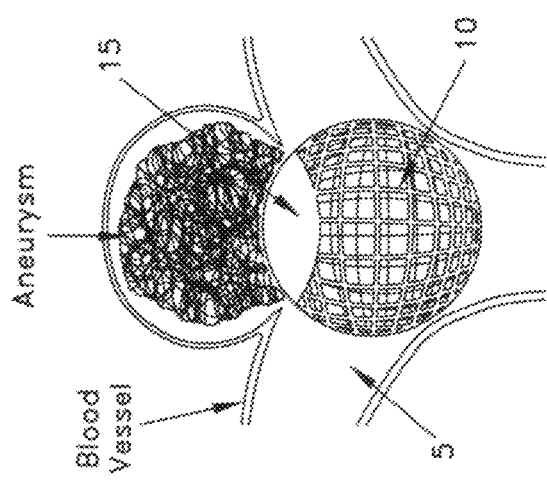
FIG. 24 is a schematic view showing another novel expandable spherical structure formed in accordance with the present invention, wherein the expandable spherical structure comprises an open frame with a flow-restricting face (i.e., a closed face in this particular embodiment), and wherein the open frame of the expandable spherical structure comprises a plurality of struts arranged in a rectangular pattern.
Figure 25:
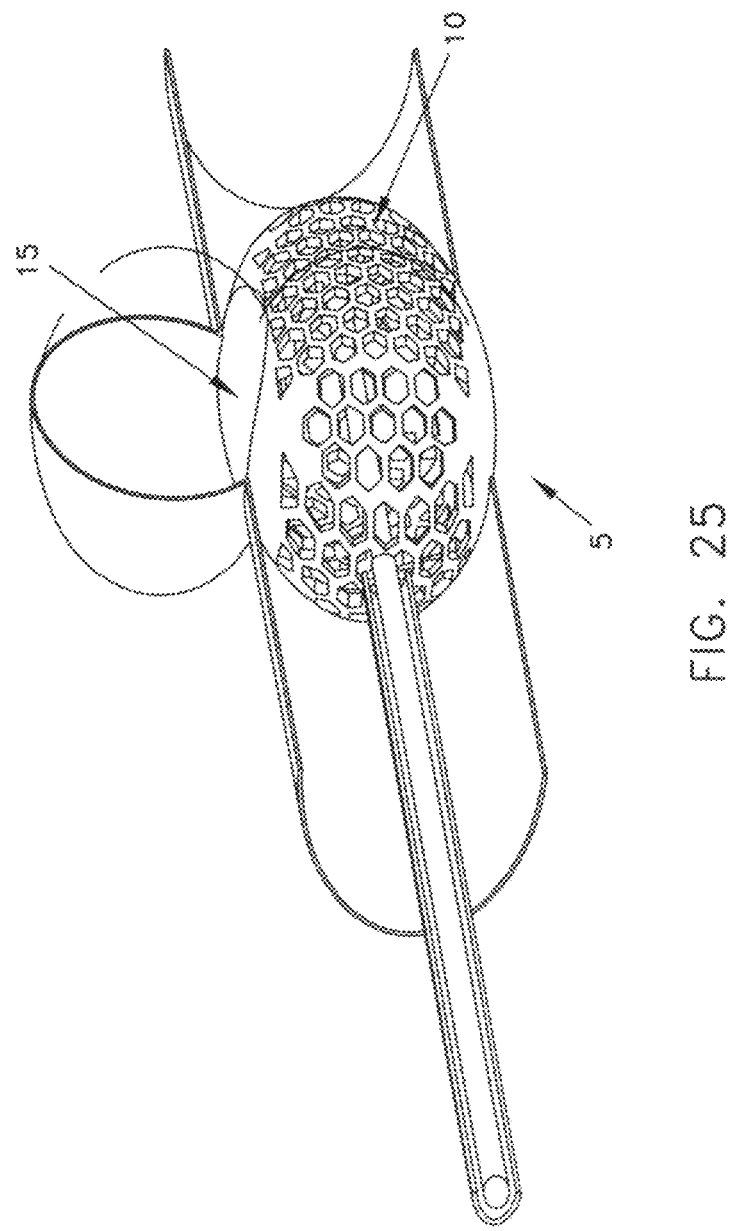
FIG. 25 is a schematic view showing another novel expandable spherical structure formed in accordance with the present invention, wherein the open frame comprises a plurality of struts arranged in a hexagonal pattern.

In one form of the invention, open frame 10 may be formed out of a plurality of struts arranged in a polygonal array. See, for example, FIGS. 4-8, 9-13, 14-18 and 19-23, where open frame 10 is shown formed out of a plurality of struts arranged as triangular polygons. See also FIG. 24, where open frame 10 is formed out of a plurality of struts arranged as rectangular polygons, and FIG. 25, where open frame 10 is formed out of a plurality of struts arranged as hexagons.

It is also possible to form open frame 10 with a non-polygonal structure.

Figure 26:
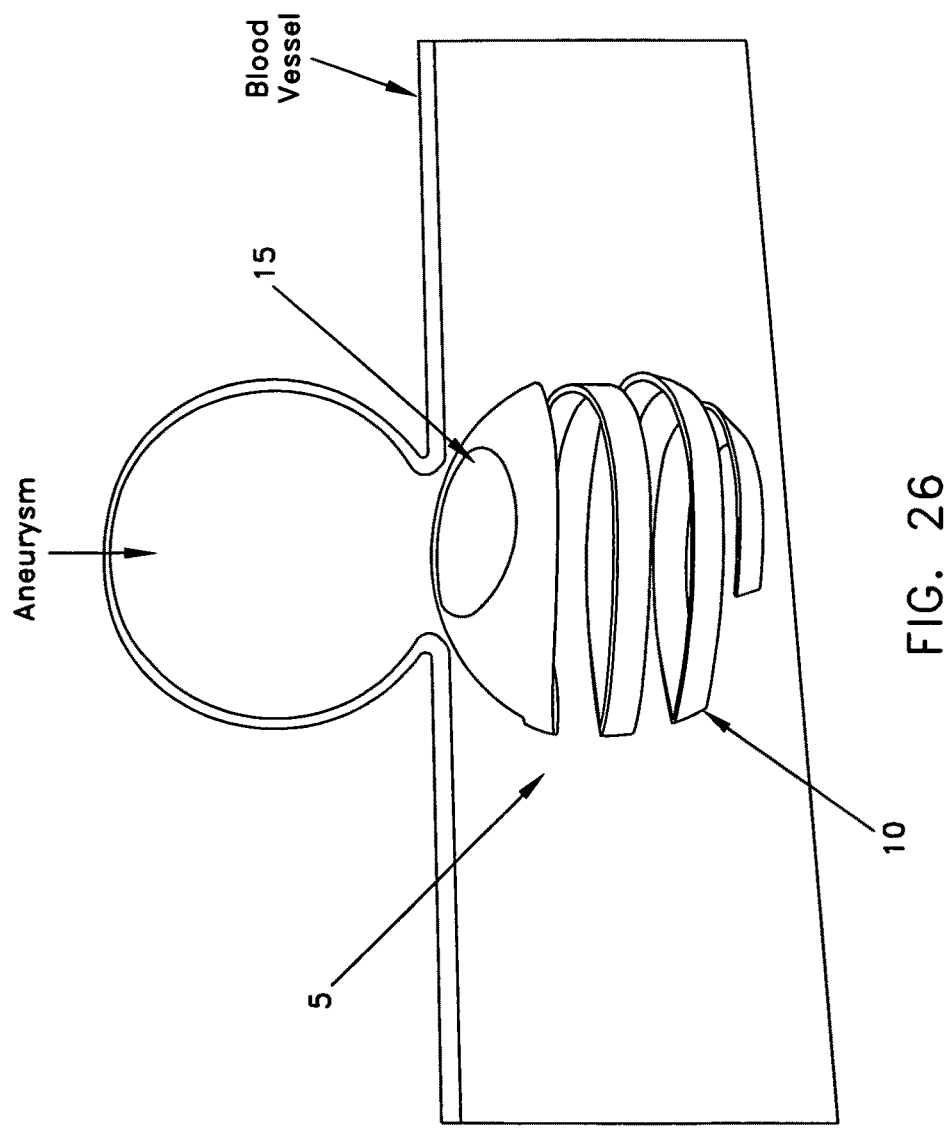
FIG. 26 is a schematic view showing another novel expandable spherical structure formed in accordance with the present invention, wherein the expandable spherical structure comprises an open frame with a flow-restricting face (i.e., a closed face in this particular embodiment), and wherein the open frame of the expandable spherical structure comprises a spherical spiral.

Thus, for example, open frame 10 may be formed with a spherical spiral structure, e.g., such as is shown in FIG. 26, where a spiral strut forms the open frame 10.

Figure 27:
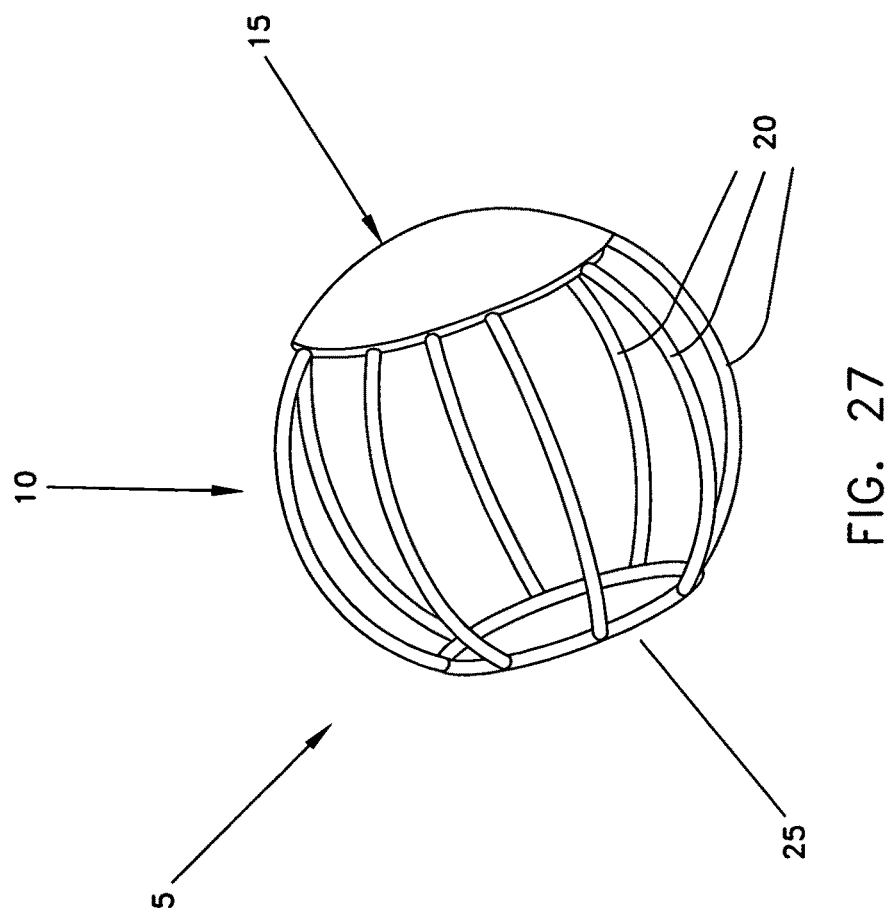
FIG. 27 is a schematic view showing another novel expandable spherical structure formed in accordance with the present invention, wherein the expandable spherical structure comprises an open frame with a flow-restricting face (i.e., a closed face in this particular embodiment), and wherein the open frame of the expandable spherical structure comprises a spherical cage.
Figure 28:
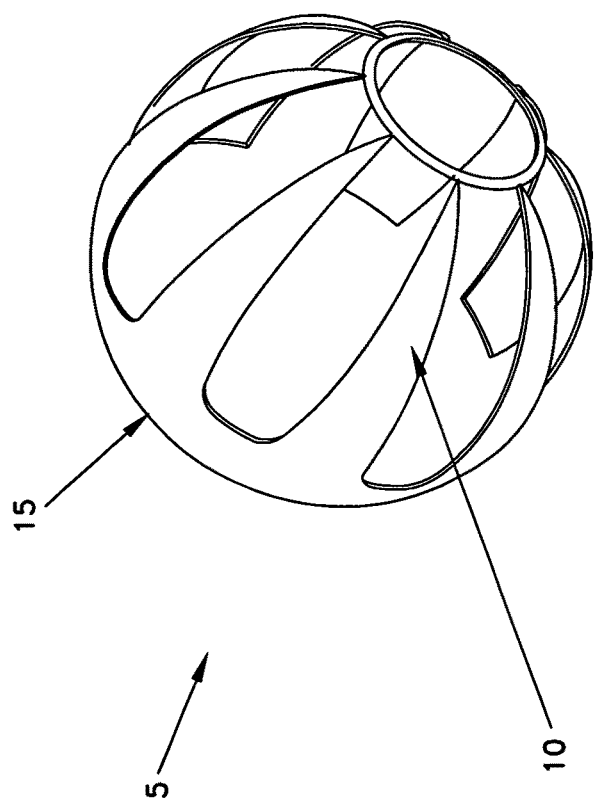
FIGS. 28-37 are schematic views showing other novel expandable spherical structures formed in accordance with the present invention, wherein the expandable spherical structures comprise spherical cages.
Figure 29:
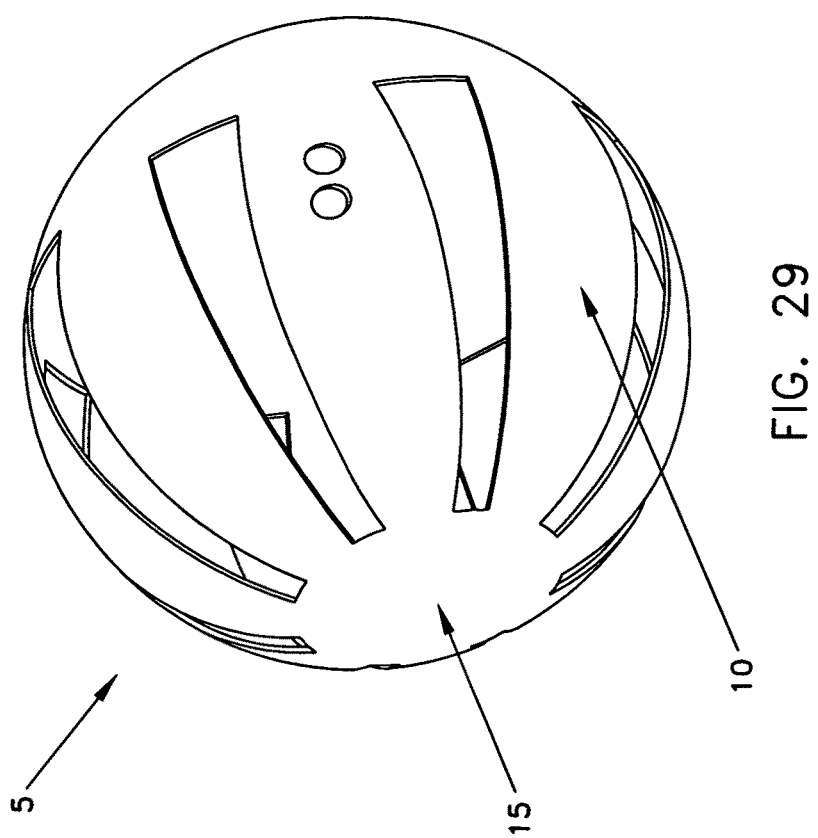
Figure 30:
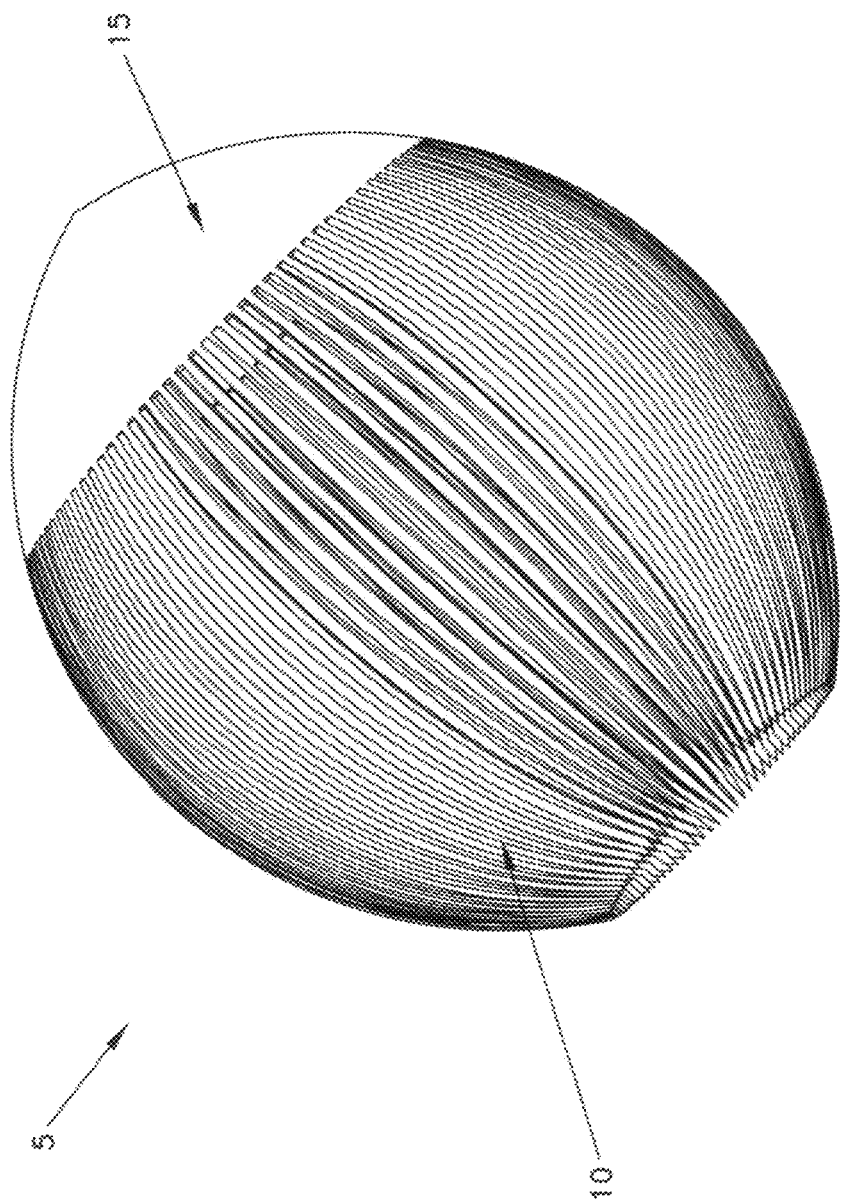
Figure 31:
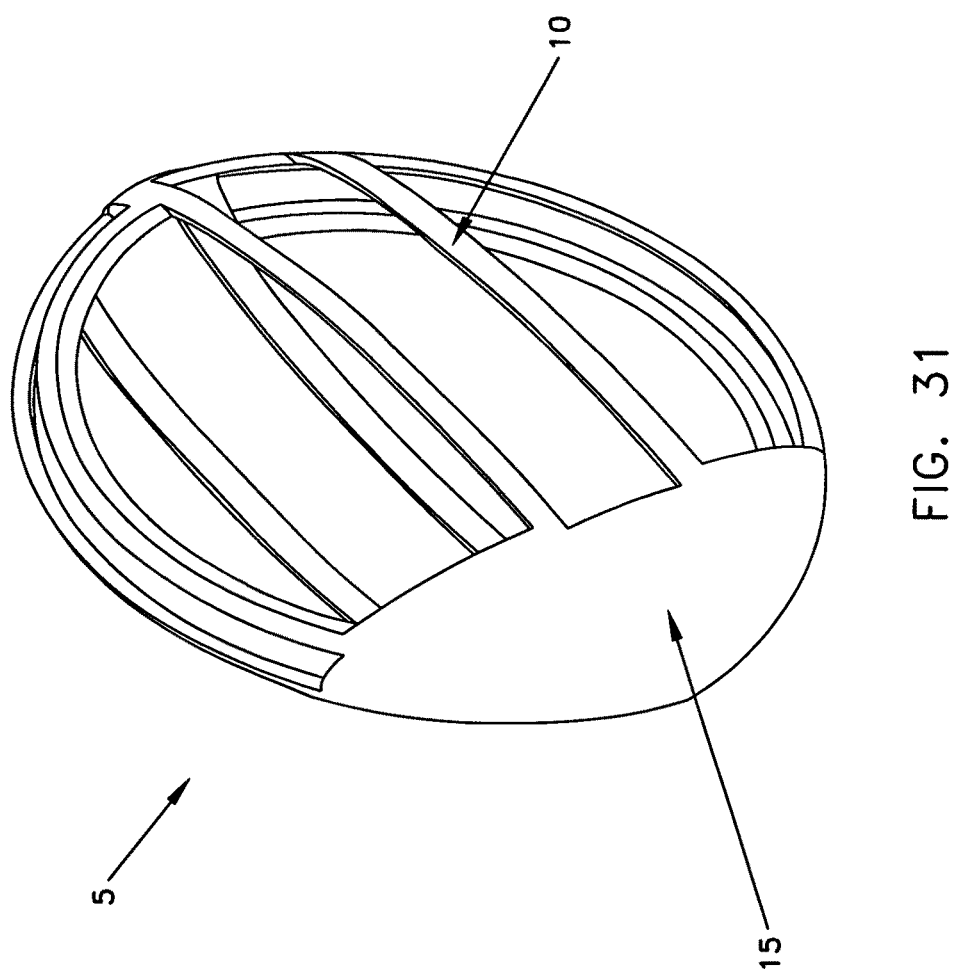
Figure 32:
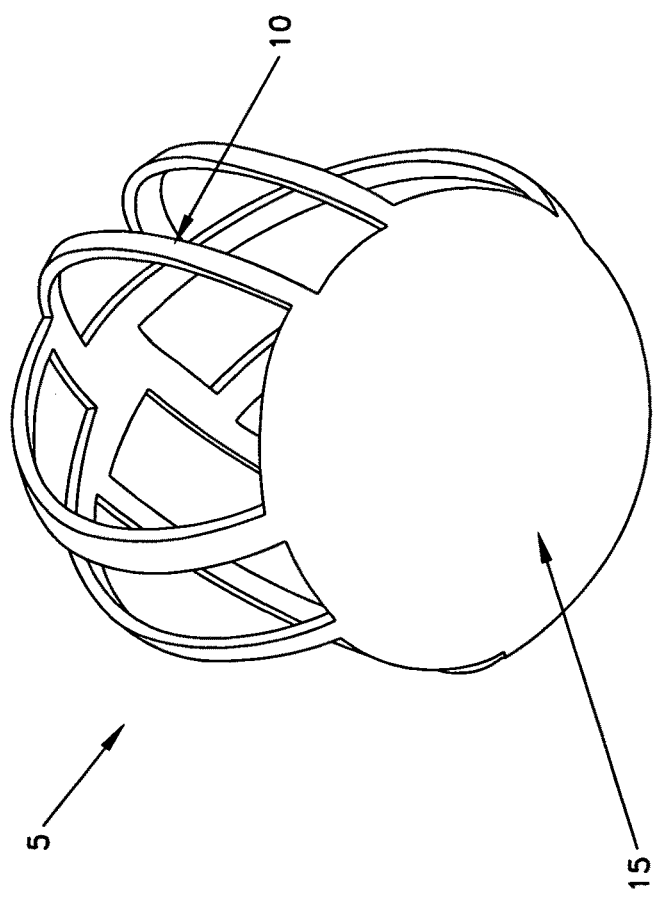
Figure 33:
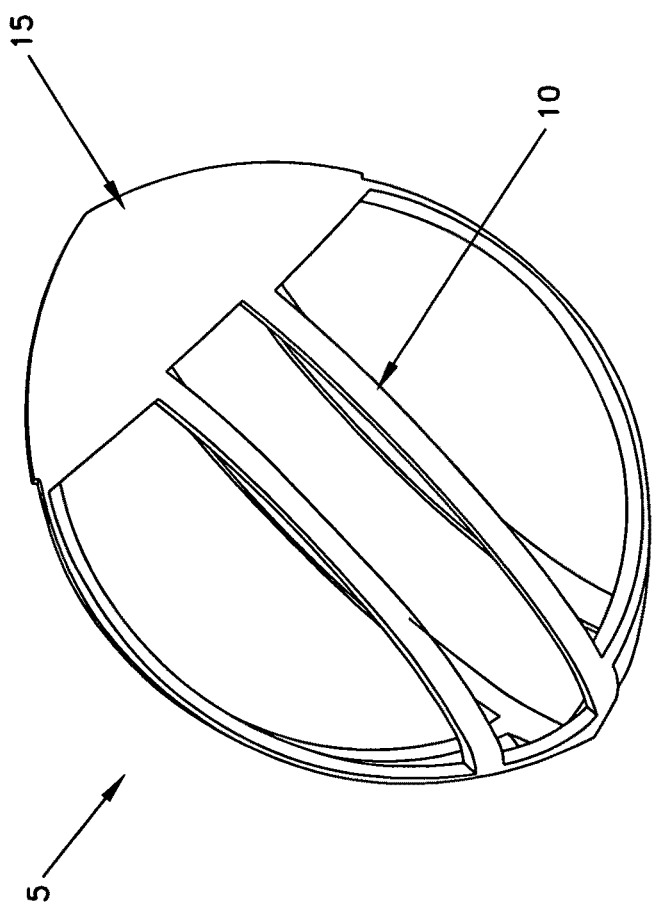
Figure 34:
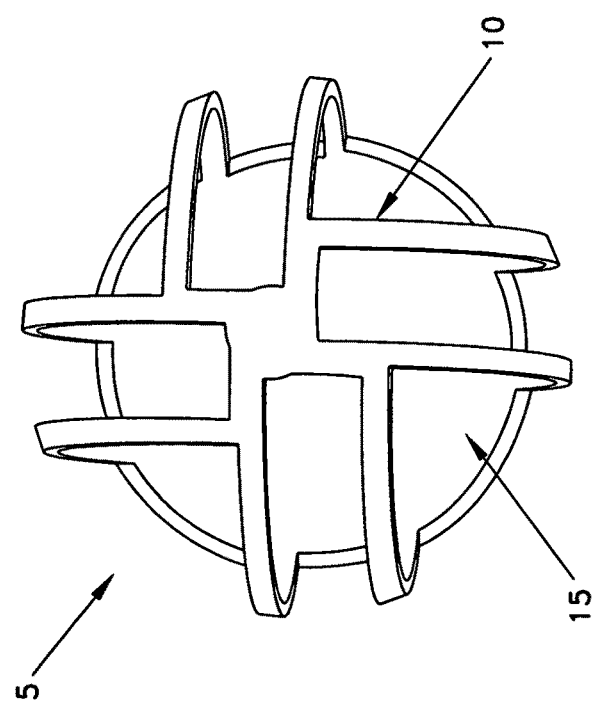
Figure 35:
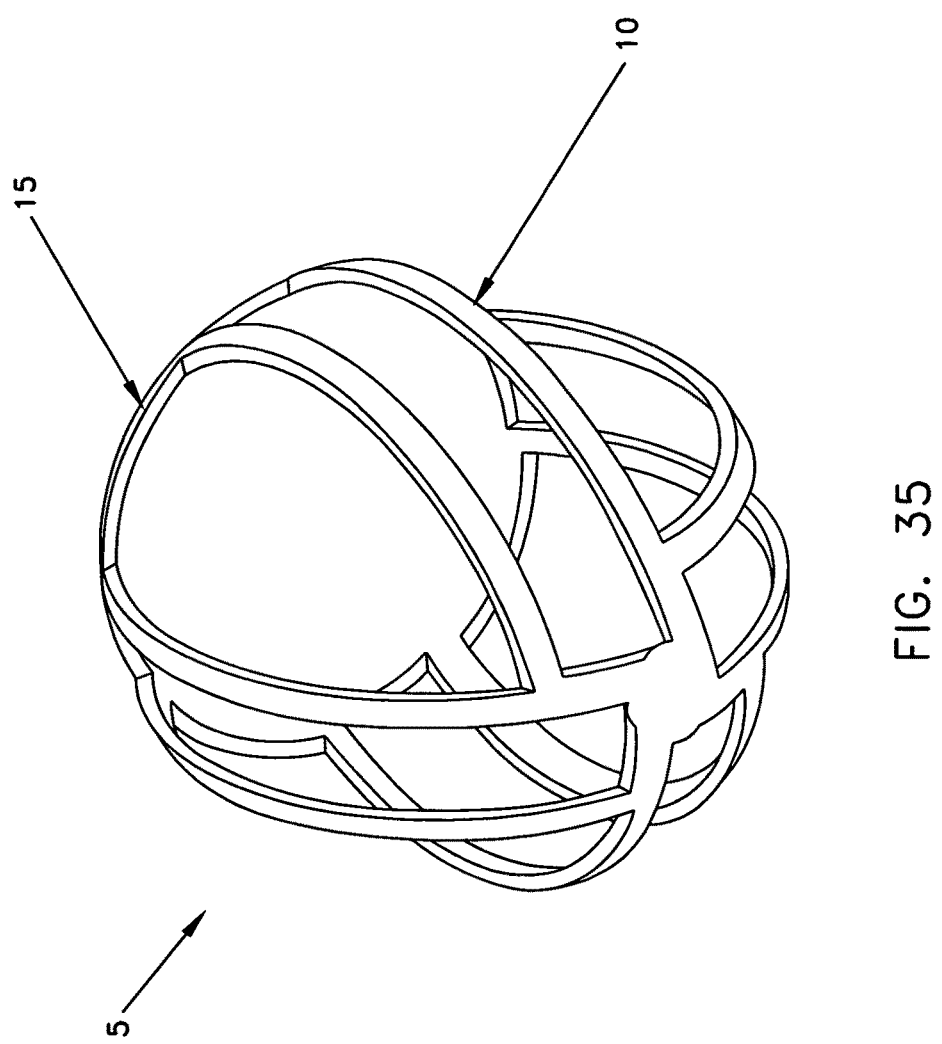
Figure 36:
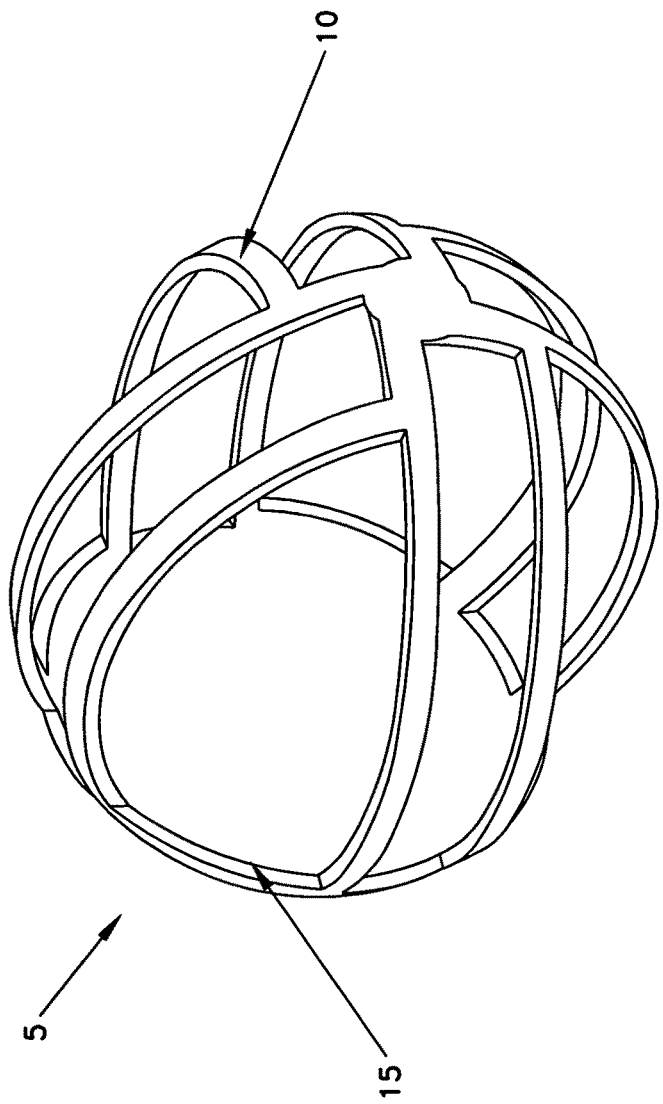
Figure 37:
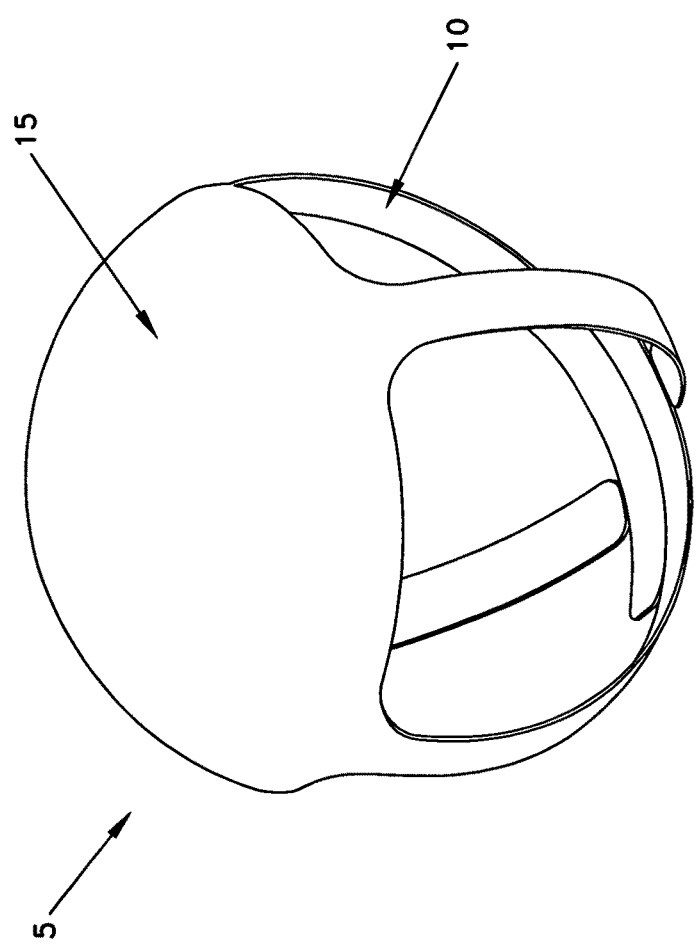

FIG. 27 shows an open frame 10 having a spherical cage structure. More particularly, in this construction, open frame 10 comprises a plurality of axially-aligned struts 20 which extend between flow-restricting face 15 and an annular ring 25. Struts 20 preferably bow outwardly when open frame 10 is in its expanded configuration, but may be bent inwardly (e.g., to a straight or inwardly-bowed configuration) or otherwise deformed so as to permit open frame 10 to assume a reduced configuration. By way of example but not limitation, struts 20 may be bent inwardly (e.g., so as to extend substantially parallel to one another) when open frame 10 is in its reduced configuration.

FIGS. 28-37 show other spherical cage constructions wherein various struts 20 form open frame 10.

Figure 38:
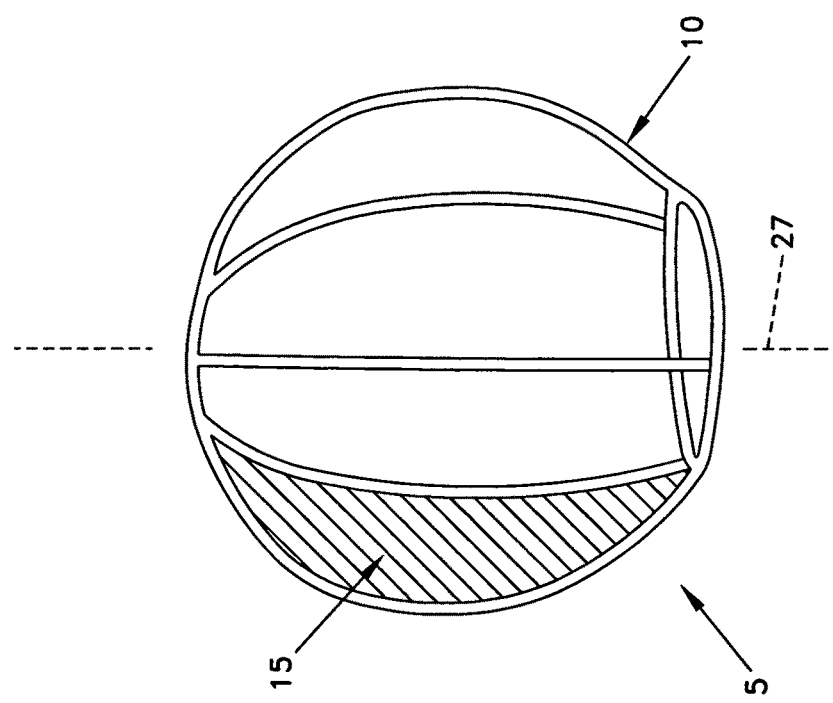
FIGS. 38-43 are schematic views showing other novel expandable spherical structures formed in accordance with the present invention, wherein the expandable spherical structure comprises an open frame with a flow-restricting face (i.e., a closed face in this particular embodiment), and wherein the flow-restricting face is disposed to one side of the axis of approach.
Figure 39:
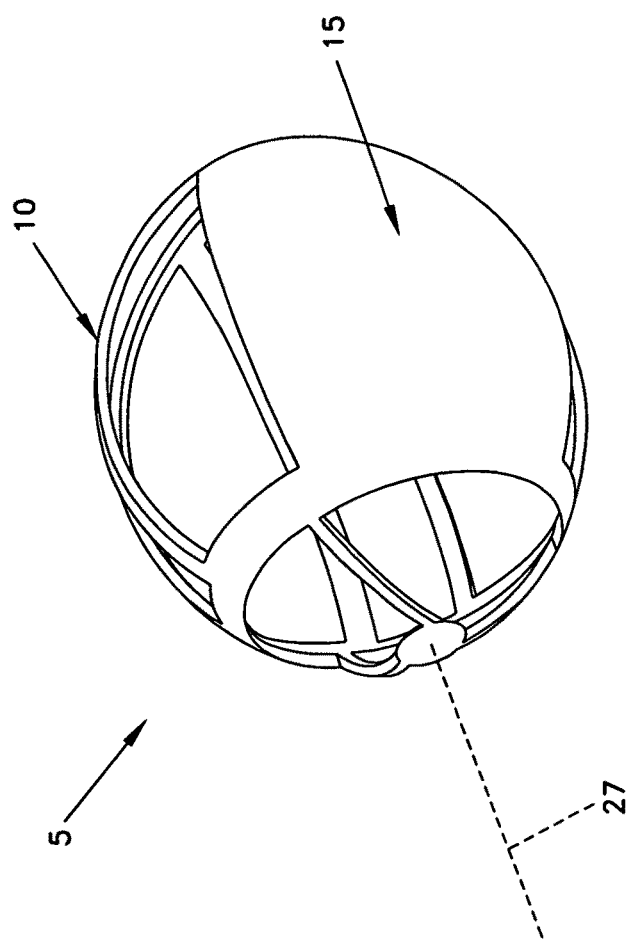
Figure 41:
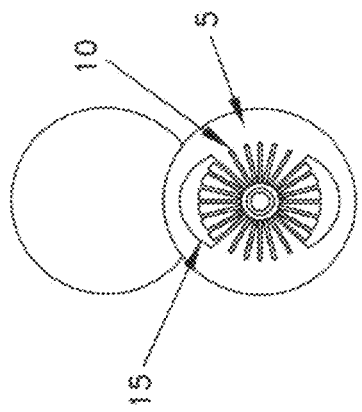
Figure 43:
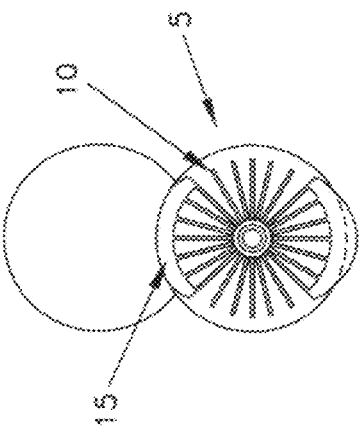
Figure 40:
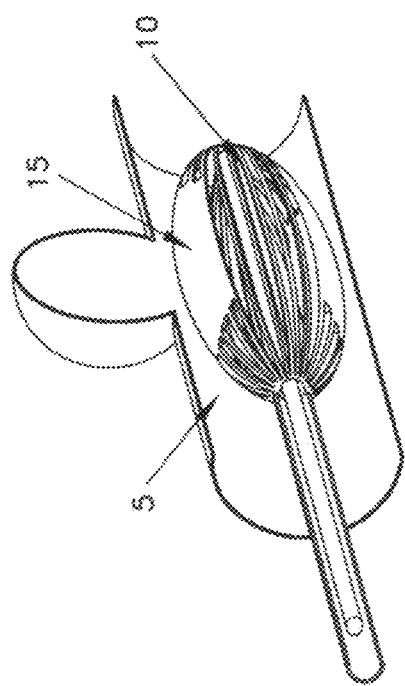
Figure 42:
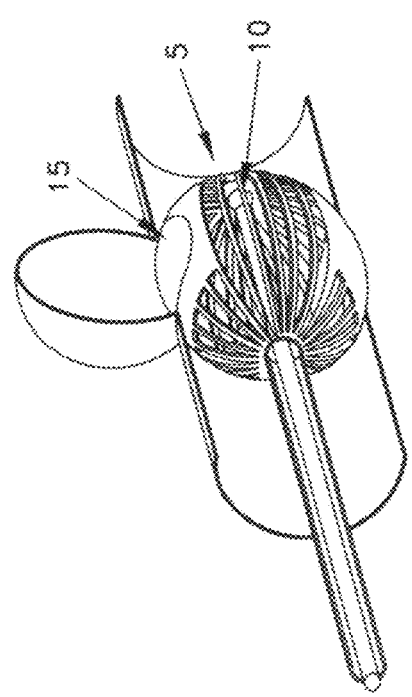
Figure 50:
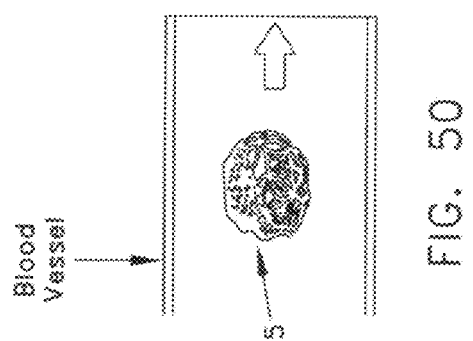
FIGS. 50-54 are schematic views showing another novel expandable spherical structure formed in accordance with the present invention, wherein the expandable spherical structure comprises an open frame with a flow-restricting face (i.e., a face having a high strut density in this particular embodiment), and wherein the expandable spherical structure is shown being used to restrict flow to a lateral aneurysm in a blood vessel.
Figure 51:
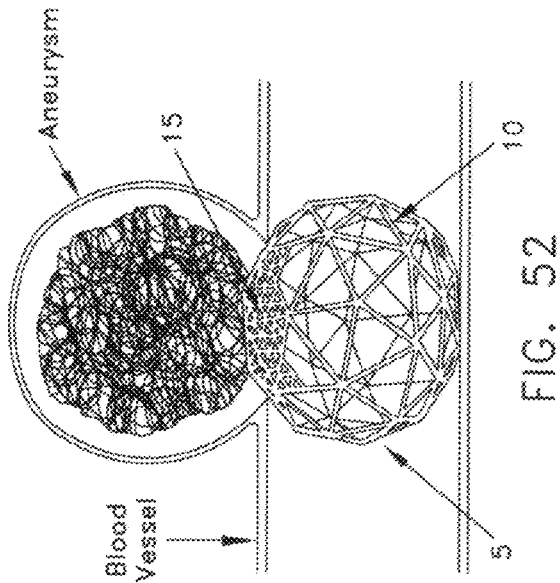
Figure 52:
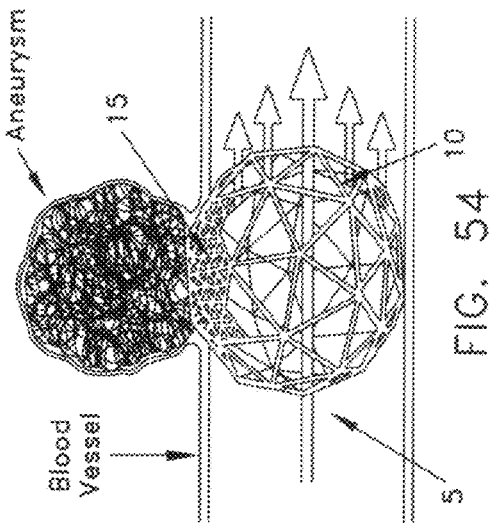
Figure 53:
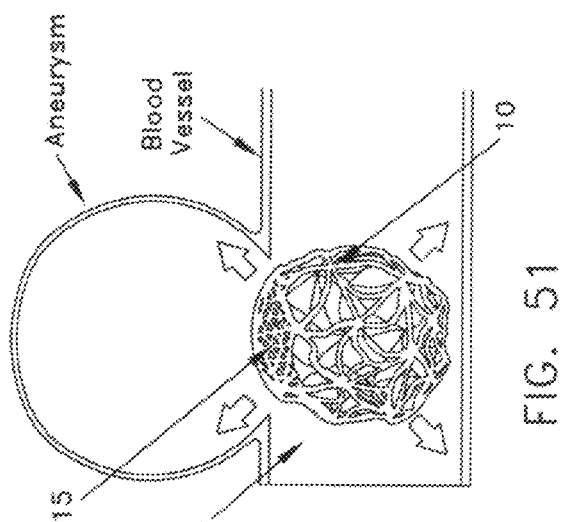
Figure 54:
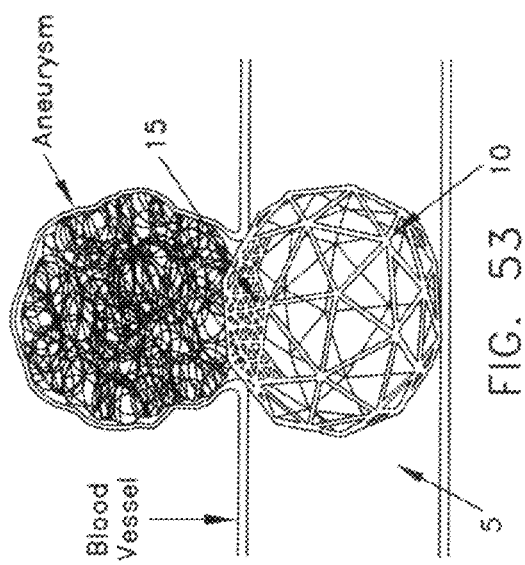
Figure 55:
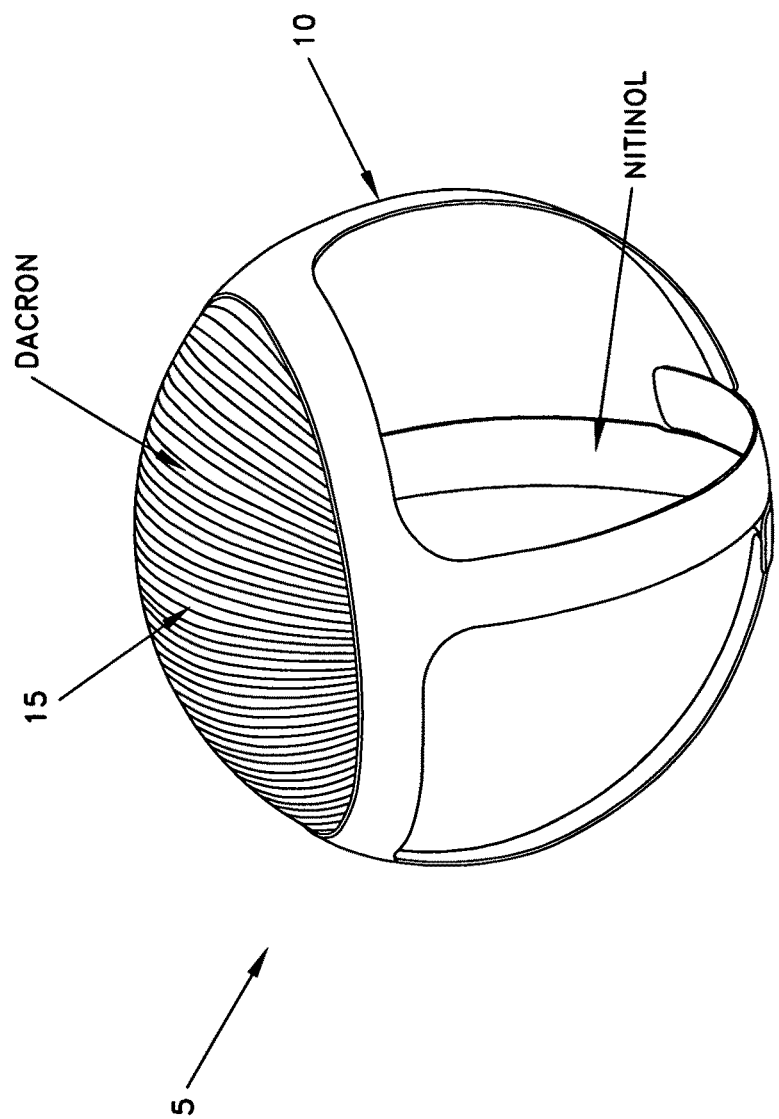
FIGS. 55-63 are schematic views showing other expandable spherical structures formed in accordance with the present invention, wherein the expandable spherical structures comprise open frames with flow-restricting faces (i.e., faces having high strut densities in these particular embodiments)
Figure 56:
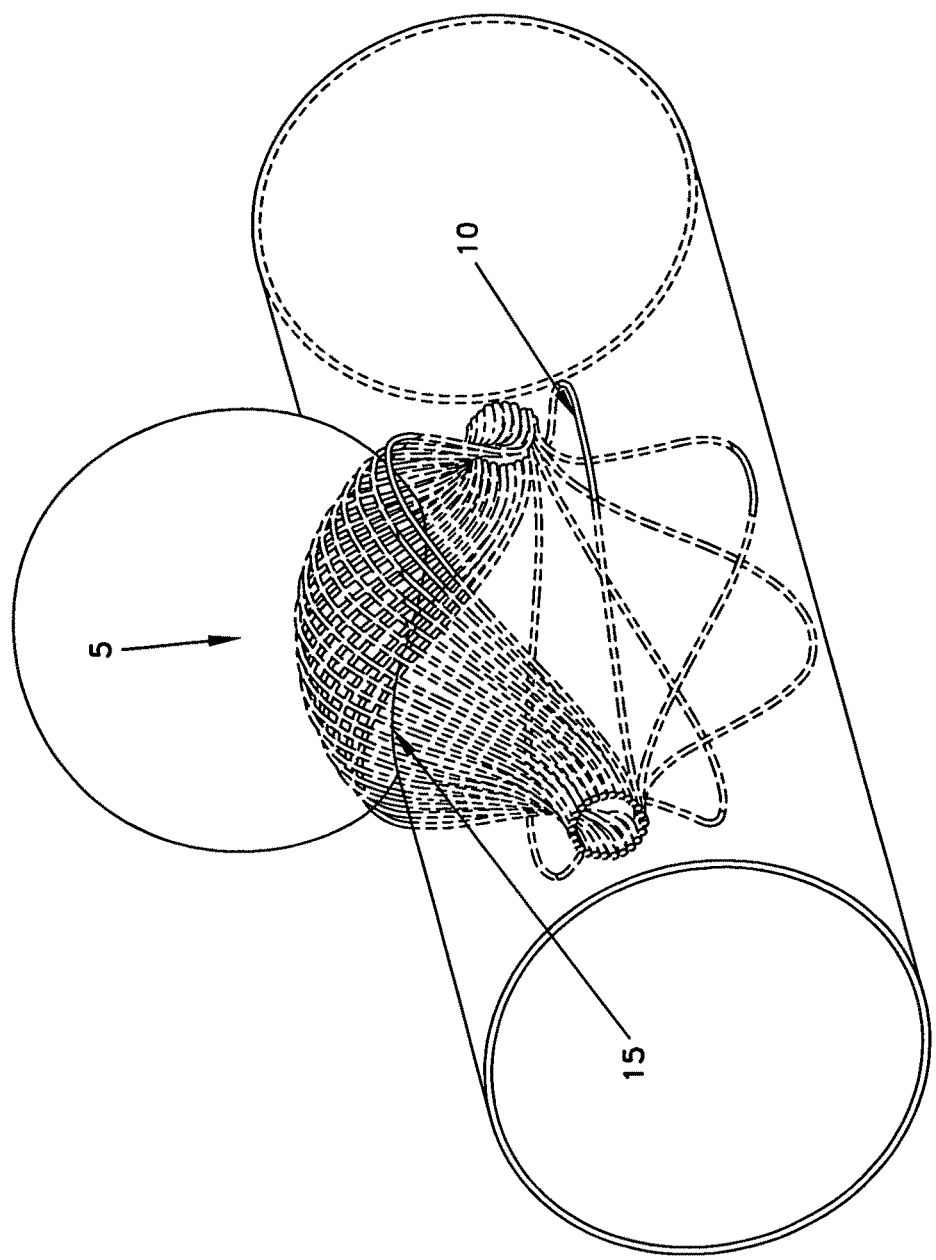
Figure 57:
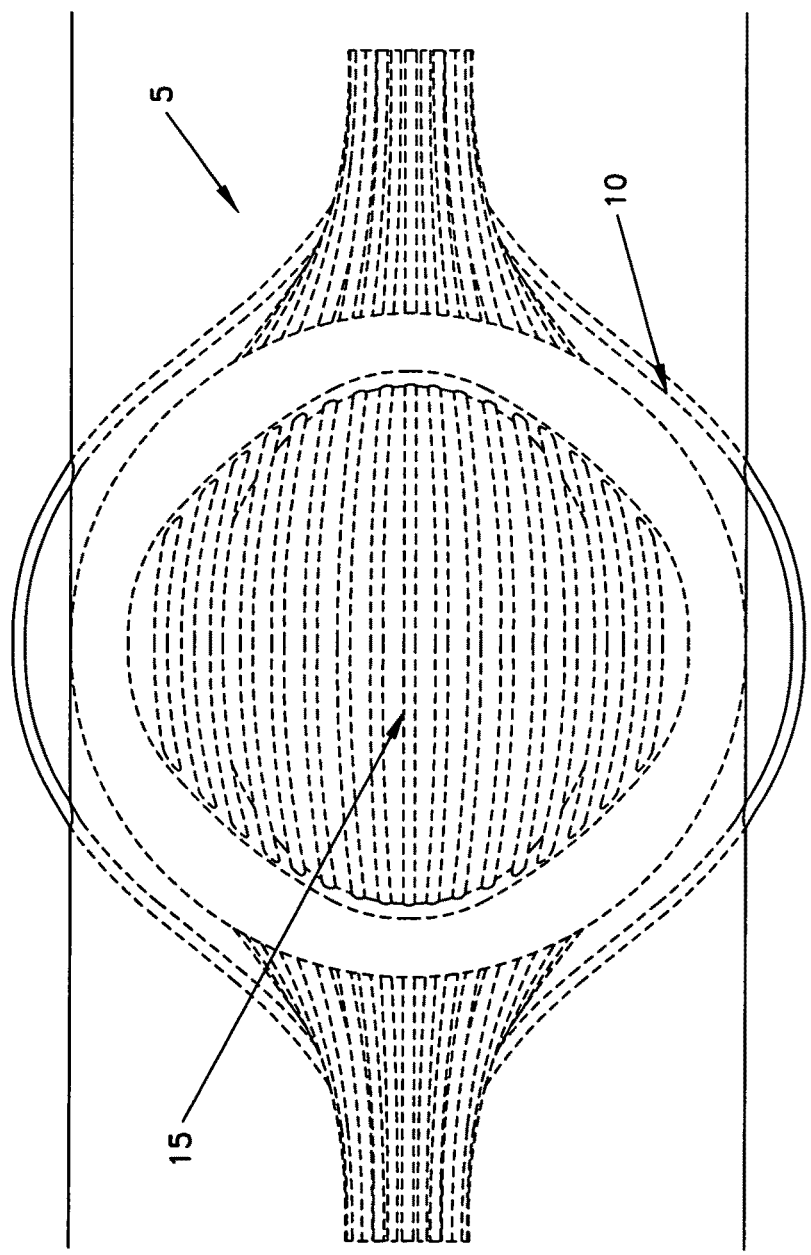
Figure 58:
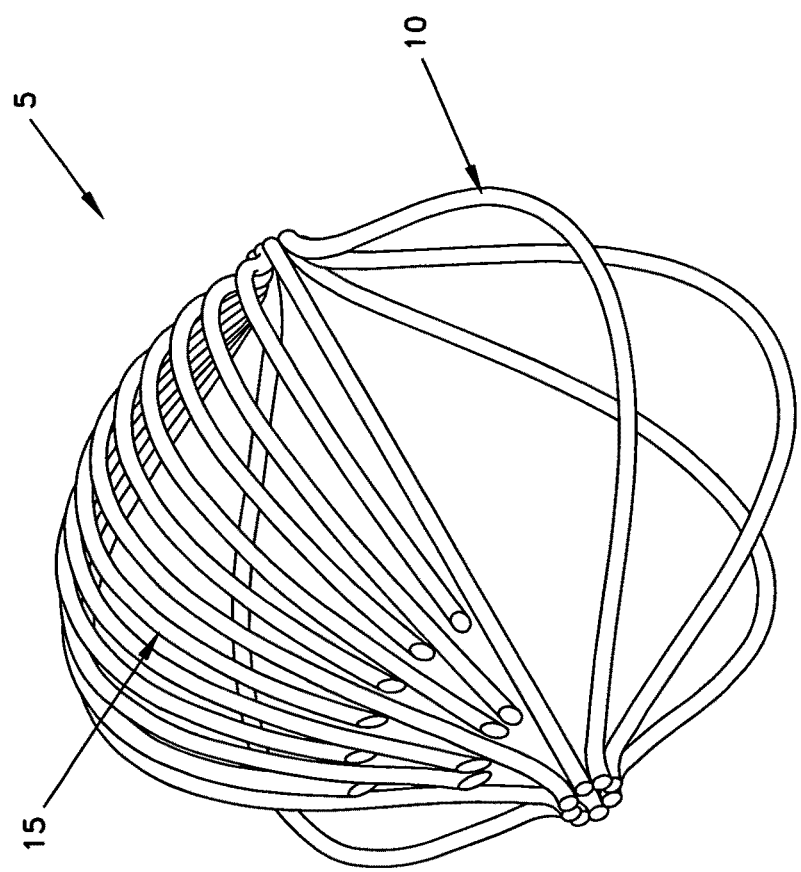
Figure 59:
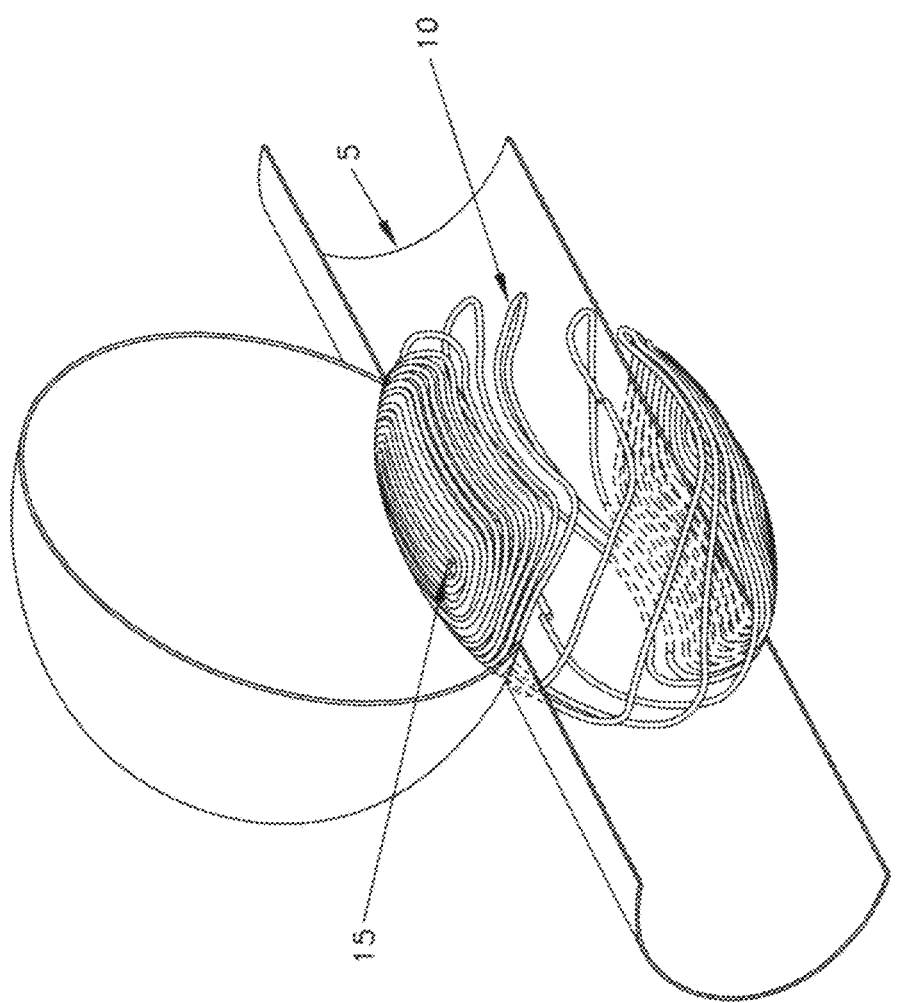
Figure 60:
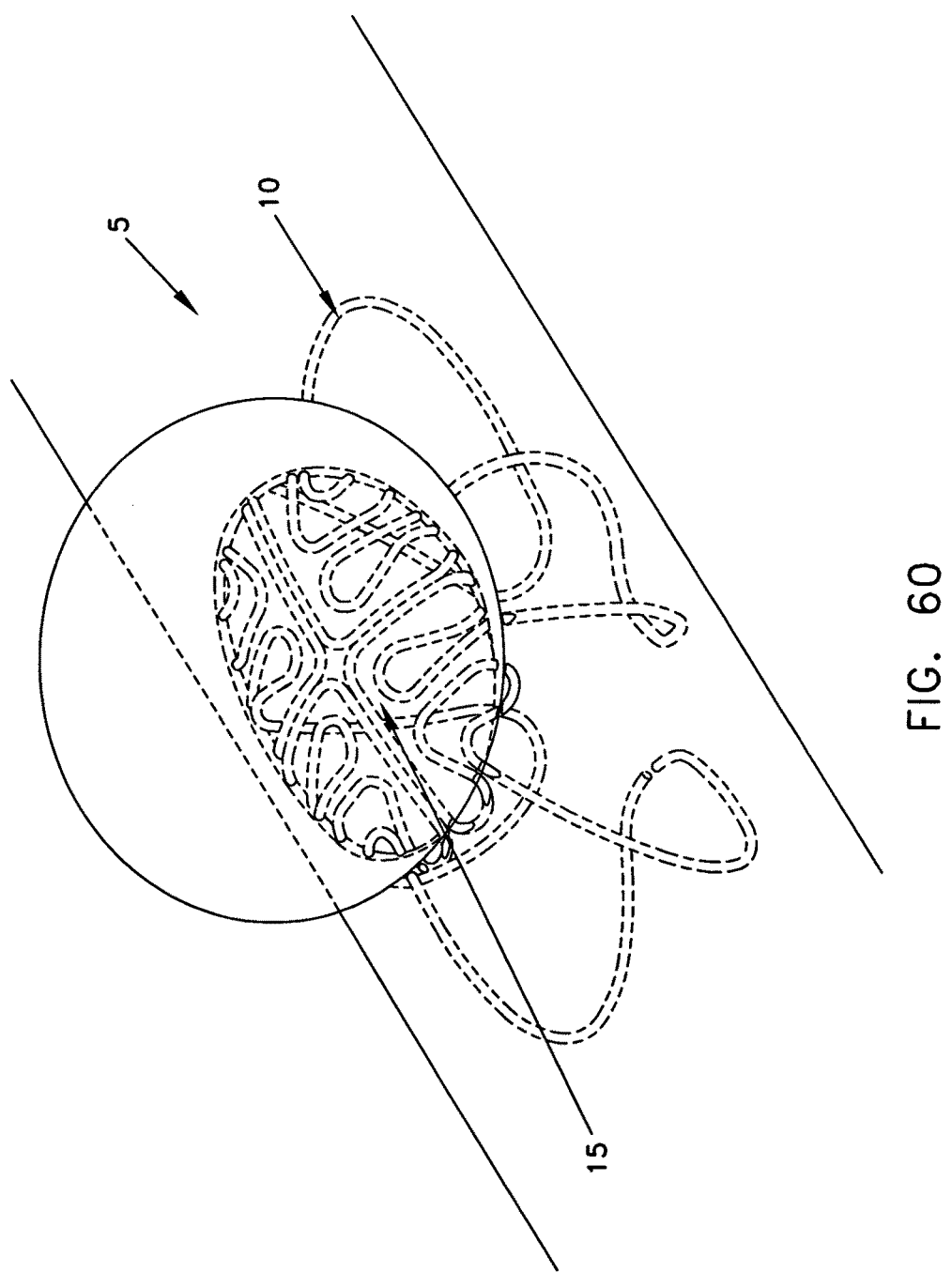
Figure 61:
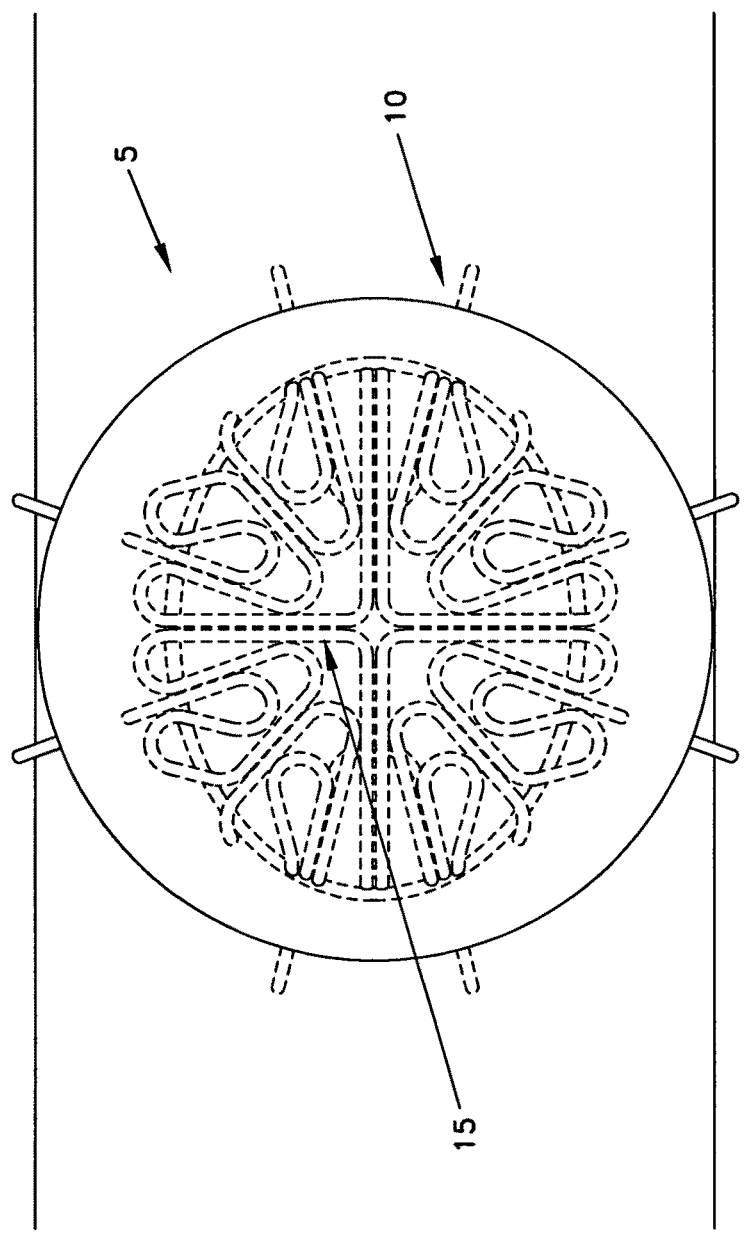
Figure 62:
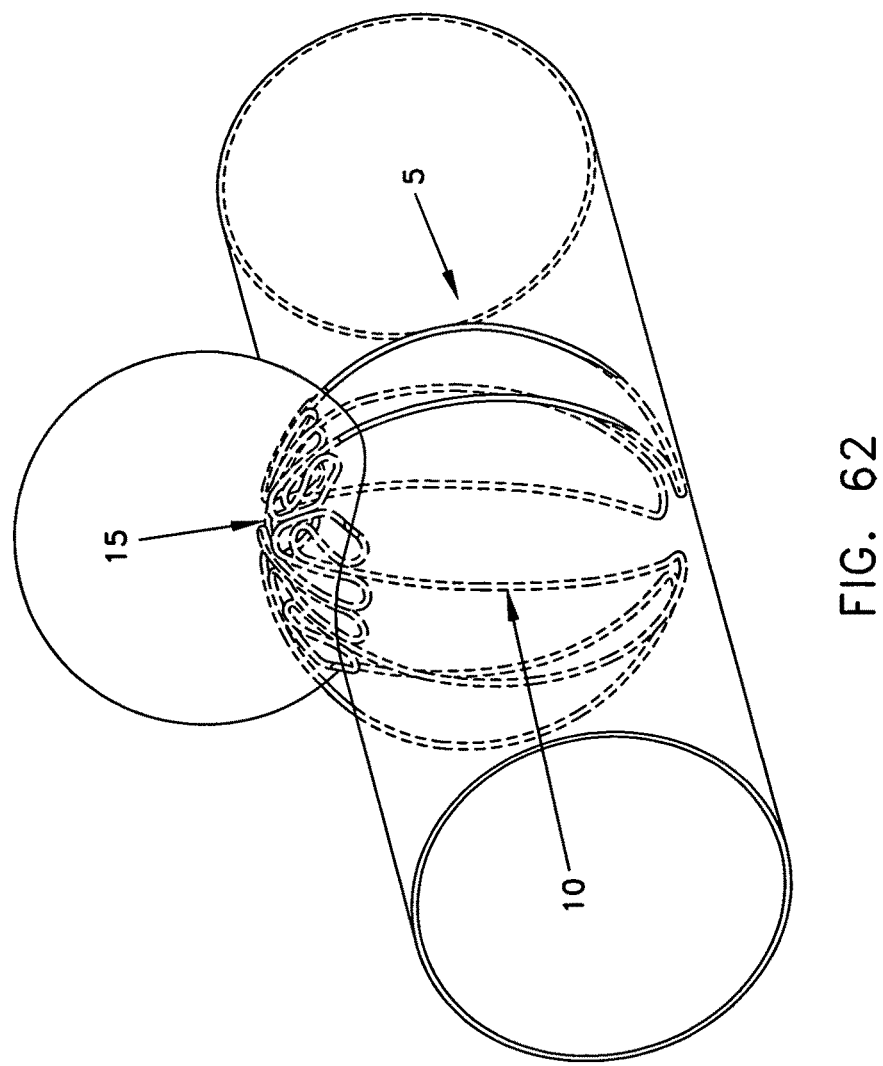

It will be appreciated that, with the construction shown in FIG. 27, flow-restricting face 15 sits at one end of the plurality of axially-aligned struts 20 and annular ring 25 sits at the opposing end of the plurality of axially-aligned struts 20. Since struts 20 are intended to be bowed inwardly so that the expandable spherical structure can assume a reduced configuration, the spherical cage structure of FIG. 27 is generally intended to be delivered axially, with flow-restricting face 15 leading. Thus, this construction is particularly well suited for use with bifurcation aneurysms, where the neck of the aneurysm is typically axially-aligned with the direction of approach (see, for example, FIGS. 14-18 and 19-23). Accordingly, where the spherical cage structure is intended to be used with lateral aneurysms, it may be desirable to use the spherical cage configuration shown in FIG. 38, where flow-restricting face 15 is disposed to one side of the axis of approach, i.e., to one side of the axis 27 shown in FIG. 38. In other words, where the spherical cage structure is intended to be used with a bifurcation aneurysm, flow-restricting face 15 is intended to be aligned with the axis of approach, and where the spherical cage structure is intended to be used with a lateral aneurysm, flow-restricting face 15 is intended to be disposed to one side of the axis of approach. In this way, expandable spherical structure 5 can be endoluminally advanced to the therapy site and flow-restricting face 15 properly positioned relative to the anatomy.

FIGS. 39-43 show other spherical cage constructions wherein various struts 20 form open frame 10 and flow-restricting face 15 is disposed to one side of the axis of approach.

Installation Tools

Various installation tools may be provided to deploy expandable spherical structure 5 within a blood vessel or other body lumen.

Thus, for example, in FIG. 44, there is shown a syringe-type (e.g., an outer sleeve with an internal pusher) installation tool 100 for deploying the expandable spherical structure 5 shown in FIG. 45. Installation tool 100 generally comprises a hollow sleeve 105 having a lumen 110 therein, and a pusher 115 slidably disposed within lumen 110. Lumen 110 is sized so that it can accommodate expandable spherical structure 5 when the expandable spherical structure is in its reduced configuration (FIG. 44), but not when it is in its enlarged configuration (FIG. 45). As a result of this construction, expandable spherical structure 5 may be positioned within lumen 110 (distal to pusher 115) when expandable spherical structure 5 is in its reduced configuration, advanced to the therapy site while within sleeve 105, and then installed at the therapy site by advancing pusher 115 so that expandable spherical structure 5 is ejected from the interior of sleeve 105. Once expandable spherical structure 5 has been ejected from sleeve 105, expandable spherical structure 5 can return to an expanded configuration (FIG. 45) so as to be securely engaged in the blood vessel or other body lumen in the manner previously described, with flow-restricting face 15 pressed against a side wall of the blood vessel or other body lumen. It will be appreciated that the syringe-type installation tool 100 is particularly advantageous where expandable spherical structure 5 is elastically deformable, such that sleeve 105 can serve to mechanically restrain the expandable spherical structure in its reduced configuration while the expandable spherical structure is within sleeve 105, and release that mechanical constraint when the expandable spherical structure is ejected from sleeve 105.

As noted above, expandable spherical structure 5 of FIGS. 27, 44 and 45 is well suited for use with bifurcation aneurysms, where the neck of the aneurysm is typically axially-aligned with the direction of approach (see, for example, FIGS. 14-18 and 19-23). Where the spherical cage structure is intended to be used with lateral aneurysms, it may be desirable to use the spherical cage configuration shown in FIG. 38, where flow-restricting face 15 is disposed to one side of the axis of approach.

If desired, installation tool 100 can be provided with a gripper mechanism to releasably secure expandable spherical structure 5 to installation tool 100, e.g., so as to releasably secure expandable spherical structure 5 to installation tool 100 until after expandable spherical structure 5 has been advanced to the therapy site and has returned to its enlarged configuration, so that it is ready to be left at the therapy site. This gripper mechanism ensures complete control of expandable spherical structure 5 as it is moved out of the installation tool and erected within the body, and also facilitates more precise positioning (e.g., with proper rotation, etc.) of the expandable structure against the side wall of the body lumen.

More particularly, and looking now at FIG. 46, installation tool 100 may be provided with a plurality of spring grippers 125. Spring grippers 125 are disposed within lumen 110 of sleeve 105, exterior to pusher 115. Each spring gripper 125 is formed so that when a bowed portion 130 of the spring gripper is restrained within lumen 110, a hook portion 135 of that spring gripper holds annular ring 25 of expandable spherical structure 5 to the distal end of pusher 115. However, when pusher 115 is advanced to the point where bowed portion 130 of spring gripper 125 is no longer restrained within lumen 110, hook portion 135 of spring gripper 125 moves outboard so as to release annular ring 25 of expandable spherical structure 5 from the distal end of pusher 115. Thus it will be seen that spring grippers may be used to releasably secure expandable spherical structure 5 to installation tool 100 until after the expandable spherical structure has been advanced out of the distal end of the installation tool and returned to its enlarged configuration. This arrangement can provide the clinician with increased control as expandable spherical structure 5 is deployed within the blood vessel.

As noted above, expandable spherical structure 5 of FIGS. 27 and 44-46 is well suited for use with bifurcation aneurysms, where the neck of the aneurysm is typically axially-aligned with the direction of approach (see, for example, FIGS. 14-18 and 19-23). Where the spherical cage structure is intended to be used with lateral aneurysms, it may be desirable to use the spherical cage configuration shown in FIG. 38, where closed face 15 is disposed to one side of the axis of approach.

If desired, installation tool 100 can be provided with an expansion balloon for expanding the expandable spherical structure from its reduced configuration to its enlarged configuration. More particularly, and looking now at FIGS. 47-49, installation tool 100 may be provided with sleeve 105 and pusher 115 as discussed above. In addition, installation tool 100 may be provided with an expansion balloon 140. Expansion balloon 140 is supported on an inflation rod 145 which is movably disposed within pusher 115. Expansion balloon 140 is (in its deflated condition) disposed internal to open frame 10 of expandable spherical structure 5. As a result of this construction, installation tool 100 may receive expandable spherical structure 5 while the expandable spherical structure is in its reduced configuration, carry the expandable spherical structure to the desired therapy site, position the expandable spherical structure at the desired location, and then expand expansion balloon 140 so as to open the expandable spherical structure to its enlarged configuration. Expansion balloon 140 may then be deflated and withdrawn from the interior of expandable spherical structure 5. It will be appreciated that providing installation tool 100 with an expansion balloon may be advantageous where expandable spherical structure 5 does not self-erect within the body lumen.

Expandable Spherical Structure Having a Flow-Restricting Face Formed with a High Strut Density In FIGS. 1-50, flow-restricting face 15 of expandable spherical structure 5 is depicted as a closed face, in the sense that flow-restricting face 15 comprises a substantially complete surface or barrier which is capable of closing off (and/or very significantly reducing flow to) an aneurysm or other opening in the side wall of a blood vessel or other body lumen, and/or for reinforcing a weakness in the side wall of the blood vessel or other body lumen. However, it should be appreciated that for many applications, flow-restricting face 15 need not comprise a substantially complete surface or barrier, i.e., flow-restricting face 15 may be formed with a face having a sufficiently high strut density to form an effectively closed face or to otherwise achieve a desired purpose. Thus, for example, in FIGS. 50-54, there is shown an expandable spherical structure 5 comprising an open frame 10 having a flow-restricting face 15 formed with a high strut density such that blood flow to the aneurysm will be restricted and the aneurysm will thrombose. In this circumstance, flow-restricting face 15 may be considered to be effectively closed. Furthermore, where flow-restricting face 15 is being used to reinforce a weakness in a side wall (as opposed to being used to restrict flow to an opening in a side wall), closed face 15 may have a somewhat lower strut density, since it does not need to significantly restrict the flow of a fluid.

FIGS. 55-63 show other expandable spherical structures 5 wherein flow-restricting face 15 is formed with a sufficiently high strut density to achieve a desired purpose. In this respect it will be appreciated that, as used herein, the term strut is intended to mean substantially any element spaced from an adjacent element or in contact with an adjacent element. Thus, where flow-restricting face 15 is formed by a face having a high strut density, the struts may be in the form of a screen, a mesh, a lattice, a series of parallel or concentric interlaced or otherwise patterned struts, etc.

It should also be appreciated that it is possible to form the entire expandable spherical structure 5 out of a single superelastic wire, e.g., a shape memory alloy constructed so as to form stress-induced martensite at body temperatures. By way of example but not limitation, an appropriately blended and treated Nitinol wire may be used. In this form of the invention, the expandable spherical structure 5 can be (i) deformed into a collapsed configuration wherein a single path of the wire is constrained within a restraining cannula, and (ii) thereafter reformed in situ by simply pushing the wire out of the distal end of the restraining cannula, whereupon expandable spherical structure 5 reforms in the blood vessel or other body lumen. This form of the invention is particularly well suited to constructions where flow-restricting face 15 is formed with a single, patterned strut arranged to have a high strut density, e.g., with a strut density sufficiently high to restrict flow to the mouth of an aneurysm, and/or a strut density sufficiently high to reinforce the side wall of a blood vessel or other body lumen, and/or a strut density sufficiently high to achieve some other desired purpose. See, for example, FIGS. 59-63, which show flow-restricting face 15 formed out of a single, patterned strut, where the strut pattern may comprise one or more of a variety of configurations, e.g., with parallel paths, concentric paths, switchback paths, serpentine paths, etc.

Utilizing the Expandable Spherical Structure in Conjunction with Thrombosis-Inducing Coils As noted above, conventional minimally-invasive techniques for treating brain aneurysms generally involve depositing thrombosis-inducing coils within the dome of the aneurysm. If desired, the expandable spherical structure 5 of the present invention may be used in conjunction with thrombosis-inducing coils, i.e., the thrombosis-inducing coils may be deposited within the dome of an aneurysm after positioning the expandable spherical structure against the mouth of the aneurysm so as to restrict flow into the aneurysm, i.e., by introducing the thrombosis-inducing coils through the face having a high strut density and into the dome of the aneurysm. Alternatively, the thrombosis-inducing coils may be deposited within the dome of the aneurysm before positioning the expandable spherical structure against the mouth of the aneurysm so as to restrict flow into the aneurysm. Significantly, it is believed that this approach will both facilitate thrombosis formation and also prevent coil migration out of the aneurysm.

Deploying the Expandable Spherical Structure within an Aneurysm

It should also be appreciated that expandable spherical structure 5 may be deployed within the body of an aneurysm so that its flow-restricting face 15 confronts the lumen, rather than being within the lumen so that its flow-restricting face confronts the body of the aneurysm. See, for example, FIGS. 64-66, which show the expandable spherical structure 5 of FIGS. 4-8 deployed within the body of the aneurysm. See also, for example, FIGS. 67-71, which show the expandable spherical structure 5 of FIGS. 9-13 being disposed within the body of the aneurysm.

Again, the expandable spherical structure 5 may be positioned within the interior of a lateral aneurysm (FIGS. 64-66 and 67-71) or it may be disposed within a bifurcated aneurysm (FIGS. 72-76 and 77-81).

Expandable Spherical Structure with Stabilizing Legs —"Comet-Shaped Structure"

It is also possible to provide expandable spherical structure 5 with stabilizing legs. Such a construction may be adapted for use with both lateral aneurysms and with bifurcation aneurysms.

Figure 82:
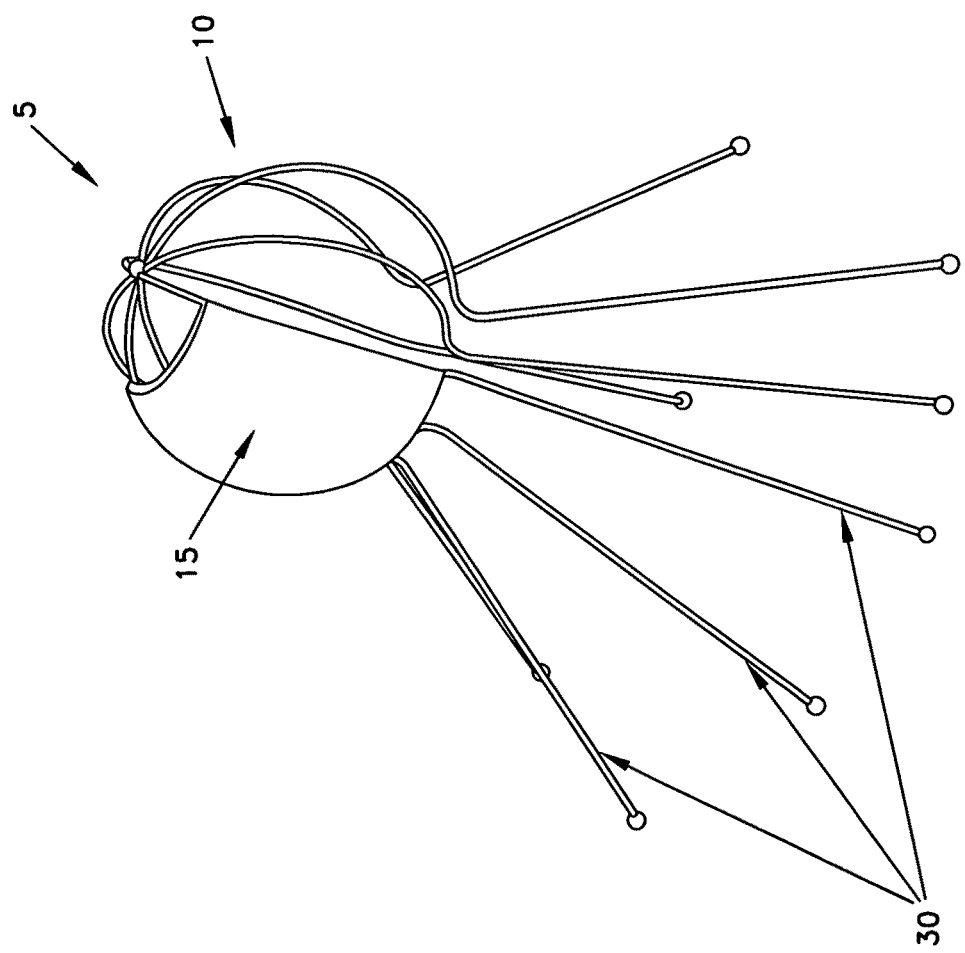
FIGS. 82 and 83 are schematic views showing an expandable spherical structure having stabilizing legs extending therefrom so as to form a "comet-shaped" structure, with the structure being configured to restrict flow to a lateral aneurysm in a blood vessel.
Figure 83:
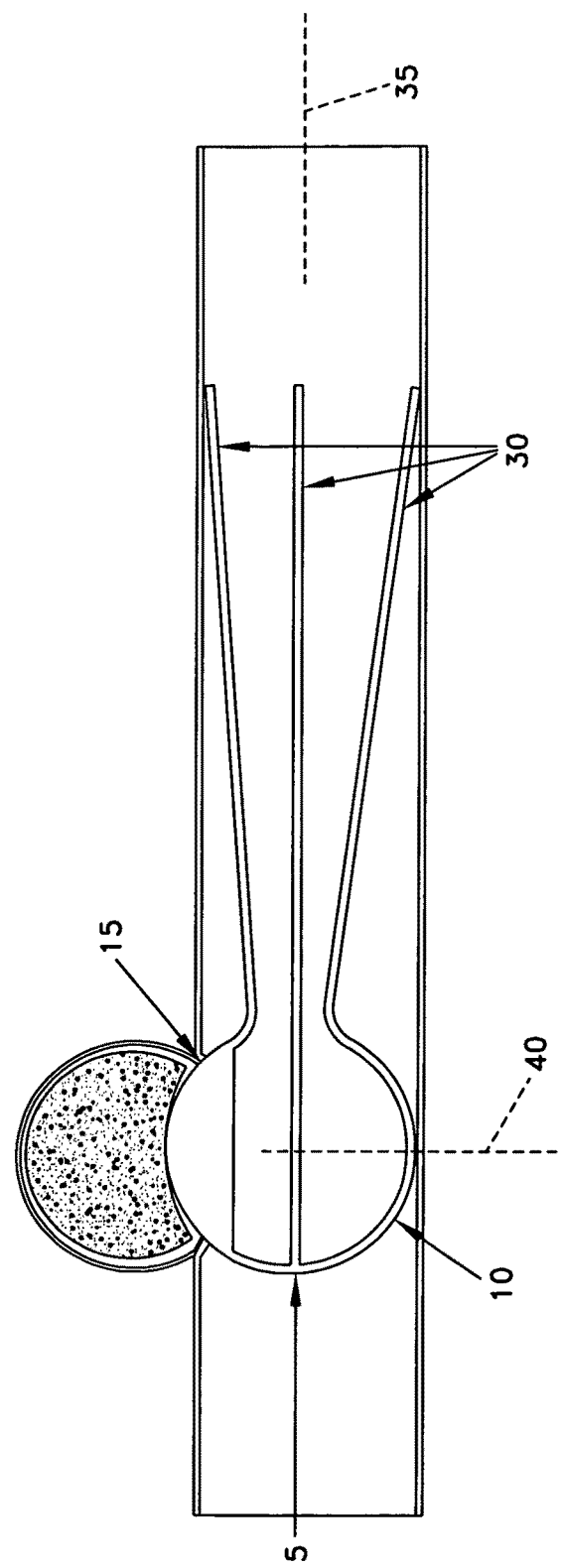

More particularly, and looking now at FIGS. 82 and 83, there is shown an expandable spherical structure 5 which comprises an open frame 10 with a flow-restricting face 15. Extending out of open frame 10 are one or more stabilizing legs 30. Stabilizing legs 30 are formed so that, when flow-restricting face 15 is positioned against the side wall of a blood vessel or other body lumen, stabilizing legs 30 extend endoluminally through the blood vessel or other body lumen. Thus it will be appreciated that the expandable spherical structure 5 shown in FIGS. 82 and 83 is generally intended to be used with a lateral aneurysm, since the center axis 35 of stabilizing legs 30 is set at a right angle to the center axis 40 of flow-restricting face 15 (see FIG. 83).

Preferably, and as seen in FIGS. 82 and 83, stabilizing legs 30 together form a somewhat cone-shaped structure, so that the overall shape of open frame 10 (with flow-restricting face 15) and stabilizing legs 30 is a generally comet-shaped structure.

Figure 84:
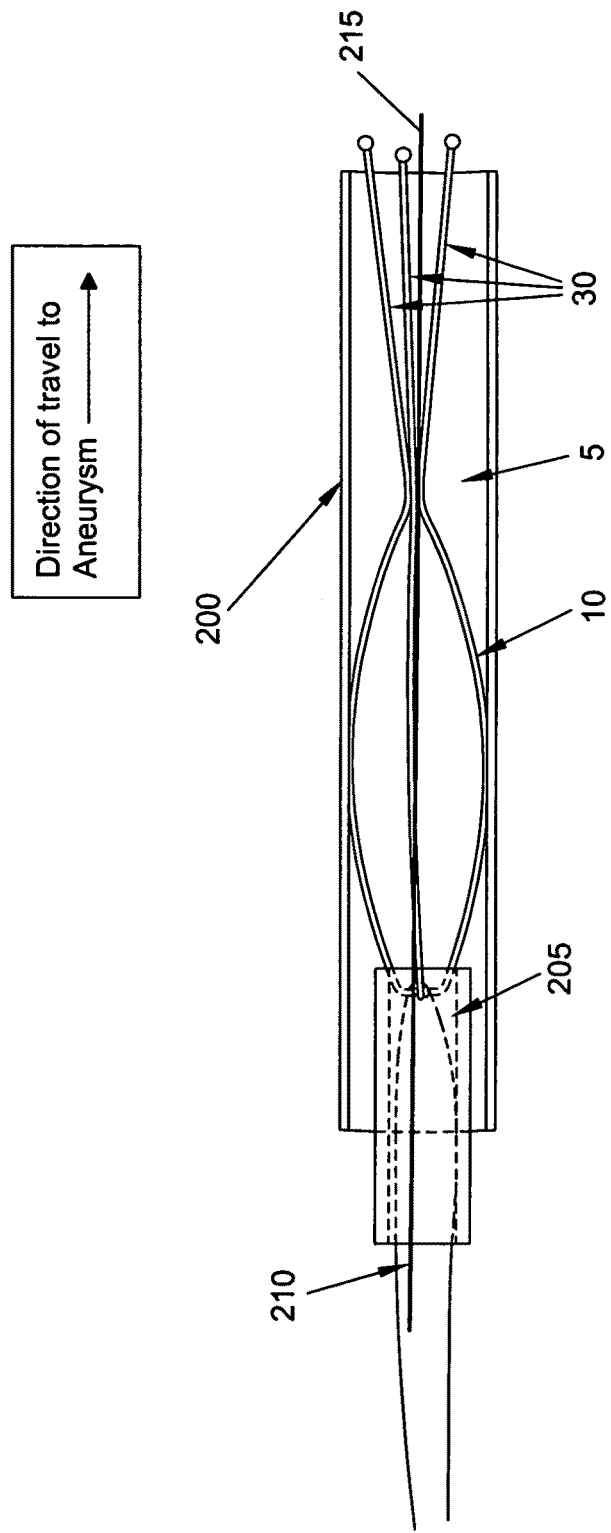

As seen in FIG. 84, this comet-shaped structure may be compressed within a containment sheath 200, with stabilizing legs 30 leading and with open frame 10 (with flow-restricting face 15) trailing, and with a push catheter 205 and tension wire 210 engaging open frame 10 of expandable spherical structure 5. At the aneurysm site, push catheter 205 ejects the comet-shaped structure, "legs first", so that closed face 15 restricts access to the mouth of the aneurysm while stabilizing legs 30 help maintain the position of open frame 10 (and flow-restricting face 15) within the blood vessel. This deployment procedure is preferably conducted over a guidewire 215.

Figure 88:
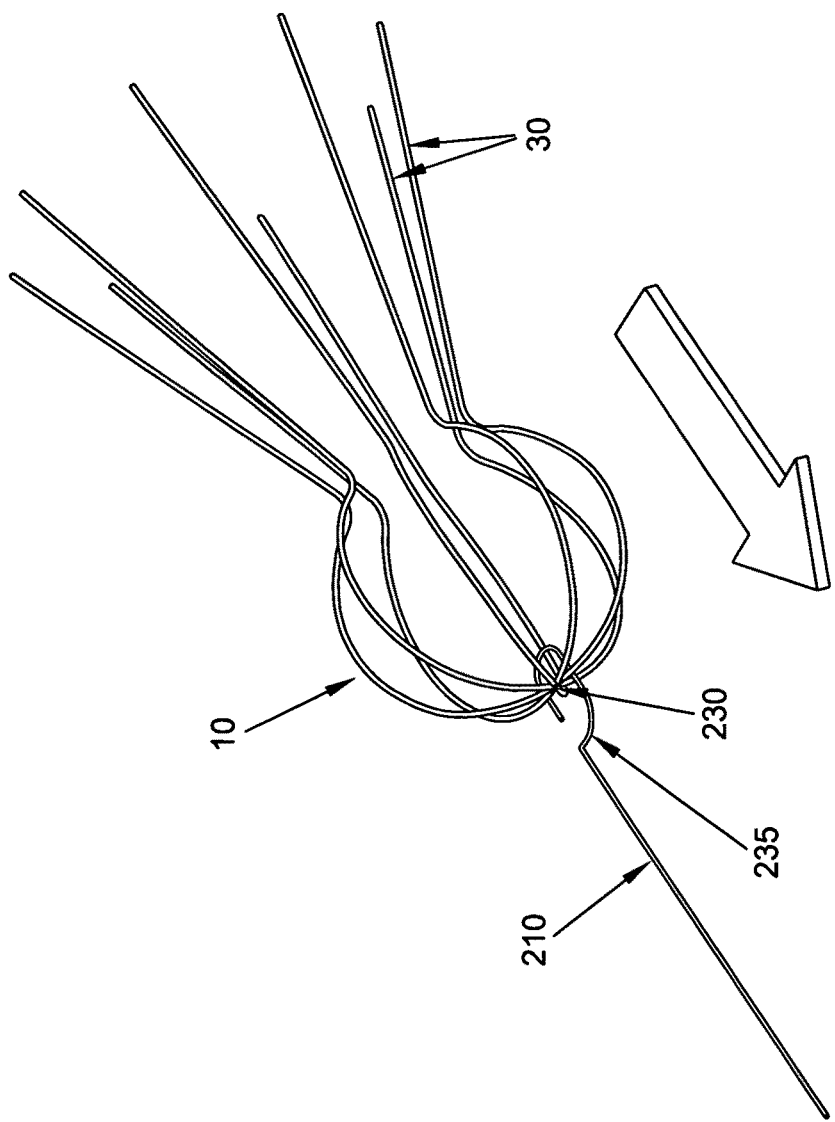
Figure 89:
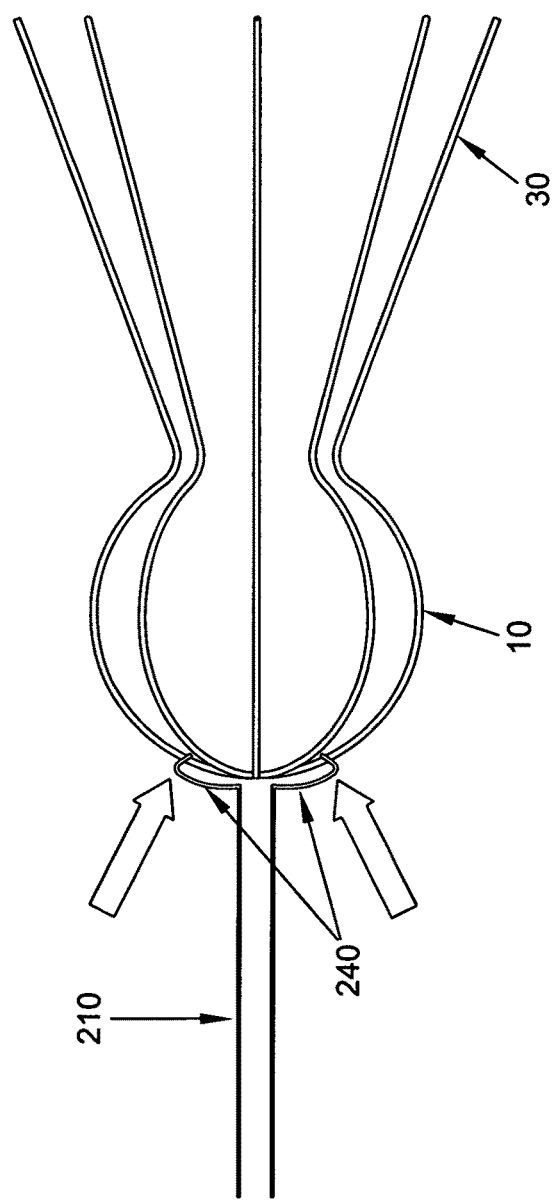

If the comet-shaped structure subsequently needs to be repositioned or removed from a deployment site, tension wire 210 may be used to pull the comet-shaped structure retrograde, e.g., within the blood vessel or all the way back into containment sheath 200. To this end, and looking now at FIGS. 85-87, open frame 10 of expandable spherical structure 5 may comprise a proximal end ring 220, and tension wire 210 may comprise an expandable head 225 adapted to extend through proximal end ring 220 and then expand, whereupon the comet-shaped structure may be moved retrograde. Alternatively, open frame 10 of expandable spherical structure 5 may comprise an apex 230 of converging wires which can be gripped by a J-hook 235 formed on the distal end of tension wire 210 (FIG. 88) or by C-fingers 240 formed on the distal end of tension wire 210 (FIG. 89).

Figure 85:
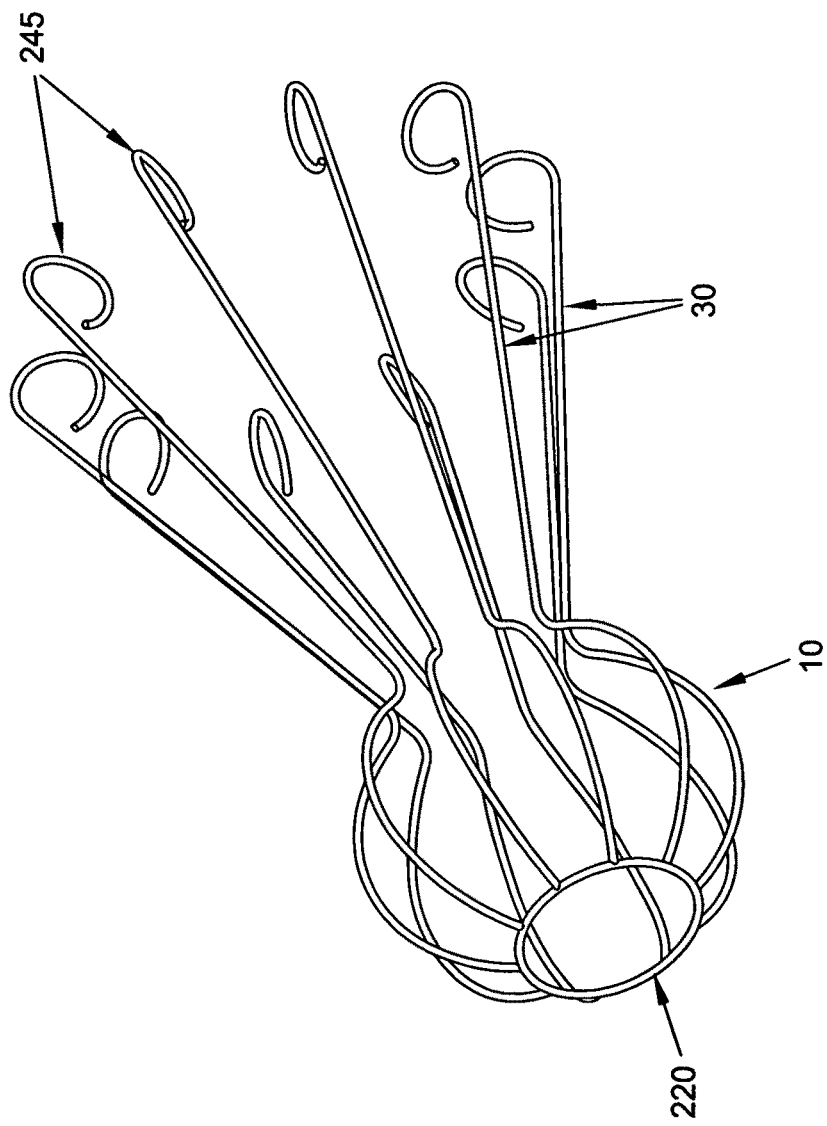
Figure 86:
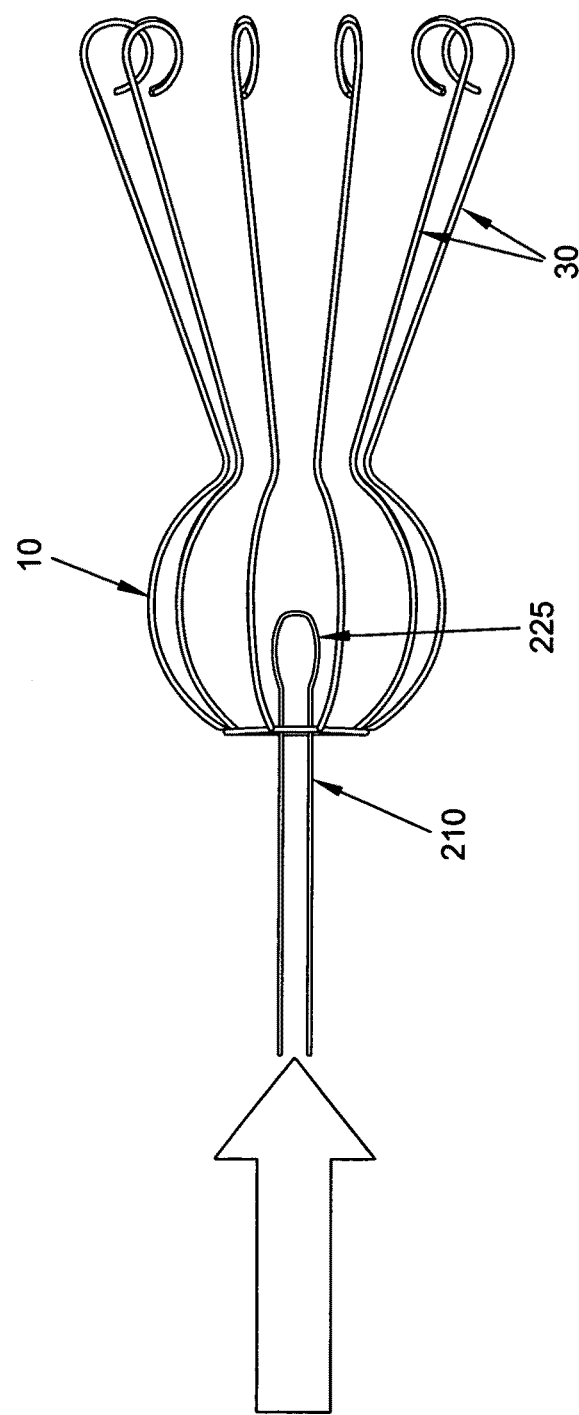
Figure 87:
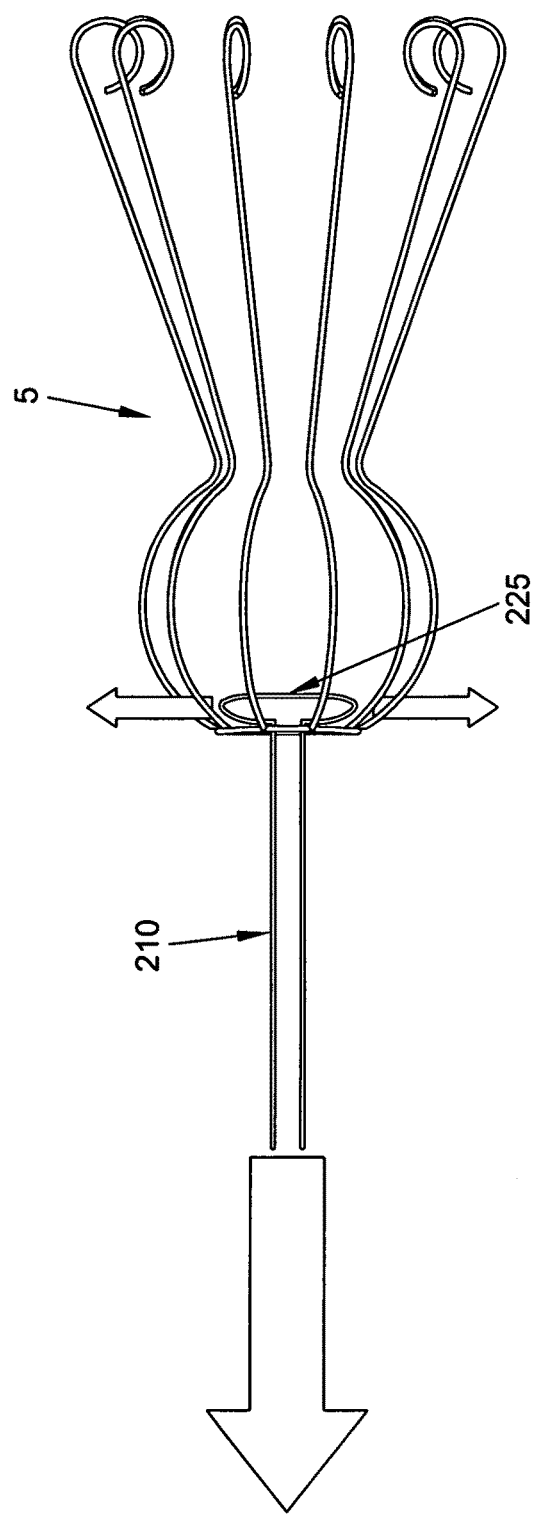

If desired, and looking now at FIGS. 85-87, the distal ends of stabilizing legs 30 may be turned into eyelets 245, so as to minimize trauma (during both placement and repositioning) to the side wall of the body lumen (e.g., blood vessel) in which they are disposed.

Figure 90:
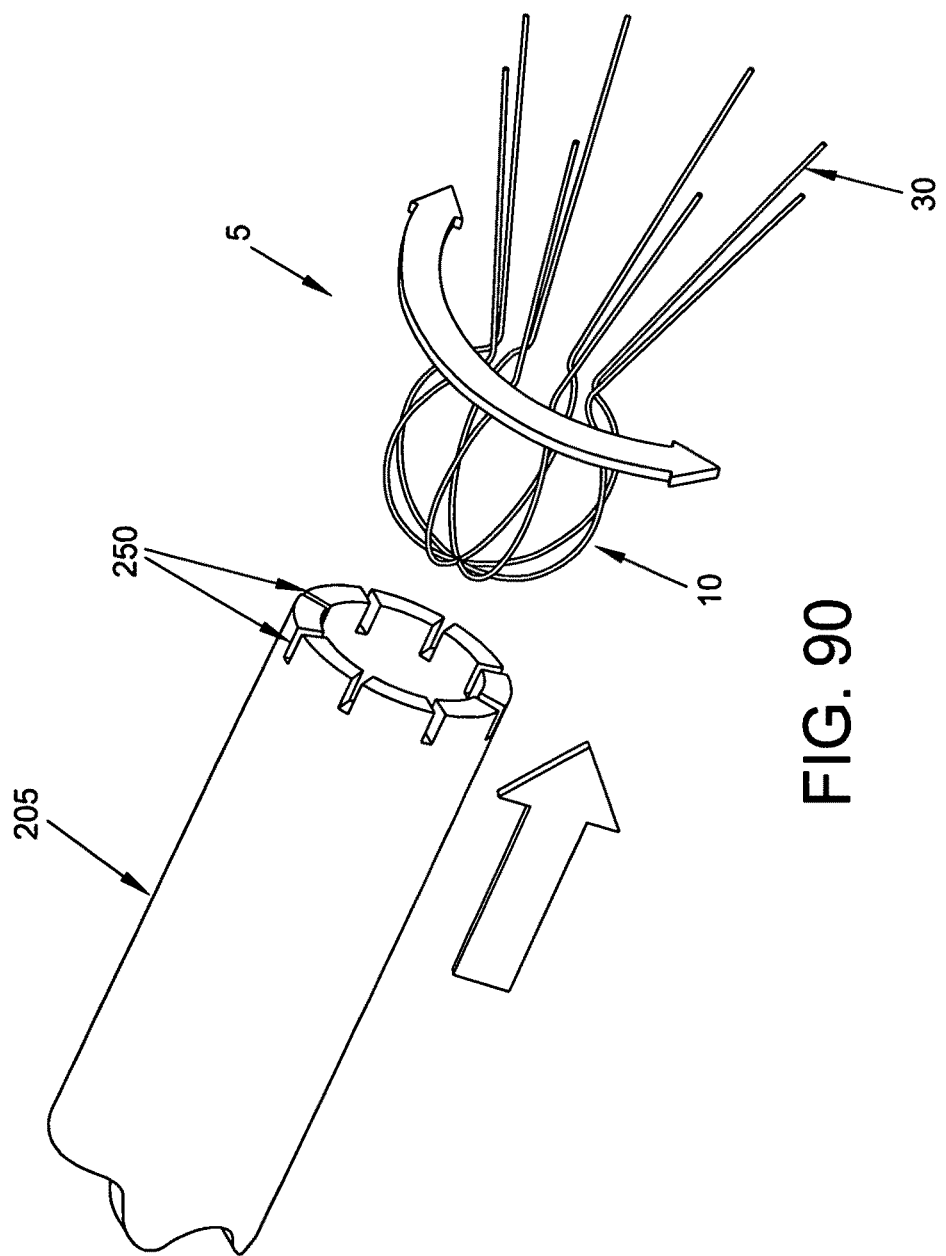
Figure 91:
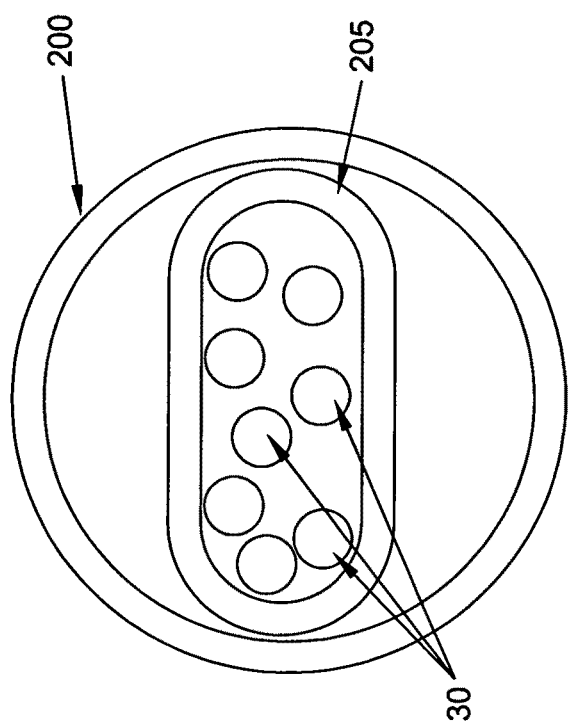

It will be appreciated that, where flow-restricting face 15 covers only a portion of the circumference of open frame 10, it can be important for the clinician to ensure the rotational disposition of the comet-shaped structure so that flow-restricting face 15 is properly aligned with the mouth of the lateral aneurysm. For this reason, and looking now at FIG. 90, push catheter 205 may include a plurality of slits 250 on its distal end which receive the constituent wires of open frame 10, whereby to permit the clinician to adjust the rotational disposition of the comet-shaped structure (and hence the rotational disposition of flow-restricting face 15 of open frame 10). Alternatively, and looking now at FIG. 91, push catheter 205 may be formed with an obround shape (or any other appropriate non-circular shape) so as to permit the clinician to specify the rotational disposition of the comet-shaped structure (and hence the rotational disposition of flow-restricting face 15 of open frame 10).

Figure 94:
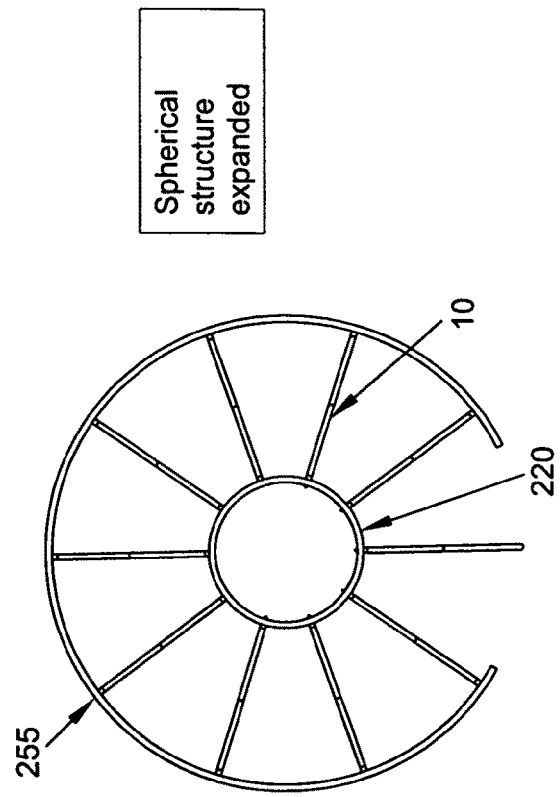
Figure 95:
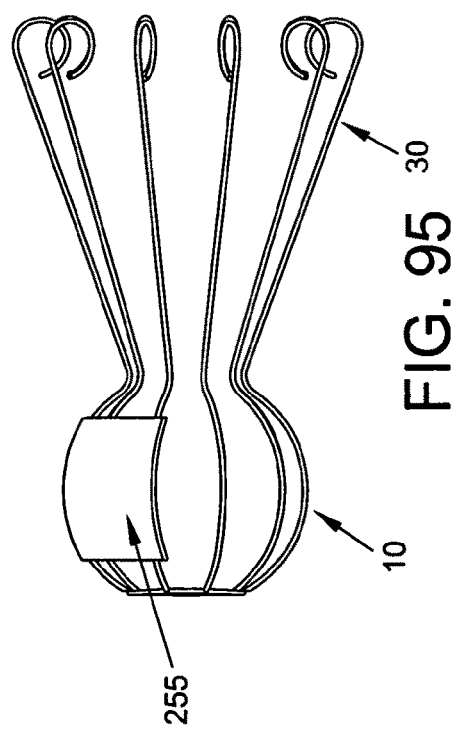
Figure 96:
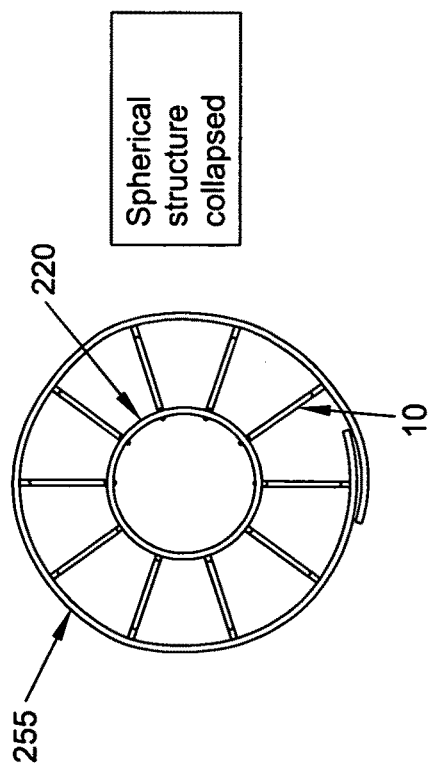
Figure 97:
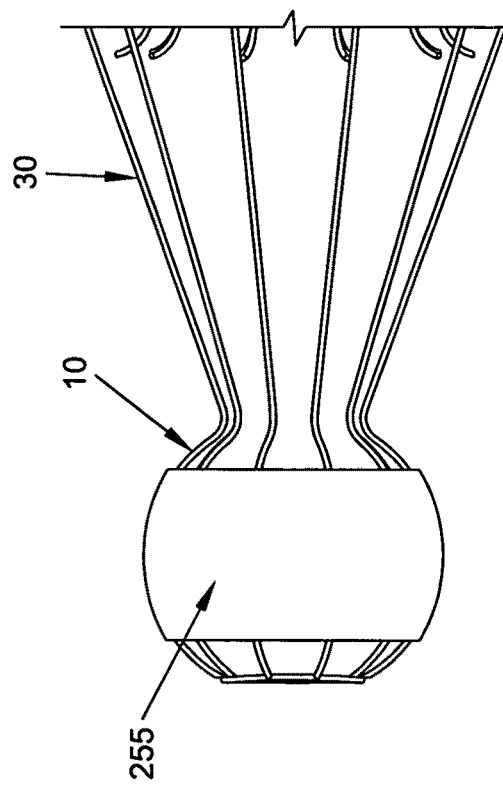

Looking now at FIGS. 92 and 93, flow-restricting face 15 of open frame 10 can be formed by wrapping a membrane 255 over the wire skeleton making up open frame 10 and securing it in position. Thus, FIGS. 94 and 95 show membrane 255 covering only a portion of the circumference of frame 10, and FIGS. 96 and 97 show membrane 255 covering the complete circumference of frame 10.

In the foregoing description, the expandable spherical structure 5 of FIGS. 82 and 83 is discussed in the context of a "legs-first" deployment into the blood vessel or other body lumen. However, it should also be appreciated that the expandable spherical structure 5 of FIGS. 82 and 83 may be deployed "head-first" into the blood vessel or other body lumen (i.e., with stabilizing legs 30 trailing open frame 10).

Figure 98:
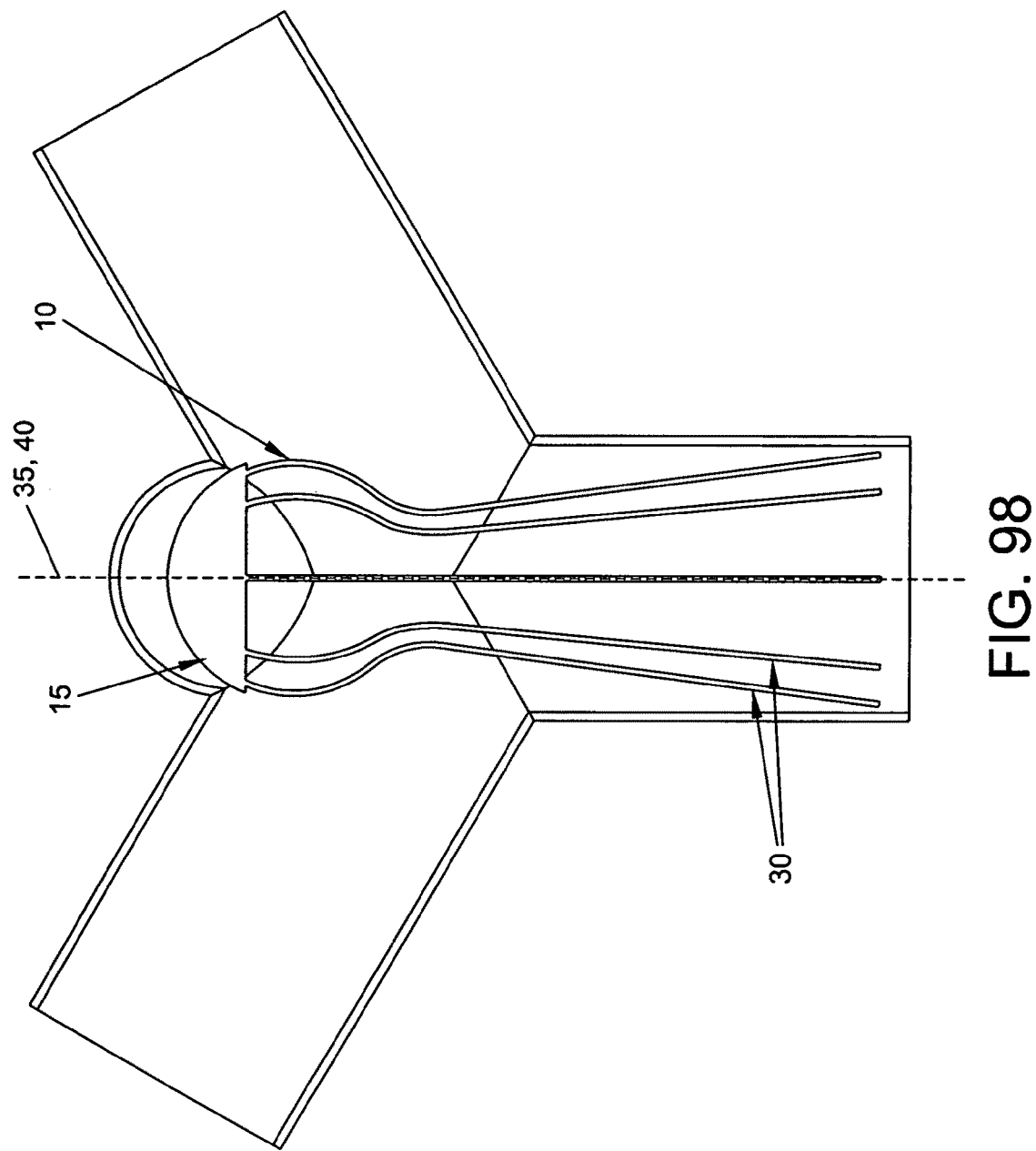
FIG. 98 is a schematic view showing another comet-shaped structure, but with this structure being configured to restrict flow to a bifurcation aneurysm.

Looking next at FIG. 98, it is also possible to provide a comet-shaped structure which can be used with a bifurcation aneurysm. More particularly, in this form of the invention, expandable spherical structure 5 is formed so that center axis 40 of flow-restricting face 15 is aligned with center axis 35 of stabilizing legs 30. It will be appreciated that where the comet-shaped structure is to be used with to treat a bifurcation aneurysm, it is generally desirable that the "head" of the comet (which comprises flow-restricting face 15) be ejected out of containment sheath 200 first, with stabilizing legs 30 trailing, whereby to easily place flow-restricting face 15 against the mouth of the aneurysm.

Expandable Spherical Structure Formed Out of a "Closed Loop" of Filament

In the preceding description, expandable spherical structure 5 is described as comprising an open frame 10 having a flow-restricting face 15 carried thereon. More particularly, in some embodiments of the invention, flow-restricting face 15 comprises a substantially complete surface or barrier. See, for example, FIGS. 4-49. However, in other embodiments of the invention, flow-restricting face 15 need not comprise a substantially complete surface or barrier, i.e., flow-restricting face 15 may be formed with a face having a sufficiently high strut density to form an effectively closed face or to otherwise achieve a desired purpose. Thus, for example, in FIGS. 50-58, there is shown an expandable spherical structure 5 comprising an open frame 10 having a flow-restricting face 15 formed with a high strut density such that blood flow to the aneurysm will be restricted and the aneurysm will thrombose. In this circumstance, flow-restricting face 15 may be considered to be effectively closed, in the sense that flow-restricting face 15 is sufficiently closed to decrease flow velocity in the aneurysm and result in thrombosis within the aneurysm. Furthermore, where flow-restricting face 15 is being used to reinforce a weakness in a side wall (as opposed to being used to close off an opening in a side wall or to otherwise restrict flow through that opening), flow-restricting face 15 may have a somewhat lower strut density. In any case, however, flow-restricting face 15 will still have a significantly higher strut density than that of open frame 10.

In the preceding description, it was noted that it is possible to form the entire expandable spherical structure 5 out of a single superelastic wire, e.g., a shape-memory alloy constructed so as to form stress-induced martensite at body temperatures. It was also noted that, in this form of the invention, the expandable spherical structure 5 can be (i) deformed into a collapsed configuration wherein a single path of the wire is constrained within a constraining cannula, and (ii) thereafter reformed in situ by simply pushing the wire out of the distal end of the restraining cannula, whereupon expandable spherical structure 5 reforms in the blood vessel or other body lumen. It was further noted that this form of the invention is particularly well suited to constructions wherein closed face 15 is formed with a single, patterned strut arranged to have a high strut density, e.g., with a strut density sufficiently high to restrict the flow of blood through the mouth of an aneurysm (i.e., to cause thrombosis of the aneurysm), and/or a strut density sufficiently high to reinforce the side wall of a blood vessel or other body lumen, and/or a strut density sufficiently high to achieve some other desired purpose. Again, however, flow-restricting face 15 will still have a significantly higher strut density than that of open frame 10. See, for example, FIGS. 59-63, which show flow-restricting face 15 formed out of a single, patterned strut, where the strut pattern may comprise one or more of a variety of configurations, e.g., with parallel paths, concentric paths, switchback patterns, serpentine paths, etc.

In accordance with the present invention, there is now disclosed a further construction wherein expandable spherical structure 5 is formed out of a closed loop of filament such as highly flexible wire (e.g., Nitinol) which has been worked (e.g., on a mandrel) so that its numerous turns approximate the shape of a sphere or ellipsoid when the loop is in its relaxed condition. One face of the sphere (i.e., flow-restricting face 15) has a higher turn density than the remainder of the sphere (i.e., open frame 10) so that the high density face can restrict blood flow while the remainder of the sphere easily passes blood flow. The closed loop of filament may be transformed from its spherical shape into another shape by applying physical forces (e.g., tension) to the closed loop of filament. Thus, the closed loop of filament may be transformed from its three-dimensional substantially spherical configuration into a substantially two-dimensional "elongated loop" configuration (e.g., by applying two opposing forces to the interior of the loop) in order that the closed loop of filament may be advanced endoluminally to the site of an aneurysm. Once at the site of the aneurysm, the tension on the elongated loop may be released so that the closed loop of filament returns to its spherical shape, whereby to lodge in the blood vessel with the high density face (i.e., flow-restricting face 15) diverting the flow of blood away from the aneurysm (i.e., to cause thrombosis within the aneurysm) while the remainder of the sphere (i.e., open frame 10) easily passes blood flowing through the parent vessel. If the sphere subsequently needs to be re-positioned within the blood vessel, the tension is re-applied to the sphere so as to transform it part or all the way back to its elongated loop configuration, the position of the device is adjusted, and then the foregoing process repeated so as to set the sphere at a new position within the blood vessel. Furthermore, if the sphere needs to be removed from the blood vessel, the tension is re-applied to the sphere so as to transform it back to its elongated loop configuration, and then the loop is removed from the patient. Significantly, this construction has the advantages of (i) ease of positioning, (ii) reliably maintaining its deployed position within the vessel, (iii) ease of re-positioning within the body, and (iv) where necessary, removal from the body.

Figure 63:
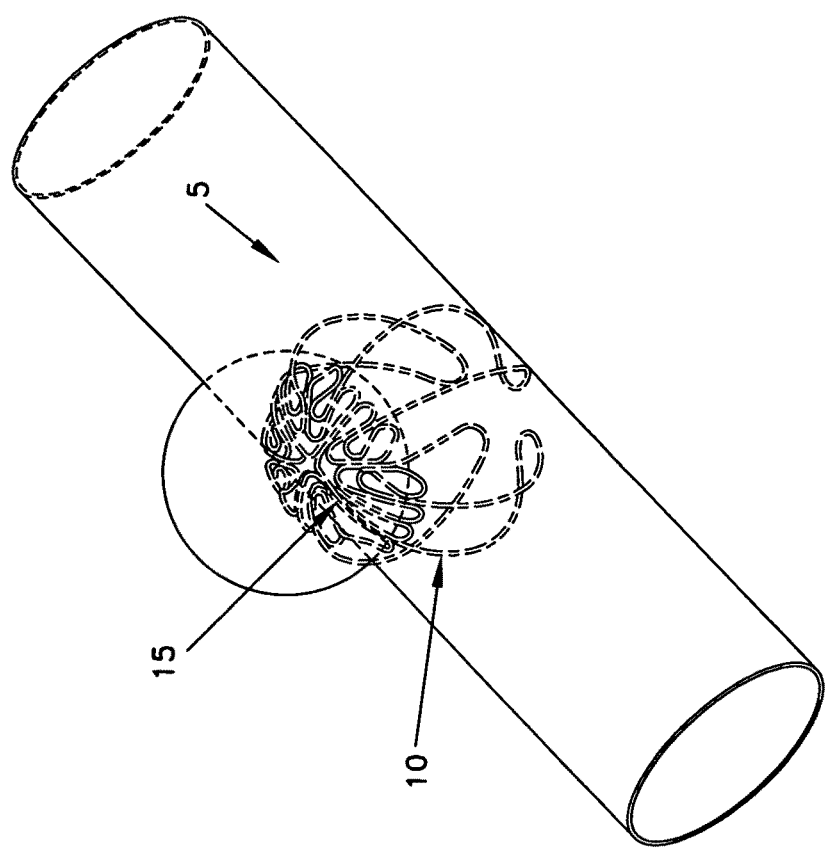
Figure 99:
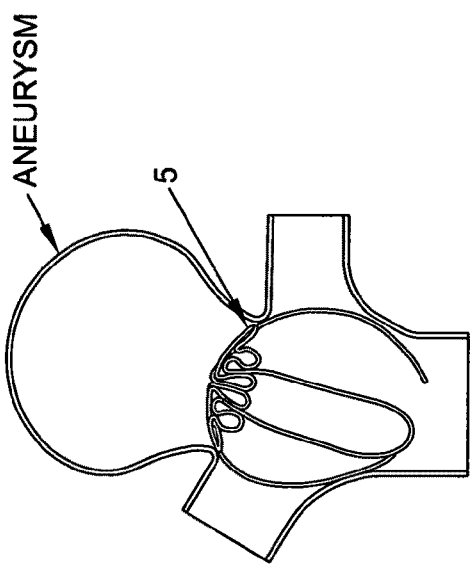
FIGS. 99 and 100 show an expandable spherical structure restricting flow into a bifurcation aneurysm, where the expandable spherical structure is formed out of a "closed loop" of filament, and where the expandable spherical structure is deployed in the patient so that the face having a high strut density is positioned over the mouth/neck of the aneurysm in order to restrict flow into the aneurysm.
Figure 100:
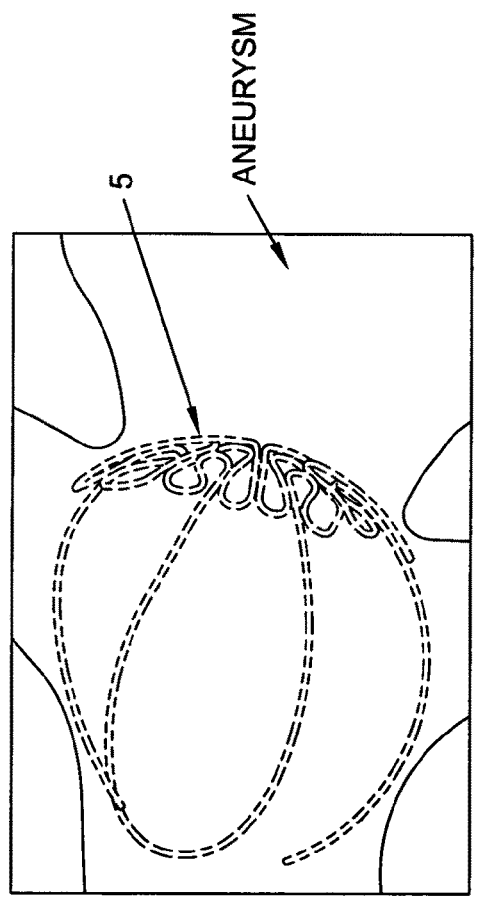

By way of example but not limitation, FIG. 63 shows a expandable spherical structure 5 which is formed out of a closed loop of highly flexible wire. As can be seen in FIG. 63, expandable spherical structure 5 approximates the shape of a sphere or ellipsoid when the loop is in its relaxed condition. FIG. 63 shows expandable spherical structure 5 being used to restrict blood flow to a lateral aneurysm. FIGS. 99 and 100 show expandable spherical structure 5 being used to restrict blood flow to a bifurcation aneurysm.

Figure 101:
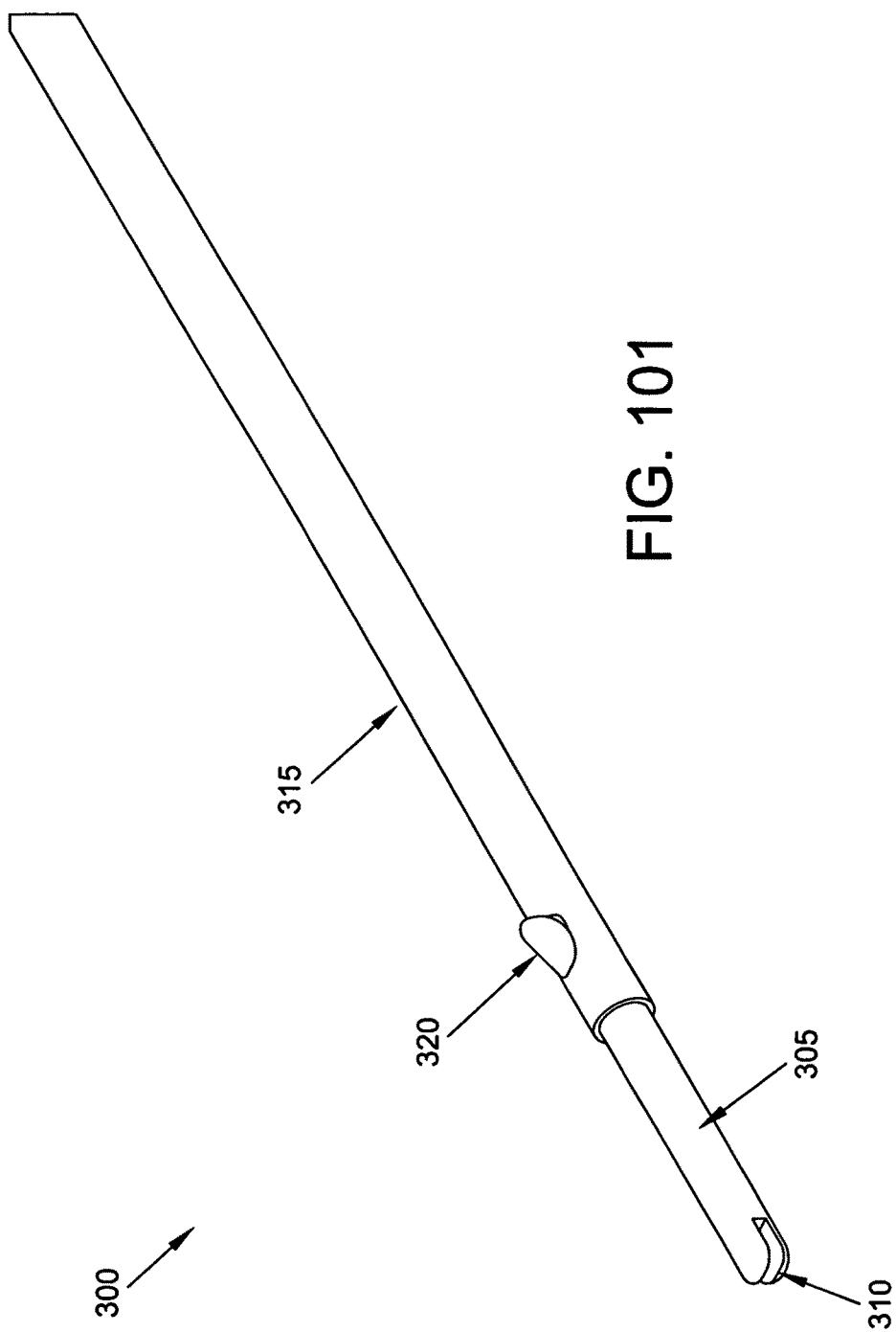
FIGS. 101 and 102 are schematic views of an inserter which may be used with an expandable spherical structure formed out of a "closed loop" of filament.
Figure 102:
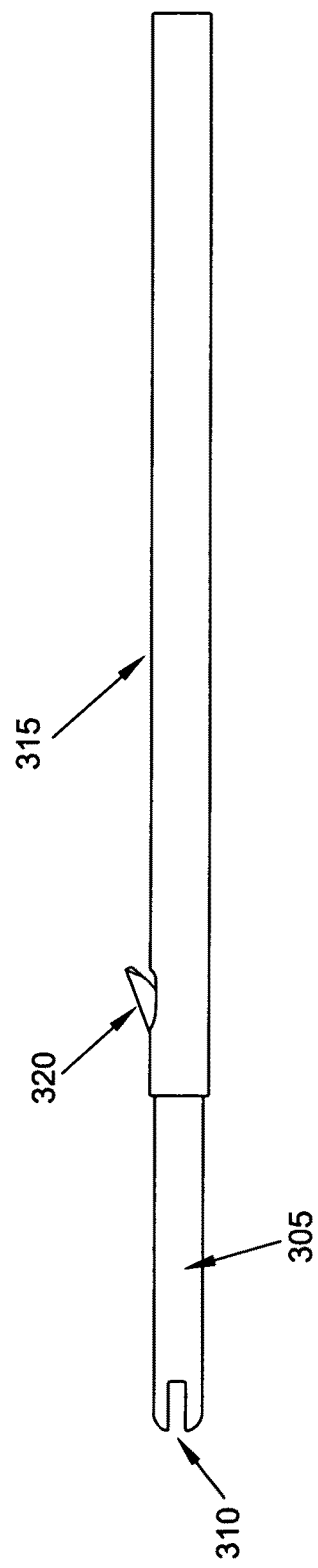
Figure 103:
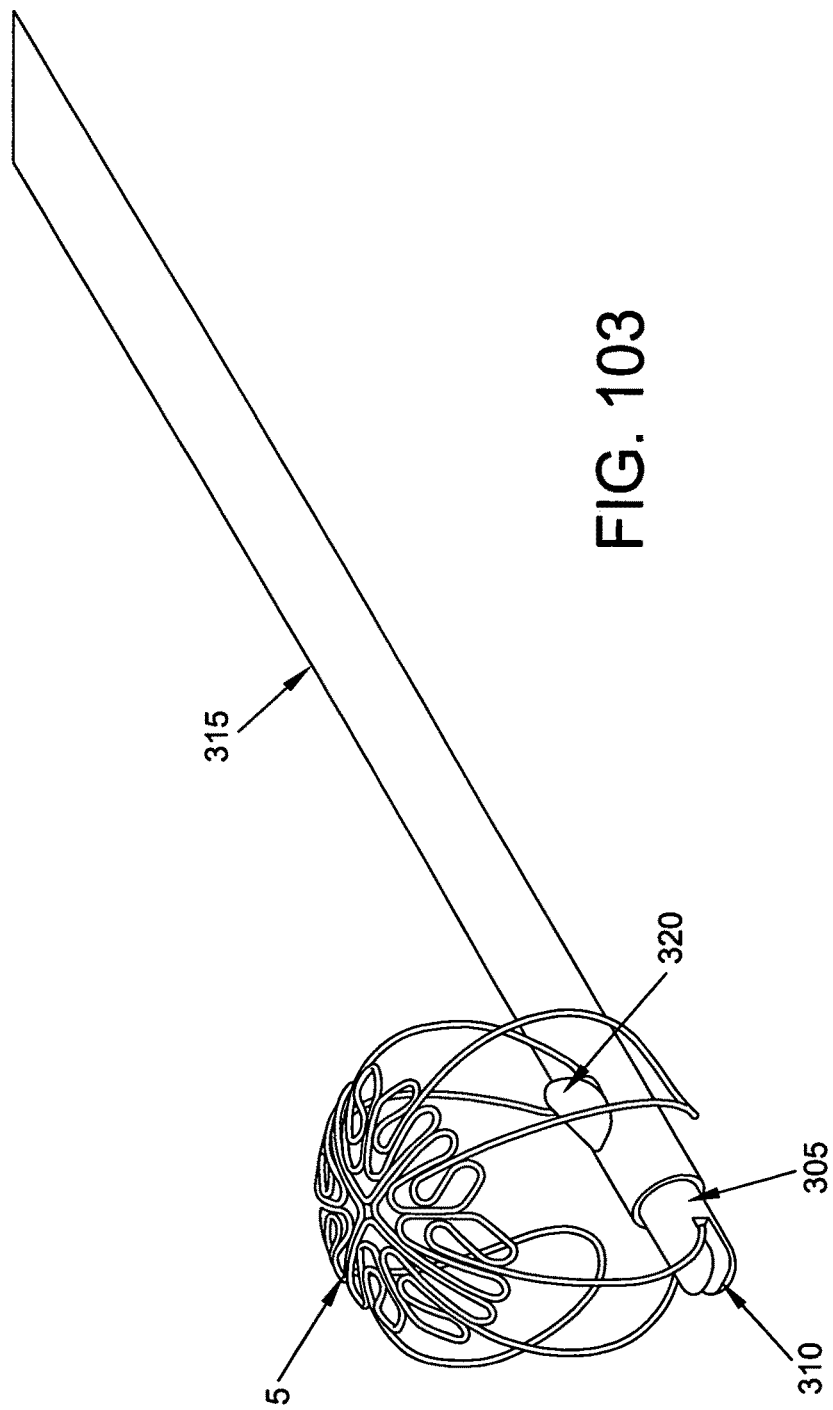
FIGS. 103-107 are schematic views showing how an expandable spherical structure formed out of a "closed loop" of filament may be deployed using the inserter of FIGS. 101 and 102.
Figure 104:
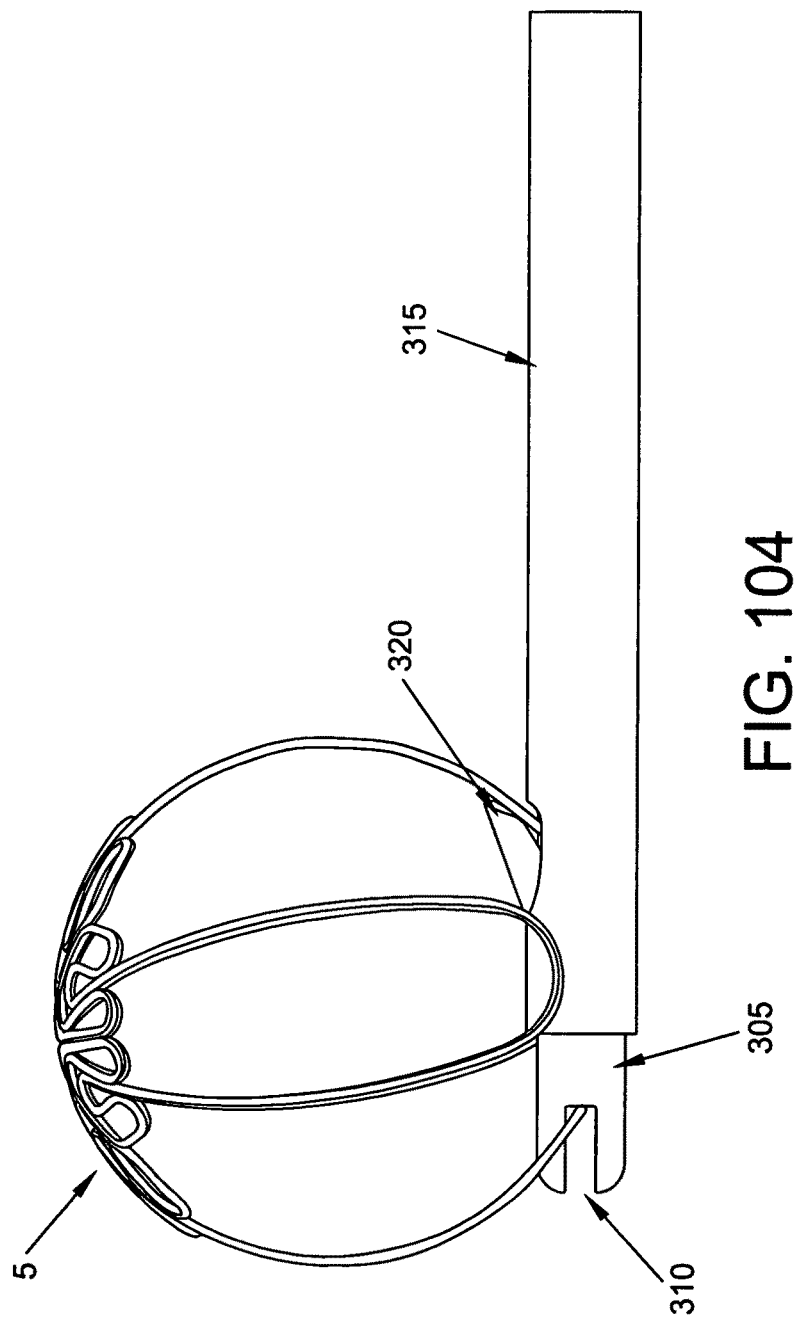
Figure 105:
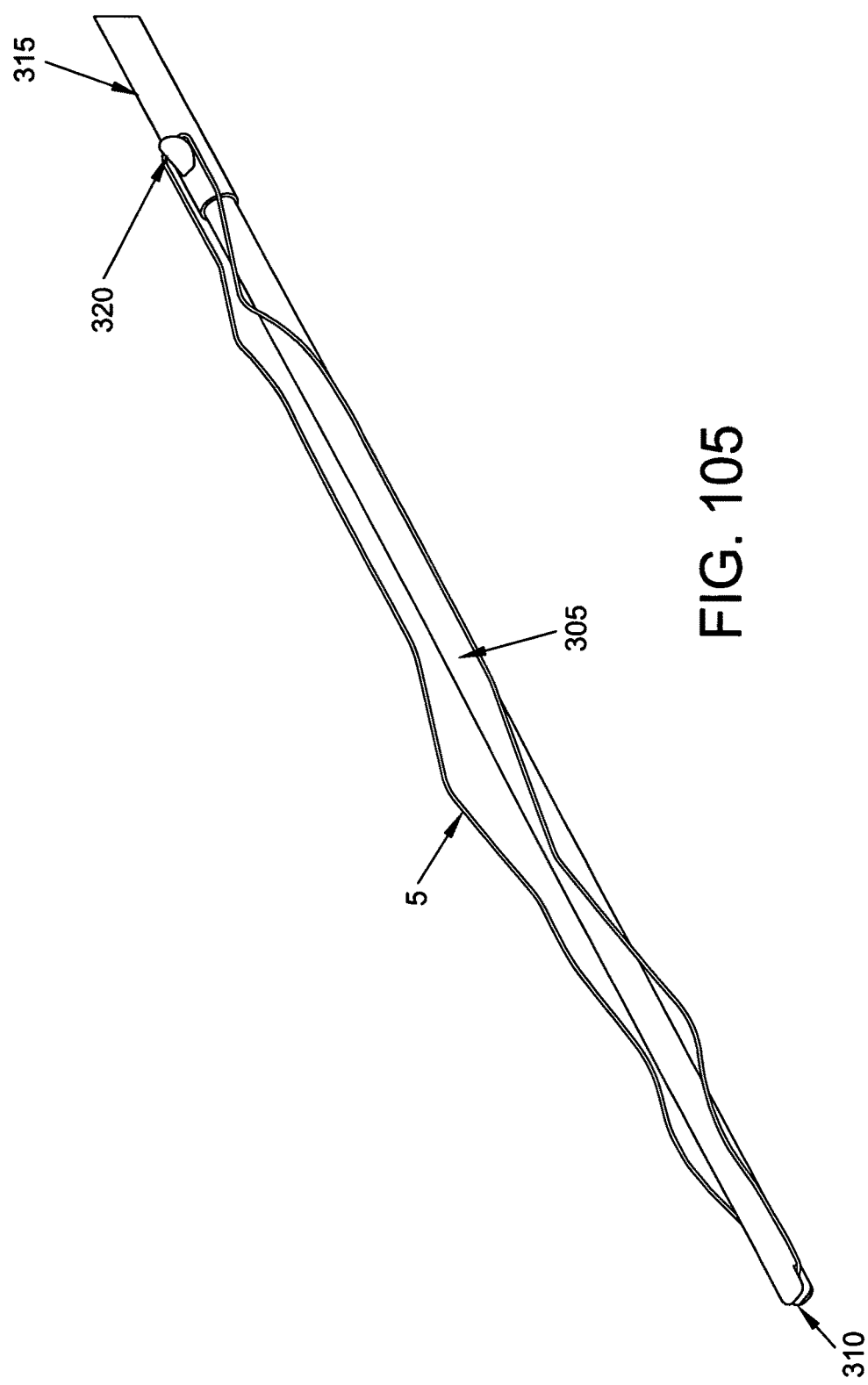
Figure 106:
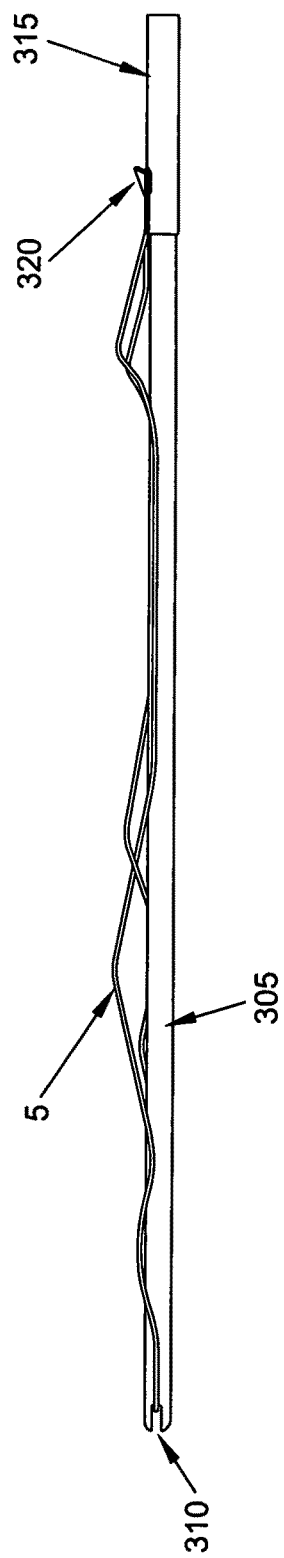
Figure 107:
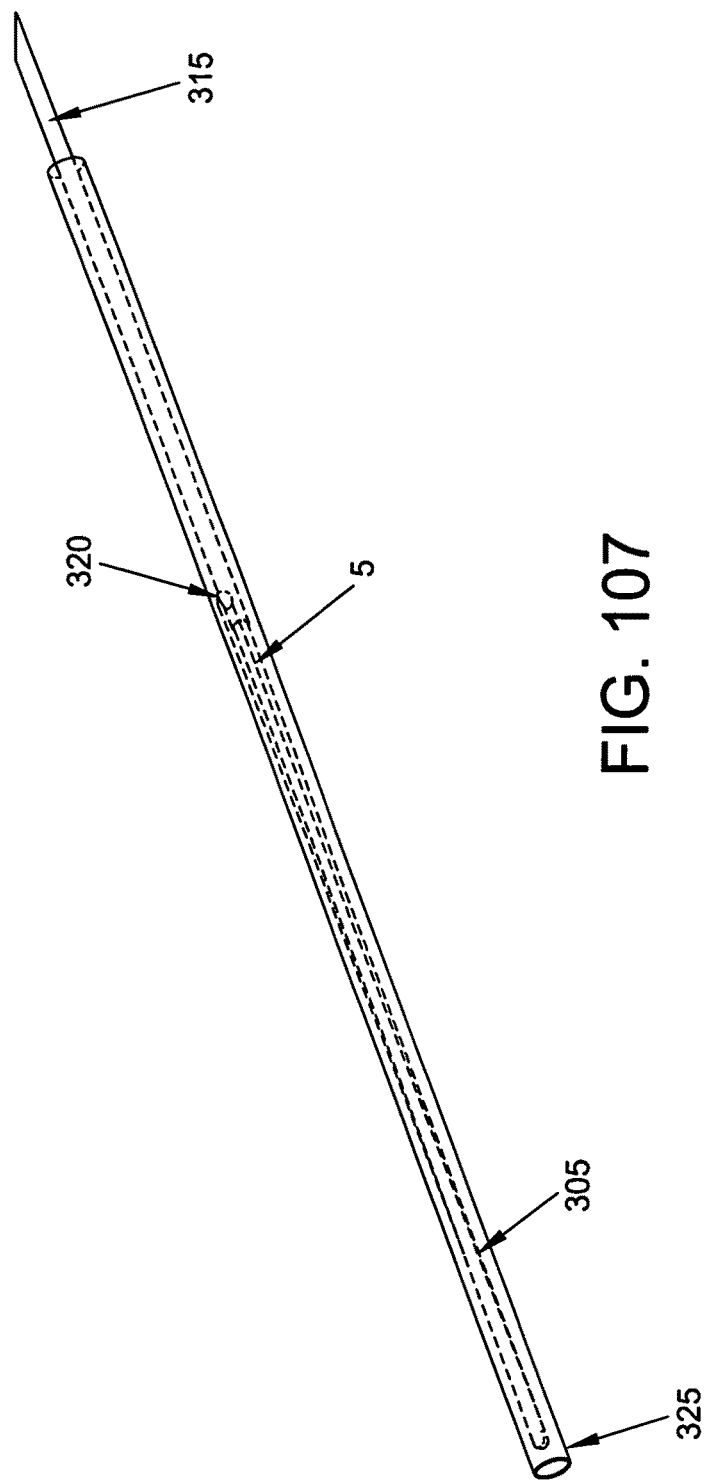

FIGS. 101 and 102 shows an inserter 300 which can be used to reconfigure such a "closed loop" expandable spherical structure 5 from its relaxed spherical (or elliptical) configuration into an elongated loop configuration. To this end, inserter 300 preferably comprises an inner catheter 305 which includes a bifurcated distal end 310 which can seat a segment of the closed loop. Inserter 300 preferably also comprises an outer catheter 315 which includes a mount 320 which can seat another segment of the closed loop.

In use, and as shown in FIGS. 103-107, inserter 300 is set so that its outer catheter 315 is adjacent to bifurcated distal end 310, and then a segment of the closed loop expandable spherical structure 5 is seated in bifurcated distal end 310 and another segment of the closed loop expandable spherical structure is seated in mount 320 of outer catheter 315. Then outer catheter 315 is moved proximally so that the closed loop expandable spherical structure 5 is reconfigured from its relaxed spherical (or elliptical) configuration into an elongated loop configuration, e.g., in the manner of a tensioned elastic band. With the closed loop expandable spherical structure 5 held in this elongated condition on inserter 300, a transport sheath 325 is (optionally) be placed over the assembly. Inserter 300 (with its passenger closed loop expandable spherical structure 5 and with its overlying transport sheath 325) is moved through the patient's anatomy until spherical structure 5 is located at the surgical site. Then transport sheath 325 is removed and outer catheter 315 is moved distally on inner catheter 305. As outer catheter 315 is moved distally on inner catheter 305, tension on expandable spherical structure 5 is released so that expandable spherical structure 5 can re-assume its spherical or elliptical shape and engage the adjacent anatomy. Then expandable spherical structure 5 is disengaged from inserter 300, and inserter 300 is removed from the surgical site.

If, after deployment, the closed loop expandable spherical structure needs to be re-positioned within the blood vessel, inserter 300 is used to re-apply tension to the sphere so as to transform the sphere part or all the way back to its loop configuration, the position of the device is adjusted, and then the foregoing process is repeated so as to set the sphere at a new position within the blood vessel.

Furthermore, if, after deployment, the closed loop expandable spherical structure 5 needs to be removed from the blood vessel, inserter 300 is used to re-apply tension to the sphere so as to transform it back to its loop configuration, and then the loop is removed from the patient.

Significantly, this construction has the advantages of (i) ease of positioning, (ii) reliably maintaining its deployed position within the vessel, (iii) ease of re-positioning within the body, and (iv) where necessary, removal from the body.

Terminology

In the foregoing disclosure, expandable spherical structure 5 is described as comprising a spherical body. In this regard, it should be appreciated that the term "spherical" is intended to mean a true spherical shape, and/or a substantially spherical shape, and/or a near spherical shape (including but not limited to an ellipsoid shape or a substantially ellipsoid shape or a near ellipsoid shape), and/or an effectively spherical shape, and/or a generally spherical shape, and/or a polyhedron which approximates a sphere, and/or a shape which approximates a sphere, and/or a structure comprising a substantial portion of any of the foregoing, and/or a structure comprising a combination of any of the foregoing, etc.

Thus, for example, expandable spherical structure 5 may include a first section that constitutes a portion of a sphere and a second section which roughly approximates the remaining portion of a sphere.

Modifications

It will be appreciated that still further embodiments of the present invention will be apparent to those skilled in the art in view of the present disclosure. It is to be understood that the present invention is by no means limited to the particular constructions herein disclosed and/or shown in the drawings, but also comprises any modifications or equivalents within the scope of the invention.

What is claimed is:

1. A device for positioning within a lumen of a blood vessel, adjacent to the mouth of an aneurysm extending from the blood vessel, for causing thrombosis of the aneurysm while maintaining substantially normal blood flow through the lumen of the blood vessel, the device consisting of:
   a single closed loop of elastic filament configurable between:
   (i) an elongated, substantially linear configuration formed by two parallel lengths of the closed loop of elastic filament, whereby to facilitate movement along the lumen of the blood vessel; and
   (ii) a spheroidal configuration for lodging within the lumen of the blood vessel, the spheroidal configuration providing (a) a single flow-restricting face sized and configured so as to cover the mouth of the aneurysm and restrict blood flow to the aneurysm, the size of the single flow-restricting face being larger than the mouth of the aneurysm so that the single flow-restricting face seats against the mouth of the aneurysm so as to restrict blood flow to the aneurysm while permitting substantially normal blood flow through the blood vessel when the flow-restricting face is positioned over the mouth of the aneurysm, with the degree of restriction at the mouth of the aneurysm being such that the aneurysm thromboses when the single flow-restricting face is positioned over the mouth of the aneurysm, the single, flow-restricting face comprising a plurality of lengths of the closed loop of elastic filament disposed in close proximity to one another, and (b) an open frame for engaging the interior side wall of the blood vessel and holding the single flow-restricting face against the mouth of the aneurysm, the open frame configured so as to maintain substantially normal blood flow through the lumen of the blood vessel, wherein the single flow-restricting face has a higher density of wire than the open frame.

2. A device according to claim 1 wherein the single flow-restricting face is not impervious to fluid flow.

3. A device according to claim 1 wherein the dimensions of the spheroidal configuration are established by the size of the blood vessel.

4. A device according to claim 1 wherein the single closed loop of elastic filament is configured to assume its spheroidal configuration in situ within the blood vessel.

5. A device according to claim 1 wherein the single closed loop of elastic filament comprises a resilient material.

6. A device according to claim 5 wherein the resilient material comprises a shape memory alloy.

7. A device according to claim 5 wherein the resilient material comprises a polymer.

8. A device according to claim 1 wherein the single closed loop of elastic filament is configured to assume its elongated, substantially linear configuration when cooled to a temperature below body temperature and to assume its spheroidal configuration when heated to body temperature.

9. A device according to claim 1 wherein the single closed loop of elastic filament is configured to transform from its spheroidal configuration to its elongated, substantially linear configuration by the application of mechanical stress.

10. A device according to claim 1 wherein the single closed loop of elastic filament is configured to transform from its elongated, substantially linear configuration to its spheroidal configuration by the release of mechanical stress.

11. A device according to claim 1 further comprising
an installation tool for carrying the single closed loop of elastic filament to a deployment site, wherein the installation tool comprises:
an elongated structure having a first mount for seating a first portion of the single closed loop of elastic filament and a second mount for seating a second portion of the single closed loop of elastic filament, the first mount and the second mount being movable relative to one another between a first position and a second position so that (i) when the first portion of the single closed loop of elastic filament is seated in the first mount and the second portion of the single closed loop of elastic filament is seated in the second mount and the first mount and the second mount are in their first position, the single closed loop of elastic filament is in its spheroidal configuration, and (ii) when the first portion of the single closed loop of elastic filament is seated in the first mount and the second portion of the single closed loop of elastic filament is seated in the second mount and the first mount and second mount are in their second position, the single closed loop of elastic filament is in its elongated, substantially linear configuration.

12. A device according to claim 11 wherein the elongated structure comprises a hollow catheter.

13. A device according to claim 11 wherein the first mount of the installation tool is formed by a slot in the distal end of the elongated structure.

14. A device according to claim 11 wherein the second mount of the installation tool is formed by a projection extending laterally from the elongated structure.

15. A device according to claim 11 wherein the first mount is fixed in position on the elongated structure and the second mount is movable relative to the elongated structure.

16. A device according to claim 11 further comprising a hollow sleeve sized to receive the single closed loop of elastic filament when the single closed loop of elastic filament is mounted on the elongated structure.

17. A device according to claim 1 wherein the plurality of lengths of the closed loop of elastic filament are disposed in a patterned configuration.

18. A device according to claim 1 wherein the plurality of lengths of the closed loop of elastic filament are disposed in a non-overlapping configuration.

19. A device according to claim 1 wherein the plurality of lengths of the closed loop of elastic filament are disposed in an ordered configuration.

20. A device according to claim 1 wherein the plurality of lengths of the closed loop of elastic filament are disposed in a nestled configuration.

21. A device according to claim 1 wherein the plurality of lengths of the closed loop of elastic filament are disposed in a pre-determined configuration.

22. A device according to claim 1 wherein the plurality of lengths of the closed loop of elastic filament are disposed in a switchback configuration.

23. A method for causing thrombosis of an aneurysm extending from a blood vessel while maintaining substantially normal blood flow through the lumen of the blood vessel, the method comprising:
providing a device consisting of:
a single closed loop of elastic filament configurable between:
(i) an elongated, substantially linear configuration formed by two parallel lengths of the closed loop of elastic filament, whereby to facilitate movement along the lumen of the blood vessel; and
(ii) a spheroidal configuration for lodging within the lumen of the blood vessel, the spheroidal configuration providing (a) a single flow-restricting face sized and configured so as to cover the mouth of the aneurysm and restrict blood flow to the aneurysm, the size of the single flow-restricting face being larger than the mouth of the aneurysm so that the single flow-restricting face seats against the mouth of the aneurysm so as to restrict blood flow to the aneurysm while permitting substantially normal blood flow through the blood vessel when the single flow-restricting face is positioned over the mouth of the aneurysm, with the degree of restriction at the mouth of the aneurysm being such that the aneurysm thromboses when the single flow-restricting face is positioned over the mouth of the aneurysm, the single flow-restricting face comprising a plurality of lengths of the closed loop of elastic filament disposed in close proximity to one another, and (b) an open frame for engaging the interior side wall of the blood vessel and holding the single flow-restricting face against the mouth of the aneurysm, the open frame configured so as to maintain substantially normal blood flow through the lumen of the blood vessel, wherein the single flow-restricting face has a higher density of wire than the open frame;
delivering the single closed loop of elastic filament to the aneurysm site while the single closed loop of elastic filament is configured in its elongated configuration; and
transforming the single closed loop of elastic filament to its spheroidal configuration so that the single closed loop of elastic filament is lodged against the mouth of the aneurysm, with the single flow-restricting face being positioned over the mouth of the aneurysm so as to restrict blood flow to the aneurysm while permitting substantially normal blood flow through the blood vessel and with the open frame maintaining substantially normal blood flow through the lumen of the blood vessel.

24. A method according to claim 23 wherein the aneurysm comprises a lateral aneurysm.

25. A method according to claim 23 wherein the aneurysm comprises a bifurcation aneurysm.

26. A method according to claim 23 wherein the dimensions of the spheroidal configuration are established by the size of the blood vessel.

27. A method according to claim 23 wherein the single closed loop of elastic filament is configured to assume its spheroidal configuration in situ within the blood vessel.

28. A method according to claim 23 wherein the single closed loop of elastic filament is configured to transform from its spheroidal configuration to its elongated, substantially linear configuration by the application of mechanical stress.

29. A method according to claim 23 wherein the single closed loop of elastic filament is configured to transform from its elongated, substantially linear configuration to its spheroidal configuration by the release of mechanical stress.

30. A method according to claim 23 wherein the plurality of lengths of the closed loop of elastic filament are disposed in a patterned configuration.

31. A method according to claim 23 wherein the plurality of lengths of the closed loop of elastic filament are disposed in a non-overlapping configuration.

32. A method according to claim 23 wherein the plurality of lengths of the closed loop of elastic filament are disposed in an ordered configuration.

33. A method according to claim 23 wherein the plurality of lengths of the closed loop of elastic filament are disposed in a nestled configuration.

34. A method according to claim 23 wherein the plurality of lengths of the closed loop of elastic filament are disposed in a pre-determined configuration.

35. A method according to claim 23 wherein the plurality of lengths of the closed loop of wire are disposed in a switchback configuration.

36. A method according to claim 23 wherein the single flow-restricting face is not impervious to fluid flow.

37. A method according to claim 23 wherein the single closed loop of elastic filament comprises a resilient material.

38. A method according to claim 37 wherein the resilient material comprises a shape memory alloy.

39. A method according to claim 37 wherein the resilient material comprises a polymer.

40. A method according to claim 23 wherein the single closed loop of elastic filament is configured to assume its elongated, substantially linear configuration when cooled to a temperature below body temperature and to assume its spheroidal configuration when heated to body temperature.

41. A method according to claim 23 further comprising an installation tool for carrying the single closed loop of elastic filament to a deployment site, wherein the installation tool comprises:

an elongated structure having a first mount for seating a first portion of the single closed loop of elastic filament and a second mount for seating a second portion of the single closed loop of elastic filament, the first mount and the second mount being movable relative to one another between a first position and a second position so that (i) when the first portion of the single closed loop of elastic filament is seated in the first mount and the second portion of the single closed loop of elastic filament is seated in the second mount and the first mount and the second mount are in their first position, the single closed loop of elastic filament is in its spheroidal configuration, and (ii) when the first portion of the single closed loop of elastic filament is seated in the first mount and the second portion of the single closed loop of elastic filament is seated in the second mount and the first mount and second mount are in their second position, the single closed loop of elastic filament is in its elongated, substantially linear configuration.

42. A method according to claim 41 wherein the elongated structure comprises a hollow catheter.

43. A method according to claim 41 wherein the first mount of the installation tool is formed by a slot in the distal end of the elongated structure.

44. A method according to claim 41 wherein the second mount of the installation tool is formed by a projection extending laterally from the elongated structure.

45. A method according to claim 41 wherein the first mount is fixed in position on the elongated structure and the second mount is movable relative to the elongated structure.

46. A method according to claim 41 further comprising a hollow sleeve sized to receive the single closed loop of elastic filament when the single closed loop of elastic filament is mounted on the elongated structure.

* * * * *